US 9,802,930 B1

(12) United States Patent
Tanabe et al.

(10) Patent No.: US 9,802,930 B1
(45) Date of Patent: Oct. 31, 2017

(54) PYRIMIDINONE COMPOUND

(71) Applicant: Sumitomo Chemical Company, Limited, Tokyo (JP)

(72) Inventors: Takamasa Tanabe, Takarazuka (JP); Yoshihiko Nokura, Takarazuka (JP); Ryota Maehata, Takarazuka (JP); Kohei Orimoto, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/515,868

(22) PCT Filed: Sep. 18, 2015

(86) PCT No.: PCT/JP2015/076611
§ 371 (c)(1),
(2) Date: Mar. 30, 2017

(87) PCT Pub. No.: WO2016/052247
PCT Pub. Date: Apr. 7, 2016

(30) Foreign Application Priority Data

Oct. 3, 2014 (JP) ................................ 2014-204514

(51) Int. Cl.
| | | |
|---|---|---|
| A61K 31/54 | (2006.01) |
| C07D 417/14 | (2006.01) |
| C07D 239/34 | (2006.01) |
| A01N 43/54 | (2006.01) |
| C07D 239/36 | (2006.01) |
| C07D 401/04 | (2006.01) |
| C07D 401/14 | (2006.01) |
| A01N 43/653 | (2006.01) |
| A01N 43/78 | (2006.01) |
| A01N 43/84 | (2006.01) |

(52) U.S. Cl.
CPC ........... *C07D 417/14* (2013.01); *A01N 43/54* (2013.01); *A01N 43/653* (2013.01); *A01N 43/78* (2013.01); *A01N 43/84* (2013.01); *C07D 239/34* (2013.01); *C07D 239/36* (2013.01); *C07D 401/04* (2013.01); *C07D 401/14* (2013.01)

(58) Field of Classification Search
CPC ..................................................... A61K 31/54
See application file for complete search history.

(56) References Cited

FOREIGN PATENT DOCUMENTS

| | | |
|---|---|---|
| JP | H06220023 A | 8/1994 |
| WO | 0029387 A1 | 5/2000 |
| WO | 0168613 A1 | 9/2001 |
| WO | 2010093595 A1 | 8/2010 |

OTHER PUBLICATIONS

Kudo et al., 2001, caplus an 2001:693290.*
Naidu, 2008, caplus an 408547.*
Int'l Search Report dated Dec. 22, 2015 in Int'l Application No. PCT/JP2015/076611.
Int'l Preliminary Report on Patentability dated Apr. 4, 2017 in Int'l Application No. PCT/JP2015/076611.

\* cited by examiner

*Primary Examiner* — Sun Jae Yoo
(74) *Attorney, Agent, or Firm* — Panitch Schwarze Belisario & Nadel LLP

(57) ABSTRACT

A pyrimidinone compound represented by formula (1):

(1)

[wherein: $A^1$ represents a nitrogen atom or a $CR^4$; $A^2$ represents a nitrogen atom and $A^3$ represents a $CR^{3b}$, or $A^2$ represents a $CR^{3a}$ and $A^3$ represents a nitrogen atom; Q represents an oxygen atom or a sulfur atom; G represents a C2-C10 chain hydrocarbon group having one or more halogen atoms, etc.; $R^1$ represents a C1-C6 chain hydrocarbon group optionally having one or more halogen atoms; $R^2$ represents a C1-C6 chain hydrocarbon group optionally having one or more halogen atoms, etc.; $R^4$ represents a hydrogen atom, etc.; $R^3$, $R^{3a}$, and $R^{3b}$ represent independently of each other a hydrogen atom, etc.; n represents 0, 1, or 2; and p represents 0, 1, 2, or 3] has an excellent efficacy for controlling harmful arthropods.

7 Claims, No Drawings

PYRIMIDINONE COMPOUND

CROSS-REFERENCE TO RELATED APPLICATION

This application is a Section 371 of International Application No. PCT/JP2015/076611, filed Sep. 18, 2015, which was published in the Japanese language on Apr. 7, 2016, under International Publication No. WO 2016/052247 A1, and the disclosure of which is incorporated herein by reference.

TECHNICAL FIELD

The present invention relates to a pyrimidinone compound and use of said compound for controlling harmful arthropods.

BACKGROUND ART

To date, some compounds for controlling harmful arthropods have been developed and come into practical use.

Also, a certain class of pyrimidine compounds has been known (see Patent Document 1).

CITATION LIST

Patent Document

Patent Document 1: JP 6-220023 A

SUMMARY OF THE INVENTION

Problems to be Solved by Invention

An object of the present invention is to provide a compound having an excellent efficacy for controlling harmful arthropods and a method for controlling harmful arthropods using said compound.

Means to Solve Problems

The present inventors have studied to solve the above problems, and found that a pyrimidinone compound represented by the following formula (1) has an excellent efficacy for controlling harmful arthropods.
[1] A pyrimidinone compound represented by formula (1):

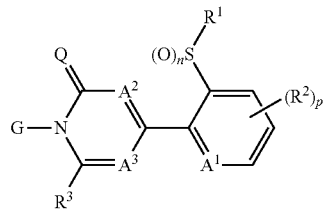

(1)

[wherein:
A$^1$ represents a nitrogen atom or a CR$^4$;
A$^2$ represents a nitrogen atom and A$^3$ represents a CR$^{3b}$, or A$^2$ represents a CR$^{3a}$ and A$^3$ represents a nitrogen atom;
Q represents an oxygen atom or a sulfur atom;
G represents a C2-C10 haloalkyl group, a C3-C10 haloalkenyl group, a C3-C10 haloalkynyl group, a (C1-C5 alkyl)-O—(C2-C5 alkyl) group having one or more halogen atoms, a (C3-C5 alkenyl)-O—(C2-C5 alkyl) group having one or more halogen atoms, a (C3-C5 alkynyl)-O—(C2-C5 alkyl) group having one or more halogen atoms, a (C1-C5 alkyl)-S(O)$_m$—(C2-C5 alkyl) group having one or more halogen atoms, a (C3-C5 alkenyl)-S(O)$_m$—(C2-C5 alkyl) group having one or more halogen atoms, a (C3-C5 alkynyl)-S(O)$_m$—(C2-C5 alkyl) group having one or more halogen atoms, or a (C1-C5 alkyl)-C(O)—(C1-C5 alkyl) group having one or more halogen atoms;
R$^1$ represents a C1-C6 chain hydrocarbon group optionally having one or more halogen atoms;
R$^2$ represents a C1-C6 chain hydrocarbon group optionally having one or more halogen atoms, a phenyl group optionally having one or more atoms or groups selected from Group A, a 5 membered aromatic heterocyclic group selected from Group B (wherein said 5 membered aromatic heterocyclic group may optionally have one or more atoms or groups selected from Group A), a 6 membered aromatic heterocyclic group selected from Group C (wherein said 6 membered aromatic heterocyclic group may optionally have one or more atoms or groups selected from Group A), a 3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group), a OR$^7$, a NR$^8$R$^9$, a NR$^8$C(O)R$^{10}$, a NR$^8$C(O)OR$^{11}$, a NR$^8$C(O)NR$^{12}$R$^{13}$, a N=CHNR$^{12}$R$^{13}$, a N=S(O)$_x$R$^{12}$R$^{13}$, a S(O)$_y$R$^{12}$, a C(O)OR$^8$, a cyano group, or a halogen atom;
R$^4$ represents a hydrogen atom or a halogen atom;
R$^3$, R$^{3a}$, and R$^{3b}$ represent independently of each other a hydrogen atom, a C1-C3 alkyl group optionally having one or more halogen atoms, or a halogen atom;
R$^7$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a (C1-C3 alkyl)-O—(C1-C3 alkyl) group optionally having one or more halogen atoms, a (C1-C3 alkyl)-S(O)$_y$—(C1-C3 alkyl) group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group (wherein the phenyl moiety in said phenyl C1-C3 alkyl group may optionally have one or more atoms or groups selected from Group A);
R$^8$ represents a hydrogen atom, a C1-C6 alkyl group optionally having one or more halogen atoms, a C3-C6 alkenyl group optionally having one or more halogen atoms, or a C3-C6 alkynyl group optionally having one or more halogen atoms;
R$^9$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a (C1-C3 alkyl)-O—(C1-C3 alkyl) group optionally having one or more halogen atoms, a (C1-C3 alkyl)-S(O)$_y$-(C1-C3 alkyl) group optionally having one or more halogen atoms, a C3-C7 cycloalkyl group optionally having one or more halogen atoms, a (C3-C7 cycloalkyl)-(C1-C3 alkyl) group optionally having one or more halogen atoms, a C1-C6 alkyl group having one cyano group, a phenyl C1-C3 alkyl group (wherein the phenyl moiety in said phenyl C1-C3 alkyl group may optionally have one or more atoms or groups selected from Group A), or a (5 or 6 membered heteroaryl)C1-C6 alkyl group (wherein the 5 or 6 membered heteroaryl moiety in said (5 or 6 membered heteroaryl)C1-C6 alkyl group may optionally have one or more atoms or groups selected from Group A);

$R^{10}$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group (wherein the phenyl moiety in said phenyl C1-C3 alkyl group may optionally have one or more atoms or groups selected from Group A);

$R^{11}$ represents a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group (wherein the phenyl moiety in said phenyl C1-C3 alkyl group may optionally have one or more atoms or groups selected from Group A);

$R^{12}$ and $R^{13}$ represent independently of each other a C1-C6 alkyl group optionally having one or more halogen atoms;

$R^{14}$ represents a hydrogen atom, a C1-C6 alkyl group optionally having one or more halogen atoms, a C2-C6 alkylcarbonyl group optionally having one or more halogen atoms, or a C2-C6 alkoxycarbonyl group optionally having one or more halogen atoms;

n represents 0, 1, or 2;
m represents 0, 1, or 2;
p represents 0, 1, 2, or 3 (wherein when p represents 2 or 3, each $R^2$ may be identical or different);
x represents 0 or 1;
y represents 0, 1, or 2;

Group A: a group consisting of a C1-C6 alkyl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a cyano group, and a halogen atom;

Group B:

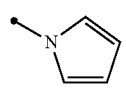

B-1

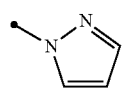

B-2

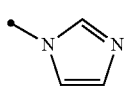

B-3

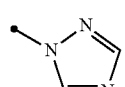

B-4

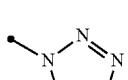

B-5

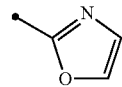

B-6

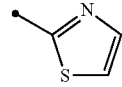

B-7

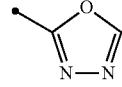

B-8

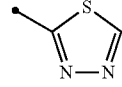

B-9

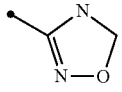

B-10

Group C:

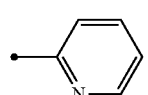

C-1

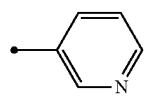

C-2

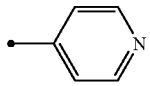

C-3

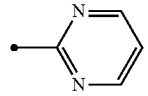

C-4

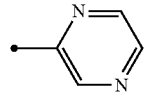

C-5

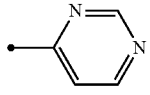

C-6

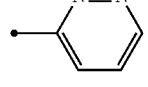

C-7

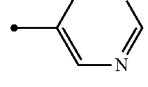

C-8

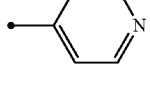

C-9

Group D:

D-1: —N◁

D-2: —N◇ (azetidine)

D-3: —N⬠ (pyrrolidine)

D-4: —N⬡ (piperidine)

D-5: —N(morpholine with O)

D-6: —N(thiomorpholine with S)

D-7: —N⌒N—R$^{14}$ (piperazine)

D-8: —N(azepane, 7-membered)

] (hereinafter, the pyrimidinone compound represented by formula (1) is referred to as "the compound of the present invention").

[2] The compound according to [1] wherein A$^2$ is a nitrogen atom and A$^3$ is a CR$^{3b}$.

[3] The compound according to [1] wherein A$^2$ is a CR$^{3a}$ and A$^3$ is a nitrogen atom.

[4] The compound according to any one of [1] to [3] wherein
G is a C2-C10 haloalkyl group or a C3-C10 haloalkenyl group;
R$^1$ is a C1-C6 alkyl group optionally having one or more halogen atoms;
R$^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;
R$^3$, R$^{3a}$, R$^{3b}$, and R$^4$ are each a hydrogen atom; and
p is 0 or 1.

[5] The compound according to any one of [1] to [3] wherein
G is a C3-C6 alkyl group having three or more fluorine atoms;
R$^1$ is an ethyl group;
R$^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;
R$^3$, R$^{3a}$, R$^{3b}$, and R$^4$ are each a hydrogen atom; and
p is 0 or 1.

[6] A composition for controlling a harmful arthropod comprising the compound according to any one of [1] to [5] and an inert carrier.

[7] A method for controlling a harmful arthropod which comprises applying an effective amount of the compound according to any one of [1] to [5] to a harmful arthropod or a habitat where a harmful arthropod lives.

MODE FOR CARRYING OUT THE INVENTION

The group(s) as described herein is/are explained as follows by means of examples.

The expression of "optionally having one or more atoms or groups selected from Group A" as described herein represents that when two or more atoms or groups selected from Group A are present, these atoms or groups may be identical to or different from each other.

The expression of "optionally having one or more halogen atoms" as described herein represents that when two or more halogen atoms are present, these halogen atoms may be identical to or different from each other.

The expression of "having one or more halogen atoms" as described herein represents that when two or more halogen atoms are present, these halogen atoms may be identical to or different from each other.

The term of "heterocyclic group" as used in the present invention represents a group containing one or more heteroatoms selected from the group consisting of a nitrogen atom, an oxygen atom, and a sulfur atom as a ring constituent atom other than carbon atoms, and includes aromatic heterocyclic groups and nonaromatic heterocyclic groups.

Examples of the term of "aromatic heterocyclic group" include
5 membered aromatic heterocyclic groups such as 2-furyl group, 3-furyl group, 2-thienyl group, 3-thienyl group, 3-pyrazolyl group, 4-pyrazolyl group, 5-pyrazolyl group, 1-pyrrolyl group, 1-pyrazolyl group, 1-imidazolyl group, and 1,2,4-triazol-1-yl group; and
6 membered aromatic heterocyclic groups such as 2-pyridyl group, 3-pyridyl group, and 4-pyridyl group in which a carbon atom of the heterocyclic group is attached to the rest of the molecule, such as 2-pyridyl group, 3-pyridyl group, and 4-pyridyl group.

Examples of the term of "nonaromatic heterocyclic group" include nonaromatic heterocyclic groups such as aziridin-1-yl group, azetidin-1-yl group, pyrrolidin-1-yl group, 3,3,4,4-tetrafluoropyrrolidin-1-yl group, tetrahydrofuran-2-yl group, tetrahydrofuran-3-yl group, piperidin-1-yl group, morpholin-4-yl group, thiomorpholin-4-yl group, and azepan-1-yl group.

The term of "5 or 6 membered heteroaryl" as used in the present invention represents a 5 membered aromatic heterocyclic group or a 6 membered aromatic heterocyclic group.

Examples of the term of "C2-C10 haloalkyl group" as used in the compound of the present invention include 2-fluoroethyl group, 2,2-difluoroethyl group, 2,2,2-trifluoroethyl group, 2,2,2-trichloroethyl group, pentafluoroethyl group, heptafluoroisopropyl group, 2,2,3,3-tetrafluoropropyl group, 2,2,3,3,3-pentafluoropropyl group, and 2,2,3,4,4,4-hexafluorobutyl group.

Examples of the term of "C3-C10 haloalkenyl group" as used in the compound of the present invention include 3,3-difluoro-2-propenyl group, 3,3-difluoro-2-propenyl group, and 4,4-difluoro-3-butenyl group.

Examples of the term of "C3-C10 haloalkynyl group" as used in the compound of the present invention include 3-chloro-2-propynyl group, 3-fluoro-2-propynyl group, and 4,4,4-trifluoro-2-butynyl group.

The term of "(C1-C5 alkyl)-O—(C2-C5 alkyl) group having one or more halogen atoms" as used in the present invention represents a group having one or more halogen atoms in the C1-C5 alkyl moiety and/or the C2-C5 alkyl moiety, and includes, for example, 2-(2,2,2-trifluoroethoxy)ethyl group and 1,1,1-trifluoro-3-methoxypropan-2-yl group.

Examples of the term of "(C1-C5 alkyl)-O—(C2-C5 alkyl) group" include 2-methoxyethyl group and 2-ethoxyethyl group.

The term of "(C3-C5 alkenyl)-O—(C2-C5 alkyl) having one or more halogen atoms" as used in the present invention represents a group having one or more halogen atoms in the C3-C5 alkenyl moiety and/or the C2-C5 alkyl moiety, and includes, for example, 2-(3,3-difluoro-2-propenyloxy)ethyl group.

Examples of the term of "(C3-C5 alkenyl)-O—(C2-C5 alkyl) group" include 2-(2-propenyl)oxyethyl group.

The term of "(C3-C5 alkynyl)-O—(C2-C5 alkyl) group having one or more halogen atoms" as used in the present invention represents a group having one or more halogen atoms in the C3-C5 alkynyl moiety and/or the C2-C5 alkyl moiety, and includes, for example, 2-(4,4,4-trifluoro-2-butynyloxy)ethyl group.

Examples of the term of "(C3-C5 alkynyl)-O—(C2-C5 alkyl) group" include 2-(2-butynyloxy)ethyl group.

The term of "(C1-C5 alkyl)-S(O)$_m$—(C2-C5 alkyl) group having one or more halogen atoms" as used in the present invention represents a group having one or more halogen atoms in the C1-C5 alkyl moiety and/or the C2-C5 alkyl moiety, and includes, for example, 2-(trifluoromethylthio)ethyl group, 2-(trifluoromethylsulfinyl)ethyl group, 2-(trifluoromethylsulfonyl)ethyl group, 2-(2,2,2-trifluoroethylthio)ethyl group, 2-(2,2,2-trifluoroethanesulfinyl)ethyl group, and 2-(2,2,2-trifluoroethanesulfonyl)ethyl group.

Examples of the term of "(C1-C5 alkyl)-S(O)$_m$—(C2-C5 alkyl) group" include 2-(methylthio)ethyl group and 2-(methylsulfonyl)ethyl group.

The term of "(C3-C5 alkenyl)-S(O)$_m$—(C2-C5 alkyl) group having one or more halogen atoms" as used in the present invention represents a group having one or more halogen atoms in the C3-C5 alkenyl moiety and/or the C2-C5 alkyl moiety, and includes, for example, 2-(3,3-difluoro-2-propenylthio)ethyl group.

Examples of the term of "(C3-C5 alkenyl)-S(O)$_m$—(C2-C5 alkyl) group" include 2-(2-propenylthio)ethyl group.

The term of "(C3-C5 alkynyl)-S(O)$_m$—(C2-C5 alkyl) group having one or more halogen atoms" as used in the present invention represents a group having one or more halogen atoms in the C3-C5 alkynyl moiety and/or the C2-C5 alkyl moiety, and includes, for example, 2-(4,4,4-trifluoro-2-butynylthio)ethyl group.

Examples of the term of "(C3-C5 alkynyl)-S(O)$_m$—(C2-C5 alkyl) group" include 2-(2-butynylthio)ethyl group.

The term of "(C1-C5 alkyl)-C(O)—(C1-C5 alkyl) group having one or more halogen atoms" as used in the present invention represents a group having one or more halogen atoms in any one of the C1-C5 alkyl moieties or both of the C1-C5 alkyl moieties, and includes, for example, 3,3,3-trifluoro-2-oxopropyl group.

Examples of the term of "(C1-C5 alkyl)-C(O)—(C1-C5 alkyl) group" include 2-oxopropyl group and 3,3-dimethyl-2-oxobutyl group.

The term of "(C1-C3 alkyl)-O—(C1-C3 alkyl) group optionally having one or more halogen atoms" as used in the present invention represents a group having one or more halogen atoms in any one of the C1-C3 alkyl moieties or both of the C1-C3 alkyl moieties, and includes, for example, methoxymethyl group, ethoxymethyl group, and 2-(methoxy)ethyl group.

Examples of the term of "C1-C6 chain hydrocarbon group optionally having one or more halogen atoms" as used in the present invention include C1-C6 alkyl groups optionally having one or more halogen atoms such as methyl group, ethyl group, propyl group, isopropyl group, butyl group, isobutyl group, sec-butyl group, tert-butyl group, pentyl group, neopentyl group, hexyl group, trifluoromethyl group, trichloromethyl group, 2-fluoroethyl group, 2,2-difluoroethyl group, 2,2,2-trifluoroethyl group, and pentafluoroethyl group;

C2-C6 alkenyl groups optionally having one or more halogen atoms such as vinyl group, 1-propenyl group, 2-propenyl group, 1-methylvinyl group, 2-methyl-1-propenyl group, 1-butenyl group, 2-butenyl group, 3-butenyl group, 1-pentenyl group, 1-hexenyl group, 1,1-difluoroallyl group, and pentafluoroallyl group; and C2-C6 alkynyl groups optionally having one or more halogen atoms such as ethynyl group, propargyl group, 2-butynyl group, 3-butynyl group, 1-pentynyl group, 1-hexynyl group, and 4,4,4-trifluoro-2-butynyl group.

Examples of the term of "phenyl group optionally having one or more atoms or groups selected from Group A" as used in the present invention include phenyl group, 2-fluorophenyl group, 4-fluorophenyl group, 2,3-difluorophenyl group, 2,3,4,5,6-pentafluorophenyl group, 4-chlorophenyl group, 4-bromophenyl group, 4-iodophenyl group, 4-(trifluoromethyl)phenyl group, 4-(trifluoromethoxy)phenyl group, 4-(trifluoromethylsulfanyl)phenyl group, 4-cyanophenyl group, 4-(methylsulfinyl)phenyl group, and 4-(methylsulfonyl)phenyl group.

Examples of the term of "5 membered aromatic heterocyclic group selected from Group B (wherein said 5 membered aromatic heterocyclic group may optionally have one or more atoms or groups selected from Group A)" as used in the present invention include pyrrol-1-yl group, 2-chloropyrrol-1-yl group, pyrazol-1-yl group, 3-(trifluoromethyl)pyrazol-1-yl group, 4-chloroimidazol-1-yl group, 1,2,4-triazol-1-yl group, 3-methoxy-1,2,4-triazol-1-yl group, 3-methylthio-1,2,4-triazol-1-yl group, 1,2,3-triazol-1-yl group, oxazol-2-yl group, thiazol-2-yl group, 1,3,4-oxadiazol-2-yl group, 1,3,4-thiadiazol-2-yl group, and 1,2,4-oxadiazol-3-yl group.

Examples of the term of "6 membered aromatic heterocyclic group selected from Group C (wherein said 6 membered aromatic heterocyclic group may optionally have one or more atoms or groups selected from Group A)" as used in the present invention include pyridin-2-yl group, pyridin-3-yl group, pyridin-4-yl group, 4-trifluoromethylpyridin-2-yl group, 2-chloropyridin-5-yl group, pyrimidin-2-yl group, pyrazin-2-yl group, pyrimidin-4-yl group, pyridazin-3-yl group, pyrimidin-5-yl group, and pyridazin-4-yl group.

Examples of the term of "3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group" as used in the present invention include aziridin-1-yl group, azetidin-1-yl group, pyrrolidin-1-yl group, 3,3,4,4-tetrafluoropyrrolidin-1-yl group, piperidin-1-yl group, 4,4-dimethylpiperidin-1-yl group, and azepan-1-yl group.

Examples of the term of "C3-C7 cycloalkyl group optionally having one or more halogen atoms" as used in the present invention include cyclopropyl group, 2,2-difluorocyclopropan-1-yl group, cyclobutanyl group, cyclopentanyl group, cyclohexyl group, and cycloheptanyl group.

Examples of the term of "C3-C7 cycloalkyl group" as used in the present invention include cyclopropyl group, cyclopentanyl group, cyclohexyl group, and cycloheptanyl group.

The term of "(C3-C7 cycloalkyl)-(C1-C3 alkyl) group optionally having one or more halogen atoms" as used in the present invention represents a group having one or more halogen atoms in the C3-C7 cycloalkyl moiety, and includes, for example, cyclopropylmethyl group, 2-(cyclopropyl)ethyl group, (2,2-difluorocyclopropyl)methyl group, and cyclopentylmethyl group.

Examples of the term of "(C3-C7 cycloalkyl)-(C1-C3 alkyl) group" as used in the present invention include cyclopropylmethyl group, 2-(cyclopropyl)ethyl group, and cyclopentylmethyl group.

Examples of the term of "phenyl C1-C3 alkyl group (wherein the phenyl moiety in said phenyl C1-C3 alkyl group may optionally have one or more atoms or groups selected from Group A)" as used in the present invention include benzyl group, 2-fluorobenzyl group, 4-chlorobenzyl group, 4-(trifluoromethyl)benzyl group, and 2-(4-(trifluoromethyl)phenyl)ethyl group.

Examples of the term of "(5 or 6 membered heteroaryl) C1-C6 alkyl group (wherein the 5 or 6 membered heteroaryl moiety in said (5 or 6 membered heteroaryl)C1-C6 alkyl group may optionally have one or more atoms or groups selected from Group A)" as used in the present invention include (5 membered heteroaryl)C1-C6 alkyl groups such as (1-methylpyrrol-3-yl)methyl group, (oxazol-2-yl)methyl group, (tetrahydrofuran-3-yl)methyl group, (tetrahydrofuran-2-yl)methyl group, 2-(1,2,4-triazol-1-yl)ethyl group, and (2-chlorothiazol-5-yl)methyl group; and (6 membered heteroaryl)C1-C6 alkyl groups such as (pyridin-2-yl)methyl group, (pyridin-4-yl)methyl group, (pyrimidin-2-yl)methyl group, (pyrimidin-4-yl)methyl group, 2-(2-chloropyridin-5-yl)ethyl group, and [2-(trifluoromethyl)pyridin-2-yl]methyl group.

The term of "halogen atom" as used in the present invention represents fluorine atom, chlorine atom, bromine atom, and iodine atom.

Examples of the term of "C2-C6 alkoxycarbonyl group" as used in the present invention include methoxycarbonyl group and ethoxycarbonyl group.

Examples of the term of "C1-C6 alkoxy group optionally having one or more halogen atoms" as used in the present invention include trifluoromethoxy group and 2,2,2-trifluoroethoxy group.

The term of "(C1-C3 alkyl)-S(O)$_y$—(C1-C3 alkyl) group optionally having one or more halogen atoms" as used in the present invention represents a group optionally having one or more halogen atoms in the C1-C3 alkyl moiety and/or the C1-C3 alkyl moiety, and includes, for example, methylthiomethyl group, trifluoromethylthiomethyl group, methanesulfinylmethyl group, trifluoromethanesulfonylmethyl group, methanesulfonylmethyl group, 2-(methylthio)ethyl group, and ethylthiomethyl group.

Examples of the term of "(C1-C3 alkyl)-S(O)$_y$—(C1-C3 alkyl) group" as used in the present invention include methylthiomethyl group, methanesulfinylmethyl group, methanesulfonylmethyl group, 2-(methylthio)ethyl group, and ethylthiomethyl group.

The term of "C1-C6 fluoroalkyl group" as used in the present invention represents a C1-C6 alkyl group having one or more fluorine atoms, and includes, for example, fluoromethyl group, trifluoromethyl group, and 2,2,2-trifluoroethyl group.

Examples of the compound of the present invention include the following compounds.

A compound of formula (1) wherein n is 0, 1, or 2;
A compound of formula (1) wherein n is 0;
A compound of formula (1) wherein n is 1;
A compound of formula (1) wherein n is 2;
A compound of formula (1) wherein p is 0, 1, 2, or 3;
A compound of formula (1) wherein p is 0 or 1;
A compound of formula (1) wherein p is 0;
A compound of formula (1) wherein $A^1$ is a nitrogen atom;
A compound of formula (1) wherein $A^1$ is a $CR^4$;
A compound of formula (1) wherein $A^1$ is a CH;
A compound of formula (1) wherein $A^1$ is a nitrogen atom or a CH;
A compound of formula (1) wherein $A^2$ is a nitrogen atom and $A^3$ is a $CR^{3b}$;
A compound of formula (1) wherein $A^2$ is a $CR^{3a}$ and $A^3$ is a nitrogen atom;
A compound of formula (1) wherein $A^2$ is a nitrogen atom and $A^3$ is a CH;
A compound of formula (1) wherein $A^2$ is a CH and $A^3$ is a nitrogen atom;
A compound of formula (1) wherein $A^1$ is a nitrogen atom, $A^2$ is a nitrogen atom, and $A^3$ is a $CR^{3b}$;
A compound of formula (1) wherein $A^1$ is a nitrogen atom, $A^2$ is a $CR^{3a}$, and $A^3$ is a nitrogen atom;
A compound of formula (1) wherein $A^1$ is a $CR^4$, $A^2$ is a nitrogen atom, and $A^3$ is a $CR^{3b}$;
A compound of formula (1) wherein $A^1$ is a $CR^4$, $A^2$ is a $CR^{3a}$ and $A^3$ is a nitrogen atom;
A compound of formula (1) wherein $A^1$ is a CH, $A^2$ is a nitrogen atom, and $A^3$ is a $CR^{3b}$;
A compound of formula (1) wherein $A^1$ is a CH, $A^2$ is a $CR^{3a}$, and $A^3$ is a nitrogen atom;
A compound of formula (1) wherein $A^1$ is a nitrogen atom or a CH, $A^2$ is a nitrogen atom, and $A^3$ is a CH;
A compound of formula (1) wherein $A^1$ is a nitrogen atom or a CH, $A^2$ is a CH, and $A^3$ is a nitrogen atom;
A compound of formula (1) wherein Q is an oxygen atom, $A^1$ is a nitrogen atom, $A^2$ is a nitrogen atom, and $A^3$ is a $CR^{3b}$;

A compound of formula (1) wherein Q is an oxygen atom, $A^1$ is a nitrogen atom, $A^2$ is a $CR^{3a}$, and $A^3$ is a nitrogen atom;

A compound of formula (1) wherein Q is an oxygen atom, $A^1$ is a $CR^4$, $A^2$ is a nitrogen atom, and $A^3$ is a $CR^{3b}$;

A compound of formula (1) wherein Q is an oxygen atom, $A^1$ is a $CR^4$, $A^2$ is a $CR^{3a}$, and $A^3$ is a nitrogen atom;

A compound of formula (1) wherein Q is an oxygen atom or a sulfur atom, $A^1$ is a nitrogen atom, $A^2$ is a nitrogen atom, and $A^3$ is a $CR^{3b}$;

A compound of formula (1) wherein Q is an oxygen atom or a sulfur atom, $A^1$ is a nitrogen atom, $A^2$ is a $CR^{3a}$, and $A^3$ is a nitrogen atom;

A compound of formula (1) wherein Q is an oxygen atom or a sulfur atom, $A^1$ is a $CR^4$, $A^2$ is a nitrogen atom, and $A^3$ is a $CR^{3b}$;

A compound of formula (1) wherein Q is an oxygen atom or a sulfur atom, $A^1$ is a $CR^4$, $A^2$ is a $CR^{3a}$, and $A^3$ is a nitrogen atom;

A compound of formula (1) wherein Q is an oxygen atom;

A compound of formula (1) wherein Q is a sulfur atom;

A compound of formula (1) wherein Q is an oxygen atom or a sulfur atom;

A compound of formula (1) wherein G is a C2-C10 haloalkyl group, a C3-C10 haloalkenyl group, or a C3-C10 haloalkynyl group;

A compound of formula (1) wherein G is a C2-C10 haloalkyl group or a C3-C10 haloalkenyl group;

A compound of formula (1) wherein G is a C2-C10 fluoroalkyl group or a C3-C10 fluoroalkenyl group;

A compound of formula (1) wherein G is a C2-C10 alkyl group having two or more fluorine atoms;

A compound of formula (1) wherein G is a C3-C6 alkyl group having three or more fluorine atoms;

A compound of formula (1) wherein G is a C3-C6 alkyl group having four or more fluorine atoms;

A compound of formula (1) wherein G is a 2,2,2-trifluoroethyl group, a 2,2,3,3-tetrafluoropropyl group, a 2,2,3,3,3-pentafluoropropyl group, a 4,4,4-trifluorobutyl group, a 2,2,3,4,4,4-hexafluorobutyl group, a 3,3,4,4,4-pentafluorobutyl group, a 3,3,4,4,5,5,5-hexafluoropentyl group, a 2,2,3,3,4,4,5,5-octafluoropentyl group, a 3,3-dichloro-2-propenyl group, or a 3,4,4-trifluoro-3-butenyl group;

A compound of formula (1) wherein $R^1$ is a C1-C6 alkyl group or a C1-C6 haloalkyl group;

A compound of formula (1) wherein R is a C1-C6 alkyl group;

A compound of formula (1) wherein $R^1$ is a methyl group, an ethyl group, a propyl group, an isopropyl group, a trifluoromethyl group, or a 2,2,2-trifluoroethyl group;

A compound of formula (1) wherein $R^1$ is an ethyl group;

A compound of formula (1) wherein $R^2$ is a C1-C6 alkyl group optionally having one or more halogen atoms;

A compound of formula (1) wherein $R^2$ is a 5 membered aromatic heterocyclic group selected from Group B (wherein said 5 membered aromatic heterocyclic group may optionally have one or more atoms or groups selected from Group A) or a 6 membered aromatic heterocyclic group selected from Group C (wherein said 6 membered aromatic heterocyclic group may optionally have one or more atoms or groups selected from Group A);

A compound of formula (1) wherein $R^2$ is a 5 membered aromatic heterocyclic group selected from Group B (wherein said 5 membered aromatic heterocyclic group may optionally have one or more atoms or groups selected from Group A);

A compound of formula (1) wherein $R^2$ is a 5 membered aromatic heterocyclic group selected from Group B (wherein said 5 membered aromatic heterocyclic group may optionally have one or more atoms or groups selected from Group A) or a 3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group);

A compound of formula (1) wherein $R^2$ is a 3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group);

A compound of formula (1) wherein $R^2$ is a $OR^7$, a cyano group, or a halogen atom;

A compound of formula (1) wherein $R^2$ is a $OR^7$;

A compound of formula (1) wherein $R^2$ is a $NR^8R^9$, a $NR^8C(O)R^{10}$, a $NR^8C(O)OR^{11}$, a $NR^8C(O)NR^{12}R^{13}$, a $N=CHNR^{12}R^{13}$, or a $N=S(O)_xR^{12}R^{13}$;

A compound of formula (1) wherein $R^2$ is a $NR^8R^9$;

A compound of formula (1) wherein $R^2$ is a C1-C6 alkyl group optionally having one or more halogen atoms, a $OR^7$, or a $NR^8R^9$;

A compound of formula (1) wherein $R^2$ is a C1-C6 alkyl group optionally having one or more halogen atoms, a 3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group), a $OR^7$, or a $NR^8R^9$;

A compound of formula (1) wherein $R^2$ is a C1-C6 alkyl group optionally having one or more halogen atoms, a 5 membered aromatic heterocyclic group selected from Group B (wherein said 5 membered aromatic heterocyclic group may optionally have one or more atoms or groups selected from Group A), a 6 membered aromatic heterocyclic group selected from Group C (wherein said 6 membered aromatic heterocyclic group may optionally have one or more atoms or groups selected from Group A), a 3 to 7 membered nonaromatic heterocyclic group selected from Group D (wherein said 3 to 7 membered nonaromatic heterocyclic group may optionally have one or more atoms or groups selected from the group consisting of a halogen atom and a C1-C6 alkyl group), a $OR^7$, or a $NR^8R^9$;

A compound of formula (1) wherein

G is a C2-C10 haloalkyl group or a C3-C10 haloalkenyl group;

$R^1$ is a C1-C6 alkyl group optionally having one or more halogen atoms;

$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkylmoietyin said (C1-C6 alkyl)amino group may optionally have one or more atoms or groups selected from the group consisting of one or more halogen atoms and a 5 membered aromatic heterocyclic group optionally having one or more halogen atoms), or an amino group;

$R^3$, $R^{3a}$, $R^{3b}$, and $R^4$ are each a hydrogen atom; and p is 0 or 1;

A compound of formula (1) wherein

G is a C3-C6 alkyl group having three or more fluorine atoms;

$R^1$ is an ethyl group;

$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;

$R^3$, $R^{3a}$, $R^{3b}$, and $R^4$ are each a hydrogen atom;

p is 0 or 1;

A compound of formula (1) wherein

G is a C2-C10 haloalkyl group or a C3-C10 haloalkenyl group;

$R^1$ is a C1-C6 alkyl group optionally having one or more halogen atoms;

$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more atoms or groups selected from Group B), a nonaromatic heterocyclic group selected from the group consisting of D-1 group to D-8 group (wherein said nonaromatic heterocyclic group may optionally have one or more atoms or groups selected from Group D), a C1-C6 alkoxy group optionally having one or more halogen atoms, a di (C1-C6 alkyl)amino group optionally having one or more halogen atoms, a (C1-C6 alkyl)amino group (wherein the C1-C6 alkyl moiety in said (C1-C6 alkyl)amino group may optionally have one or more halogen atoms), or an amino group;

$R^3$, $R^{3a}$, $R^{3b}$, and $R^4$ are each a hydrogen atom; and p is 0 or 1; and A compound of formula (1) wherein G is a C2-C10 haloalkyl group or a C3-C10 haloalkenyl group;

$R^1$ is a C1-C6 alkyl group;

p is 0 or 1;

$R^2$ is a C1-C6 alkyl group optionally having one or more halogen atoms, a 1,2,4-triazol-1-yl group optionally having one or more halogen atoms, a pyrrolidin-1-yl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group, a (thiazol-5-ylmethyl)amino group optionally having one or more halogen atoms, or an amino group; and $R^{3a}$ is a hydrogen atom or a C1-C3 alkyl group.

Formula (1-1)

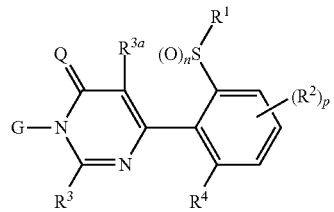

(1-1)

[wherein the symbols are the same as defined above.]

A compound of formula (1-1) wherein

G is a C2-C6 haloalkyl group, a C3-C10 haloalkenyl group, or a C3-C10 haloalkynyl group;

$R^1$ is a C1-C6 alkyl group optionally having one or more halogen atoms;

$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;

$R^3$ and $R^{3a}$ are independently of each other a hydrogen atom or a C1-C3 alkyl group;

$R^4$ is a hydrogen atom; and p is 0 or 1.

A compound of formula (1-1) wherein

G is a C2-C10 haloalkyl group or a C3-C10 haloalkenyl group;

$R^1$ is a C1-C6 alkyl group or a C1-C6 haloalkyl group;

$R^2$ is a C1-C6 fluoroalkyl group, a 5 membered aromatic heterocyclic group selected from the group consisting of B-1 group to B-4 group (wherein said 5 membered aromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, an alkylamino group optionally having one or more halogen atoms, a (thiazol-5-ylmethyl)amino group optionally having one or more halogen atoms, or an amino group;

$R^3$ and $R^4$ are each a hydrogen atom; and
$R^{3a}$ is a hydrogen atom or a C1-C3 alkyl group.
A compound of formula (1-1) wherein
Q is an oxygen atom;
G is a C2-C6 haloalkyl;
$R^1$ is a C1-C6 alkyl group;
p is 1;
$R^2$ is a C1-C6 fluoroalkyl group;
$R^3$ and $R^4$ are each a hydrogen atom; and
$R^{3a}$ is a hydrogen atom or a C1-C3 alkyl group.

Formula (1-2)

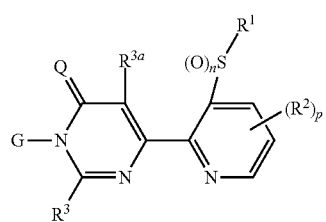

(1-2)

[wherein the symbols are the same as defined above.]

A compound of formula (1-2) wherein
G is a C2-C10 haloalkyl group, a C3-C10 haloalkenyl group, or a C3-C10 haloalkynyl group;
$R^1$ is a C1-C6 alkyl group optionally having one or more halogen atoms;
$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;
$R^3$ and $R^{3a}$ are independently of each other a hydrogen atom or a C1-C3 alkyl group; and
p is 0 or 1.

A compound of formula (1-2) wherein
G is a C2-C10 haloalkyl group or a C3-C10 haloalkenyl group;
$R^1$ is a C1-C6 alkyl group or a C1-C6 haloalkyl group;
$R^2$ is a C1-C6 fluoroalkyl group, a 5 membered aromatic heterocyclic group selected from the group consisting of B-1 group to B-4 group (wherein said 5 membered aromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, an alkylamino group optionally having one or more halogen atoms, a (thiazol-5-ylmethyl)amino group optionally having one or more halogen atoms, or an amino group;
$R^3$ is a hydrogen atom; and
$R^{3a}$ is a hydrogen atom or a C1-C3 alkyl group.

A compound of formula (1-2) wherein
G is a C2-C10 haloalkyl group or a C3-C10 haloalkenyl group;
$R^1$ is a C1-C6 alkyl group;
p is 0 or 1;
$R^2$ is a C1-C6 alkyl group optionally having one or more halogen atoms, a 1,2,4-triazol-1-yl group optionally having one or more halogen atoms, a pyrrolidin-1-yl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group, a (thiazol-5-ylmethyl)amino group optionally having one or more halogen atoms, or an amino group; and
$R^3$ and $R^{3a}$ are each a hydrogen atom.

Formula (1-3)

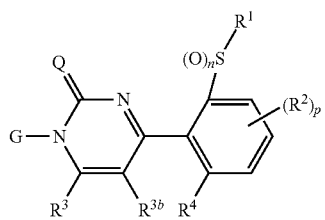

(1-3)

[wherein the symbols are the same as defined above.]

A compound of formula (1-3) wherein
G is a C2-C6 haloalkyl group, a C3-C10 haloalkenyl group, or a C3-C10 haloalkynyl group;
$R^1$ is a C1-C6 alkyl group optionally having one or more halogen atoms;
$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;

$R^3$ and $R^{3b}$ are independently of each other a hydrogen atom or a C1-C3 alkyl group;

$R^4$ is a hydrogen atom; and p is 0 or 1.

A compound of formula (1-3) wherein

G is a C2-C10 haloalkyl group or a C3-C10 haloalkenyl group;

$R^1$ is a C1-C6 alkyl group or a C1-C6 haloalkyl group;

$R^2$ is a C1-C6 fluoroalkyl group, a 5 membered aromatic heterocyclic group selected from the group consisting of B-1 group to B-4 group (wherein said 5 membered aromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, an alkylamino group optionally having one or more halogen atoms, a (thiazol-5-ylmethyl)amino group optionally having one or more halogen atoms, or an amino group;

$R^3$ and $R^4$ are each a hydrogen atom; and $R^{3b}$ is a hydrogen atom or a C1-C3 alkyl group.

Formula (1-4)

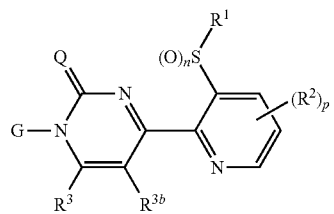

(1-4)

[wherein the symbols are the same as defined above.]

A compound of formula (1-4) wherein

G is a C2-C10 haloalkyl group, a C3-C10 haloalkenyl group, or a C3-C10 haloalkynyl group;

$R^1$ is a C1-C6 alkyl group optionally having one or more halogen atoms;

$R^2$ is a C1-C6 alkyl group optionally having one or more halogen atoms, a 5 membered aromatic heterocyclic group selected from the group consisting of B-1 group to B-4 group (wherein said 5 membered aromatic heterocyclic group may optionally have one or more halogen atoms), a nonaromatic heterocyclic group selected from the group consisting of D-1 group to D-8 group (wherein said nonaromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group (wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms), or an amino group;

$R^3$ and $R^{3b}$ are independently of each other a hydrogen atom or a C1-C3 alkyl group; and p is 0 or 1.

A compound of formula (1-4) wherein

G is a C2-C10 haloalkyl group or a C3-C10 haloalkenyl group;

$R^1$ is a C1-C6 alkyl group or a C1-C6 haloalkyl group;

$R^2$ is a C1-C6 fluoroalkyl group, a 5 membered aromatic heterocyclic group selected from the group consisting of B-1 group to B-4 group (wherein said 5 membered aromatic heterocyclic group may optionally have one or more halogen atoms), a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, an alkylamino group optionally having one or more halogen atoms, a (thiazol-5-ylmethyl)amino group optionally having one or more halogen atoms, or an amino group;

$R^3$ is a hydrogen atom; and $R^{3b}$ is a hydrogen atom or a C1-C3 alkyl group.

A compound of formula (1-4) wherein

Q is an oxygen atom;

G is a C2-C10 haloalkyl group;

$R^1$ is a C1-C6 alkyl group;

p is 0; and $R^3$ and $R^{3b}$ are each a hydrogen atom.

Next, the process for preparing the compound of the present invention is described.

The compound of the present invention and the intermediate compound can be prepared, for example, according to the following (Process 1) to (Process 18).

Process 1

The compound (1b) of the present invention wherein Q is an oxygen atom and n=1 in formula (1) (hereinafter referred to as "Present compound (1b)") and the compound (1c) of the present invention wherein Q is an oxygen atom and n=2 in formula (1) (hereinafter referred to as "Present compound (1c)") may be prepared by reacting the compound (1a) of the present invention wherein Q is an oxygen atom and n=0 in formula (1) (hereinafter referred to as "Present compound (1a)") with an oxidizing agent.

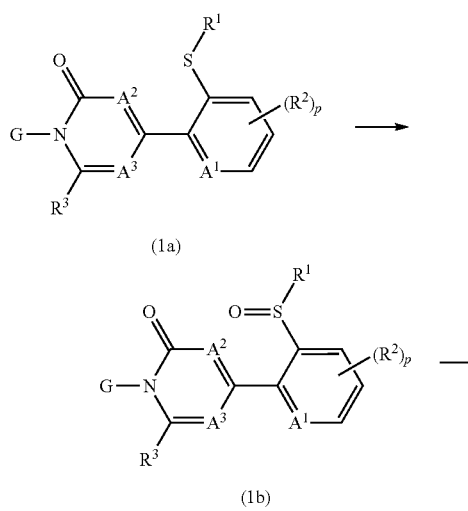

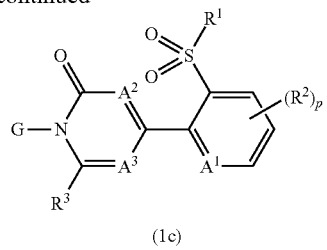

[wherein the symbols are the same as defined in formula (1).]

First, a process for preparing the Present compound (1b) from the Present compound (1a) is described.

The reaction is usually carried out in the presence of a solvent.

Examples of the solvent to be used in the reaction include halogenated aliphatic hydrocarbons such as dichloromethane and chloroform (hereinafter collectively referred to as "halogenated aliphatic hydrocarbons"); nitriles such as acetonitrile (hereinafter collectively referred to as "nitriles"); alcohols such as methanol and ethanol (hereinafter collectively referred to as "alcohols"); acetic acid; water; and mixed solvents thereof.

Examples of the oxidizing agent to be used in the reaction include sodium periodate, m-chloroperbenzoic acid (hereinafter referred to as "mCPBA"), and hydrogen peroxide.

When hydrogen peroxide is used as the oxidizing agent, a base or a catalyst may be added as needed.

Examples of the base to be used in the reaction include sodium carbonate.

Examples of the catalyst to be used in the reaction include tungstic acid and sodium tungstate.

In the reaction, the oxidizing agent is usually used within a range of 1 to 1.2 molar ratio(s), as opposed to 1 mole of the Present compound (1a).

In the reaction, the base is usually used within a range of 0.01 to 1 molar ratio(s), as opposed to 1 mole of the Present compound (1a).

In the reaction, the catalyst is usually used within a range of 0.01 to 0.5 molar ratios, as opposed to 1 mole of the Present compound (1a).

The reaction temperature of the reaction is usually within a range of −20 to 80° C. The reaction period of the reaction is usually within a range of 0.1 to 12 hours.

When the reaction is completed, the reaction mixtures are extracted with organic solvent(s), and the organic layers are washed with an aqueous solution of a reducing agent (such as sodium sulfite and sodium thiosulfate) and an aqueous solution of a base (such as sodium hydrogen carbonate) as needed. The organic layers are dried and concentrated to isolate the Present compound (1b). The isolated Present compound (1b) may be further purified by, for example, chromatography or recrystallization.

Next, a process for preparing the Present compound (1c) from the Present compound (1b) is described.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide. When hydrogen peroxide is used as the oxidizing agent, a base or a catalyst may be added as needed.

Examples of the base to be used in the reaction include sodium carbonate.

Examples of the catalyst to be used in the reaction include sodium tungstate.

In the reaction, the oxidizing agent is usually used within a range of 1 to 4 molar ratio(s), as opposed to 1 mole of the Present compound (1b). Preferably, the oxidizing agent is used within a range of 1 to 2 molar ratio(s), as opposed to 1 mole of the Present compound (1b).

In the reaction, the base is usually used within a range of 0.01 to 1 molar ratio(s), as opposed to 1 mole of the Present compound (1b).

In the reaction, the catalyst is usually used within a range of 0.01 to 0.5 molar ratios, as opposed to 1 mole of the Present compound (1b).

The reaction temperature of the reaction is usually within a range of −20 to 120° C. The reaction period of the reaction is usually within a range of 0.1 to 12 hours.

When the reaction is completed, the reaction mixtures are extracted with organic solvent(s), and the organic layers are washed with an aqueous solution of a reducing agent (such as sodium sulfite and sodium thiosulfate) and an aqueous solution of a base (such as sodium hydrogen carbonate) as needed. The resulting organic layers are dried and concentrated to isolate the Present compound (1c). The Present compound (1c) may be further purified by, for example, chromatography or recrystallization.

Also, the Present compound (1c) may be prepared in one step (one-pot) reaction by reacting the Present compound (1a) with an oxidizing agent.

The reaction is usually carried out in the presence of a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent in the reaction, a base or a catalyst may be added as needed.

Examples of the base to be used in the reaction include sodium carbonate.

Examples of the catalyst to be used in the reaction include tungstic acid and sodium tungstate.

In the reaction, the oxidizing agent is usually used within a range of 2 to 5 molar ratios, as opposed to 1 mole of the Present compound (1a).

In the reaction, the base is usually used within a range of 0.01 to 1 molar ratio(s), as opposed to 1 mole of the Present compound (1a).

In the reaction, the catalyst is usually used within a range of 0.01 to 0.5 molar ratios, as opposed to 1 mole of the Present compound (1a).

The reaction temperature of the reaction is usually within a range of 0 to 120° C. The reaction period of the reaction is usually within a range of 0.1 to 12 hours.

When the reaction is completed, the reaction mixtures are extracted with organic solvent(s), and the organic layers are washed with an aqueous solution of a reducing agent (such as sodium sulfite and sodium thiosulfate) and an aqueous solution of a base (such as sodium hydrogen carbonate) as needed. The organic layers are dried and concentrated to isolate the Present compound (1c). The isolated Present compound (1c) may be further purified by, for example, chromatography or recrystallization.

Process 2

The Present compound (1a) may be prepared by reacting the compound represented by formula (M1) (hereinafter referred to as "Compound (M1)") with the compound represented by formula (R1) (hereinafter referred to as "Compound (R1)") in the presence of a base.

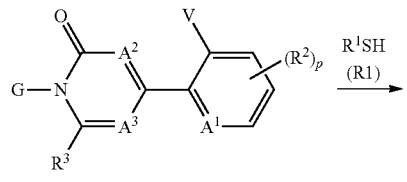

(M1)

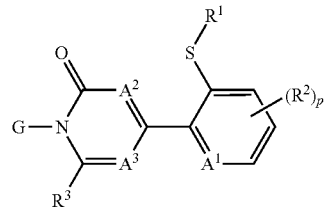

(1a)

[wherein V represents a fluorine atom or a chlorine atom; and the other symbols are the same as defined in formula (1).]

The reaction is usually carried out in the presence of a solvent.

Examples of the solvent to be used in the reaction include ethers such as tetrahydrofuran (hereinafter referred to as "THF"), ethylene glycol dimethyl ether, methyl-tert-butyl ether, and 1,4-dioxane (hereinafter collectively referred to as "ethers"); aromatic hydrocarbons such as toluene and xylene (hereinafter collectively referred to as "aromatic hydrocarbons"); nitriles; aprotic polar solvents such as N,N-dimethylformamide (hereinafter referred to as "DMF"), N-methylpyrrolidone (hereinafter referred to as "NMP"), and dimethyl sulfoxide (hereinafter referred to as "DMSO") (hereinafter collectively referred to as "aprotic polar solvents"); water; and mixed solvents thereof.

Examples of the base to be used in the reaction include alkali metal carbonates such as sodium carbonate and potassium carbonate (hereinafter collectively referred to as "alkali metal carbonates") and alkali metal hydrides such as sodium hydride (hereinafter collectively referred to as "alkali metal hydrides").

In the reaction, the Compound (R1) is usually used within a range of 1 to 10 molar ratio(s), and the base is usually used within a range of 1 to 10 molar ratio(s), as opposed to 1 mole of the Compound (M1). Preferably, the Compound (R1) is used within a range of 1.0 to 1.1 molar ratio(s), and the base is used within a range of 1 to 2 molar ratio(s), as opposed to 1 mole of the Compound (M1).

The reaction temperature of the reaction is usually within a range of $-20°$ C. to $150°$ C. The reaction period of the reaction is usually within a range of 0.5 to 24 hours.

When the reaction is completed, the reaction mixtures are extracted with organic solvent(s), and the organic layers are worked up (for example, dried or concentrated) to isolate the Present compound (1a). The isolated Present compound (1a) may be further purified by, for example, chromatography or recrystallization.

Process 3

The compound of the present invention represented by formula (1z) (hereinafter referred to as "Present compound (1z)") may be prepared by reacting the compound represented by formula (M2) (hereinafter referred to as "Compound (M2)") with the compound represented by formula (R2) (hereinafter referred to as "Compound (R2)") in the presence of a base.

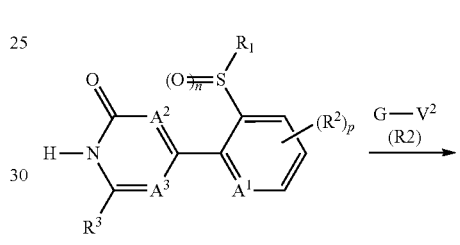

(M2)

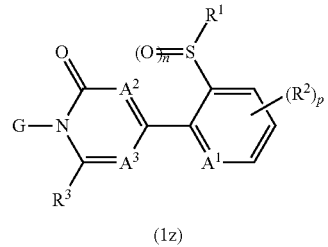

(1z)

[wherein $V^2$ represents a chlorine atom, a bromine atom, an iodine atom, a trifluoromethanesulfonate group, or a nonafluorobutanesulfonate group; and the other symbols are the same as defined in formula (1).]

The reaction is usually carried out in the presence of a solvent.

Examples of the solvent to be used in the reaction include ethers, halogenated aliphatic hydrocarbons, aromatic hydrocarbons, aprotic polar solvents, and mixed solvents thereof.

Examples of the base to be used in the reaction include organic bases such as triethylamine, diisopropylethylamine, pyridine, and 4-dimethylaminopyridine (hereinafter collectively referred to as "organic bases"); alkali metal hydrides; and alkali metal carbonates.

In the reaction, the Compound (R2) is usually used within a range of 1 to 10 molar ratio(s), and the base is usually used within a range of 0.1 to 5 molar ratios, as opposed to 1 mole of the Compound (M2).

The reaction temperature of the reaction is usually within a range of −20° C. to 120° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the compound (1) of the present invention. The isolated compound (1) of the present invention may be further purified by, for example, chromatography or recrystallization.

Process 4

The Compound (M1) may be prepared by reacting the compound represented by formula (M3) (hereinafter referred to as "Compound (M3)") with the Compound (R2) in the presence of a base.

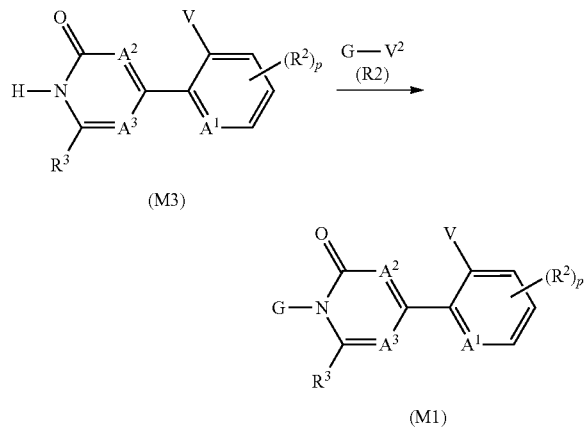

[wherein the symbols are the same as defined above.]

The reaction may be carried out by using the Compound (M3) instead of the Compound (M2) according to the reaction described in the Process 3 to prepare the Compound (M1).

Process 5

The Compound (M2b) wherein n=1 in the Compound (M2) (hereinafter referred to as "Compound (M2b)") and the Compound (M2c) wherein n=2 in the Compound (M2) (hereinafter referred to as "Compound (M2c)") may be prepared by reacting the Compound (M2a) wherein n=0 in the Compound (M2) (hereinafter referred to as "Compound (M2a)") with an oxidizing agent.

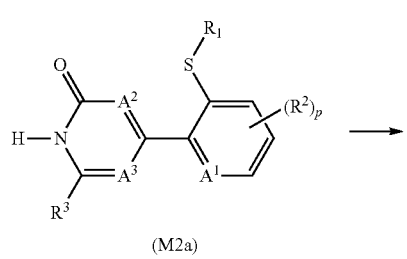

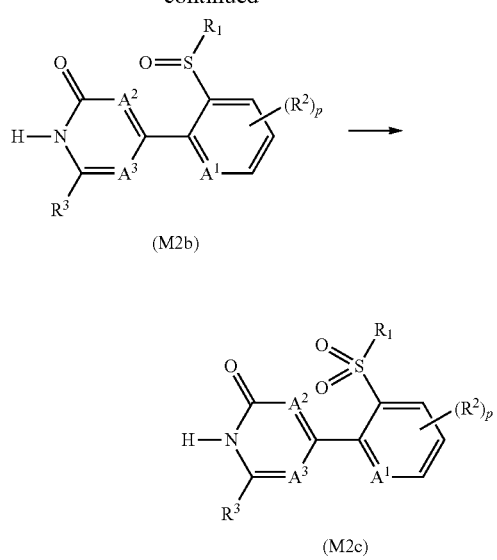

[wherein the symbols are the same as defined in formula (1).]

The reaction may be carried out by using the Compound (M2a) instead of the Present compound (1a) and using the Compound (M2b) instead of the Present compound (1b) according to the reaction described in the Process 1 to prepare the Compound (M2b) and the Compound (M2c).

Process 6

The Compound (M2a) may be prepared by reacting the Compound (M3) with the Compound (R1) in the presence of a base.

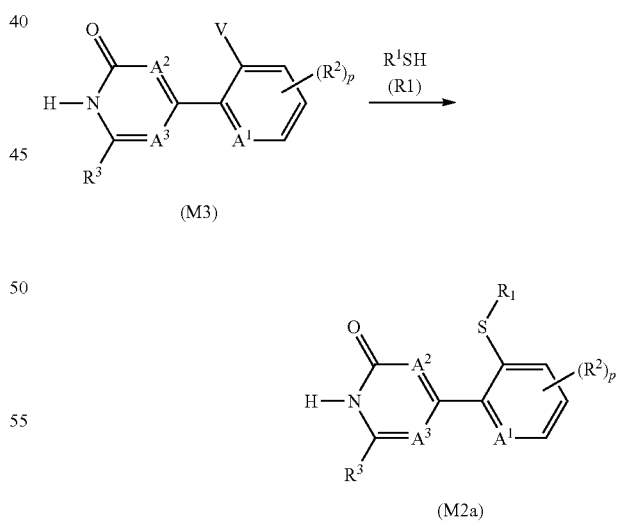

[wherein the symbols are the same as defined above.]

The reaction may be carried out by using the Compound (M3) instead of the Compound (M1) according to the method described in the Process 2 to prepare the Compound (M2a).

Process 7

The Compound (M3) may be prepared according to, for example, the following process.

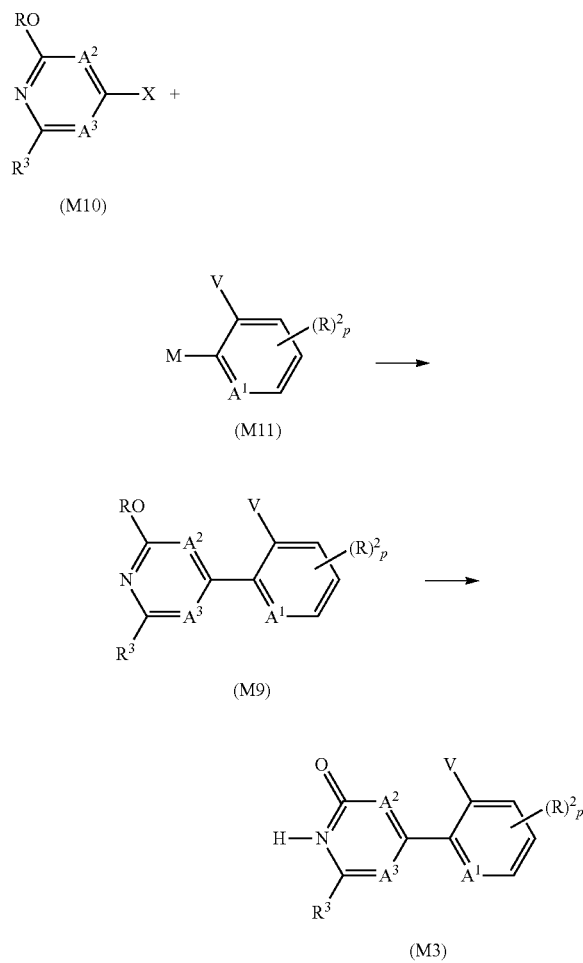

[wherein R represents a C1-C3 alkyl group; M represents a 9-borabicyclo[3.3.1]non-9-yl group, a —B(OH)$_2$ group, a 4,4,5,5-tetramethyl-1,3,2-dioxaborolan-2-yl group, a —SnBu$_3$ group, a —ZnCl group, a —MgCl group, or a —MgBr group; and the other symbols are the same as defined above.]

First, a process for preparing the compound represented by formula (M9) (hereinafter referred to as "Compound (M9)") is described.

The Compound (M9) may be prepared by reacting the compound represented by formula (M10) (hereinafter referred to as "Compound (M10)") with the compound represented by formula (M11) (hereinafter referred to as "Compound (M11)") in the presence of a metal catalyst.

The reaction is usually carried out in the presence of a solvent.

Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphosphino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalysts such as copper(I) iodide and copper(I) chloride.

A ligand, a base, and/or an inorganic halide may be added to the reaction as needed.

Examples of the ligand to be used in the reaction include triphenylphosphine, Xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline. Examples of the base to be used in the reaction include alkali metal hydrides, alkali metal carbonates, and organic bases.

Examples of the inorganic halide to be used in the reaction include alkali metal fluorides such as potassium fluoride and sodium fluoride; and alkali metal chlorides such as lithium chloride and sodium chloride.

In the reaction, the Compound (M11) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halide is usually used within a range of 0.1 to 5 molar ratios, as opposed to 1 mole of the Compound (M10).

The reaction temperature of the reaction is usually within a range of −20° C. to 200° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M9). The isolated Compound (M9) may be further purified by, for example, chromatography or recrystallization.

Next, a process for preparing the Compound (M3) from the Compound (M9) is described.

The Compound (M3) may be prepared by reacting the Compound (M9) in the presence of an acid.

The reaction is carried out in the presence of a solvent.

Examples of the solvent to be used in the reaction include halogenated aliphatic hydrocarbons, aromatic hydrocarbons, nitriles, alcohols, acetic acid, water, and mixed solvents thereof.

Examples of the acid to be used in the reaction include mineral acids such as hydrochloric acid and sulfuric acid; boron compounds such as boron trichloride and boron tribromide; and metal chlorides such as titanium chloride and aluminum chloride.

In the reaction, the acid is usually used within a range of 0.1 to 10 molar ratios, as opposed to 1 mole of the Compound (M9). When the mineral acids such as hydrochloric acid and sulfuric acid are used as an acid in the reaction, the mineral acids may be used also as a solvent.

The reaction temperature of the reaction is usually within a range of −20° C. to 150° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M3). The isolated Compound (M3) may be further purified by, for example, chromatography or recrystallization.

Process 8

The Compound (M2a) may be prepared according to, for example, the following process.

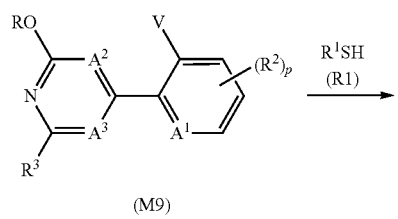

(M9)

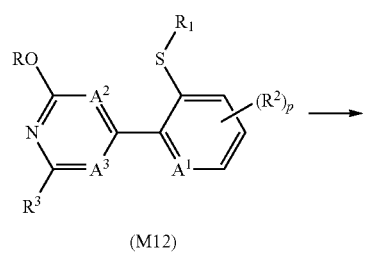

(M12)

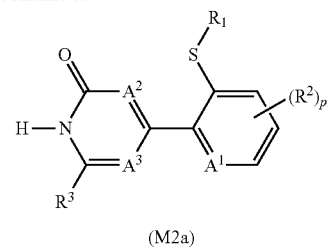

(M2a)

[wherein the symbols are the same as defined above.]

First, a process for preparing the compound represented by formula (M12) (hereinafter referred to as "Compound (M12)") from the Compound (M9) is described.

The Compound (M12) may be prepared by reacting the Compound (M9) with Compound (R1) in the presence of a base.

The reaction may be carried out by using the Compound (M9) instead of the Compound (M1) according to the method described in the Process 2 to prepare the Compound (M12).

Next, a process for preparing the Compound (M2a) from the Compound (M12) is described.

The Compound (M2a) may be prepared by reacting the Compound (M12) in the presence of an acid.

The reaction may be carried out by using the Compound (M12) instead of the Compound (M9) according to the method described in the Process 7 to prepare the Compound (M2a).

Process 9

The Compound (M3-1) wherein $A^2$ is a $CR^{3a}$ and $A^3$ is a nitrogen atom in the Compound (M3) (hereinafter referred to as "Compound (M3-1)") may be prepared according to, for example, the following process.

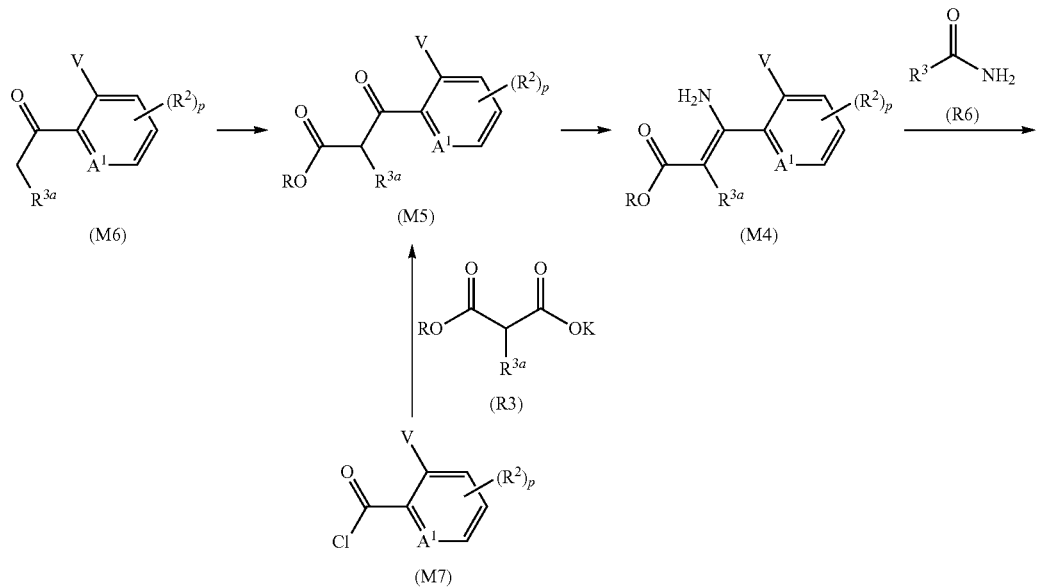

-continued

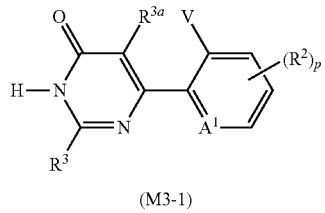

(M3-1)

[wherein the symbols are the same as defined above.]

First, a process for preparing the compound represented by formula (M5) (hereinafter referred to as "Compound (M5)") is described.

The Compound (M5) may be prepared by reacting the compound represented by formula (M6) (hereinafter referred to as "Compound (M6)") with a carbonate ester in the presence of a base.

The reaction is usually carried out in the presence of a solvent.

Examples of the solvent to be used in the reaction include ethers, halogenated aliphatic hydrocarbons, aromatic hydrocarbons, aprotic polar solvents, and mixed solvents thereof.

Examples of the base to be used in the reaction include alkali metal hydrides; alkali metal carbonates; alkali metal alkoxides such as sodium methoxide, sodium ethoxide, and potassium tert-butoxide (hereinafter collectively referred to as "alkali metal alkoxides"); and organic bases.

Examples of the carbonate ester to be used in the reaction include dimethyl carbonate, diethyl carbonate, and dipropyl carbonate.

In the reaction, the carbonate ester is usually used within a range of 1 to 10 molar ratio(s), and the base is usually used within a range of 0.1 to 5 molar ratios, as opposed to 1 mole of the Compound (M6). Also, the carbonate ester may be used also as a solvent.

The reaction temperature of the reaction is usually within a range of $-20°$ C. to $200°$ C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M5). The isolated Compound (M5) may be further purified by, for example, chromatography or recrystallization.

Also, a process for preparing the Compound (M5) from the compound represented by formula (M7) (hereinafter referred to as "Compound (M7)") is described.

The Compound (M5) may also be prepared by reacting the Compound (M7) with the compound represented by formula (R3) (hereinafter referred to as "Compound (R3)") in the presence of magnesium chloride and a base, and then with an acidic aqueous solution.

The reaction is usually carried out in the presence of a solvent.

Examples of the solvent to be used in the reaction include ethers, halogenated aliphatic hydrocarbons, aromatic hydrocarbons, aprotic polar solvents, and mixed solvents thereof.

Examples of the base to be used in the reaction include organic bases.

Examples of the acidic aqueous solution to be used in the reaction include an aqueous solution of a mineral acid such as hydrochloric acid and sulfuric acid.

In the reaction, the Compound (R3) is usually used within a range of 1 to 10 molar ratio(s), the magnesium chloride is usually used within a range of 1 to 10 molar ratio(s), the base is usually used within a range of 0.1 to 10 molar ratios, and the acidic aqueous solution such as a 1N to 12N acidic aqueous solution is used within a range of 1 to 100 molar ratio(s), as opposed to 1 mole of the Compound (M7).

The reaction temperature of the reaction is usually within a range of $-20°$ C. to $200°$ C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M5). The isolated Compound (M5) may be further purified by, for example, chromatography or recrystallization.

Next, a process for preparing the compound represented by formula (M4) (hereinafter referred to as "Compound (M4)") from the Compound (M5) is described.

The Compound (M4) may be prepared by reacting the Compound (M5) with an ammonium salt.

The reaction is usually carried out in the presence of a solvent.

Examples of the solvent to be used in the reaction include ethers, halogenated aliphatic hydrocarbons, aromatic hydrocarbons, nitriles, aprotic polar solvents, nitrogen-containing aromatic compounds, and mixed solvents thereof.

Examples of the ammonium salt to be used in the reaction include ammonium acetate and ammonium chloride.

In the reaction, the ammonium salt is usually used within a range of 1 to 10 molar ratio(s), as opposed to 1 mole of the Compound (M5).

The reaction temperature of the reaction is usually within a range of $-20°$ C. to $200°$ C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M4). The isolated Compound (M4) may be further purified by, for example, chromatography or recrystallization.

Next, a process for preparing the Compound (M3-1) from the Compound (M4) is described.

The Compound (M3-1) may be prepared by reacting the Compound (M4) with the compound represented by formula (R6) (hereinafter referred to as "Compound (R6)") in the presence of a base.

The reaction is usually carried out in the presence of a solvent.

mixtures are collected by filtration, to isolate the Compound (M3-1). The isolated Compound (M3-1) may be further purified by, for example, chromatography or recrystallization.

Process 10

The compound represented by formula (M2a-1) (hereinafter referred to as "Compound (M2a-1)") may be prepared according to, for example, the following process.

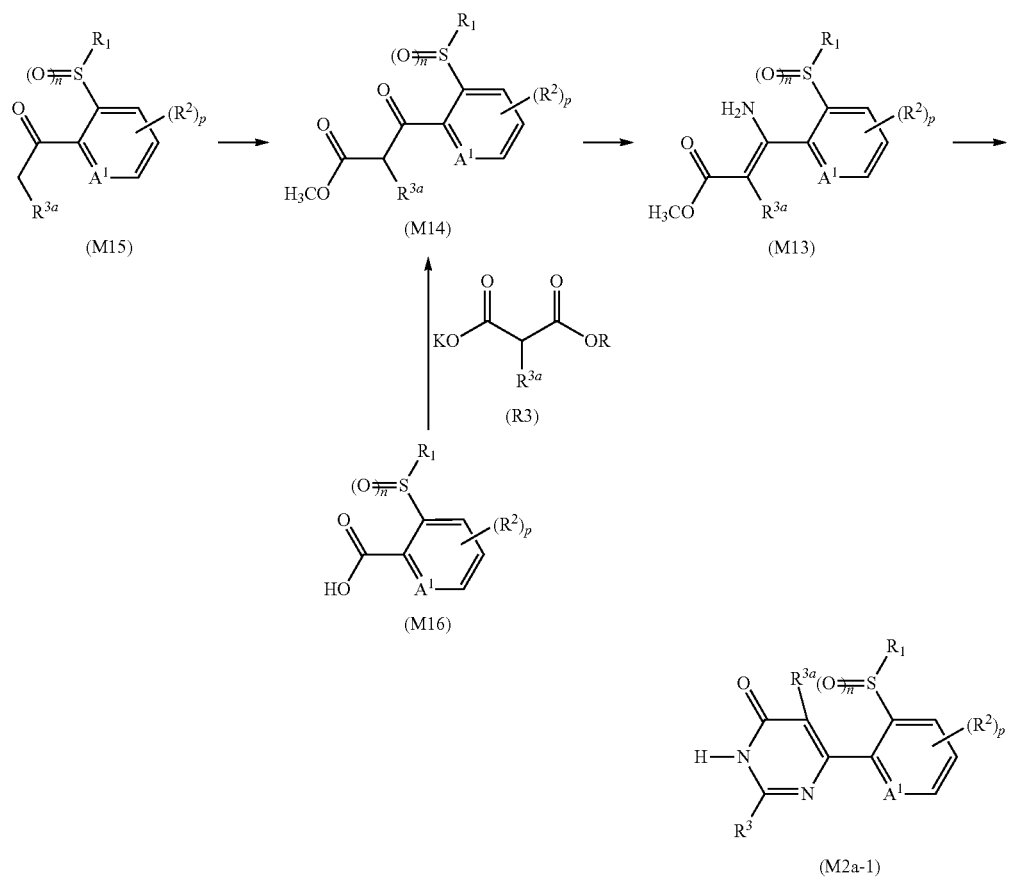

[wherein the symbols are the same as defined above.]

The Compound (M14) may be prepared by using the compound represented by formula (M16) (hereinafter referred to as "Compound (M16)") instead of the Compound (M7) or by using the compound represented by formula (M15) (hereinafter referred to as "Compound (M15)") instead of the Compound (M6) according to the method described in the Process 9.

The compound represented by formula (M13) (hereinafter referred to as "Compound (M13)") may be prepared by using the compound represented by formula (M14) (hereinafter referred to as "Compound (M14)") instead of the Compound (M5) according to the method described in the Process 9.

The Compound (M2a-1) may be prepared by using the Compound (M13) instead of the Compound (M4) according to the method described in the Process 9.

Process 11

The compound represented by formula (M2a-2) (hereinafter referred to as "Compound (M2a-2)") may be prepared according to, for example, the following process.

Examples of the solvent to be used in the reaction include ethers, halogenated aliphatic hydrocarbons, aromatic hydrocarbons, aprotic polar solvents, and mixed solvents thereof.

Examples of the base to be used in the reaction include alkali metal hydrides, alkali metal carbonates, and alkali metal alkoxides.

In the reaction, the Compound (R6) is usually used within a range of 1 to 10 molar ratio(s), and the base is usually used within a range of 1 to 10 molar ratio(s), as opposed to 1 mole of the Compound (M4).

The reaction temperature of the reaction is usually within a range of −20° C. to 200° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction

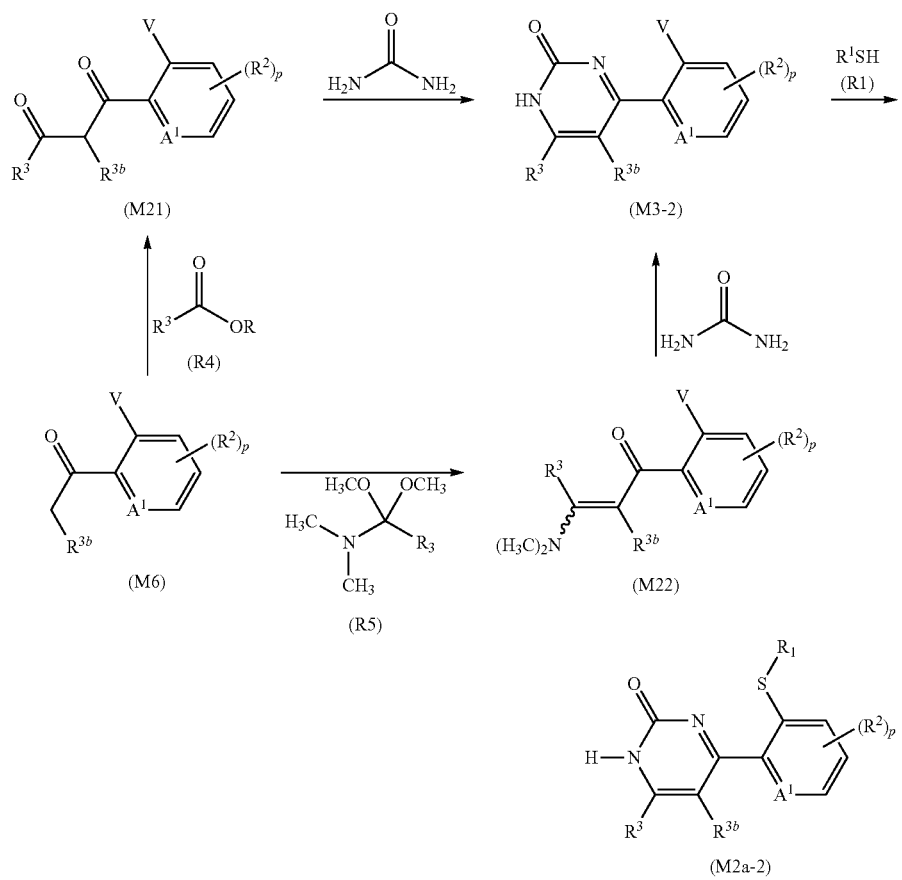

[wherein the symbols are the same as defined above.]

First, a process for preparing the compound represented by formula (M21) (hereinafter referred to as "Compound (M21)") is described.

The Compound (M21) may be prepared by reacting the Compound (M6) with the compound represented by formula (R4) (hereinafter referred to as "Compound (R4)") in the presence of a base.

The reaction is usually carried out in the presence of a solvent.

Examples of the solvent to be used in the reaction include ethers, halogenated aliphatic hydrocarbons, aromatic hydrocarbons, aprotic polar solvents, and mixed solvents thereof.

Examples of the base to be used in the reaction include alkali metal hydrides, alkali metal carbonates, alkali metal alkoxides, and organic bases.

In the reaction, the Compound (R4) is usually used within a range of 1 to 10 molar ratio(s), and the base is usually used within a range of 0.1 to 5 molar ratios, as opposed to 1 mole of the Compound (M6).

The reaction temperature of the reaction is usually within a range of −20° C. to 200° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M21). The isolated Compound (M21) may be further purified by, for example, chromatography or recrystallization.

Next, a process for preparing the compound represented by formula (M3-2) (hereinafter referred to as "Compound (M3-2)") is described.

The Compound (M3-2) may be prepared by reacting the Compound (M21) with urea.

The reaction is usually carried out in the presence of a solvent.

Examples of the solvent to be used in the reaction include nitriles, alcohols, aprotic polar solvents, acetic acid, water, and mixed solvents thereof.

In the reaction, the urea is usually used within a range of 1 to 10 molar ratio(s), as opposed to 1 mole of the Compound (M21).

The reaction temperature of the reaction is usually within a range of −20° C. to 200° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M3-2). The isolated Compound (M3-2) may be further purified by, for example, chromatography or recrystallization.

Next, a process for preparing the compound represented by formula (M22) (hereinafter referred to as "Compound (M22)") is described.

The Compound (M22) may be prepared by reacting the Compound (M6) with the compound represented by formula (R5) (hereinafter referred to as "Compound (R5)").

The reaction is usually carried out in the presence of a solvent.

Examples of the solvent to be used in the reaction include ethers, aromatic hydrocarbons, aprotic polar solvents, and mixed solvents thereof.

In the reaction, the Compound (R5) is usually used within a range of 1 to 100 molar ratio(s), as opposed to 1 mole of the Compound (M6). Also, the Compound (R5) may be used also as a solvent.

The reaction temperature of the reaction is usually within a range of −20° C. to 200° C. The reaction period of the reaction is usually within a range of 0.1 to 24 hours.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M22). The isolated Compound (M22) may be further purified by, for example, chromatography or recrystallization.

Next, a process for preparing the Compound (M3-2) from the Compound (22) is described.

When the reaction is completed, the reaction mixtures are added to water and then extracted with organic solvent(s), and the organic layers are concentrated; the reaction mixtures are added to water, and the resulting solids are collected by filtration; or the resulting solids in the reaction mixtures are collected by filtration, to isolate the Compound (M3-2). The isolated Compound (M3-2) may be further purified by, for example, chromatography or recrystallization.

Next, a process for preparing the Compound (M2a-2) is described.

The Compound (M2a-2) may be prepared by reacting the Compound (M3-2) with the Compound (R1) in the presence of abase.

The reaction may be carried out by using the Compound (M3-2) instead of the Compound (M1) according to the method described in the Process 2 to prepare the Compound (M2a-2).

Process 12

The Compound (M2a-2) may be prepared according to, for example, the following process.

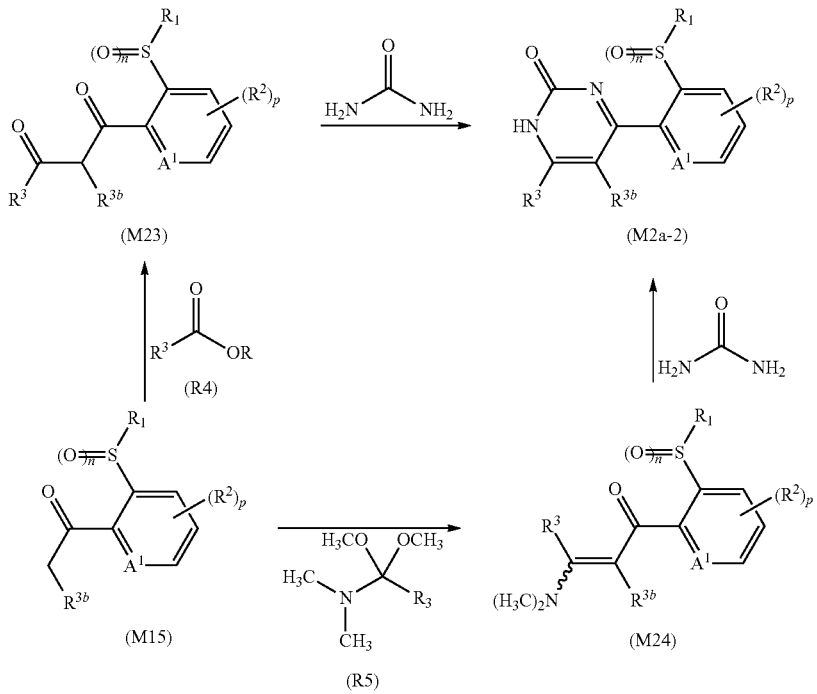

The Compound (M3-2) may be prepared by reacting the Compound (22) with urea.

The reaction is usually carried out in the presence of a solvent.

Examples of the solvent to be used in the reaction include nitriles, alcohols, aprotic polar solvents, acetic acid, water, and mixed solvents thereof.

In the reaction, the urea is usually used within a range of 1 to 10 molar ratio(s), as opposed to 1 mole of the Compound (M22).

The reaction temperature of the reaction is usually within a range of −20° C. to 200° C. The reaction period of the reaction is usually within a range of 0.1 to 24 hours.

[wherein the symbols are the same as defined above.]

First, a process for preparing the compound represented by formula (M23) (hereinafter referred to as "Compound (M23)") is described.

The Compound (M23) may be prepared by reacting the Compound (M15) with the Compound (R4) in the presence of a base.

The reaction may be carried out by using the Compound (M15) instead of the Compound (M6) according to the method described in the Process 11 to prepare the Compound (M23).

Next, a process for preparing the Compound (M2a-2) is described.

The Compound (M2a-2) may be prepared by reacting the Compound (M23) with urea.

The reaction may be carried out by using the Compound (M23) instead of the Compound (M21) according to the method described in the Process 11 to prepare the Compound (M2a-2).

Next, a process for preparing the compound represented by formula (M24) (hereinafter referred to as "Compound (M24)") is described.

The Compound (M24) may be prepared by reacting the Compound (M15) with the Compound (R5).

The reaction may be carried out by using the Compound (M15) instead of the Compound (M6) according to the method described in the Process 11 to prepare the Compound (M24).

Next, a process for preparing the Compound (M2a-2) by using the Compound (M24) is described.

The Compound (M2a-2) may be prepared by reacting the Compound (M24) with urea.

The reaction may be carried out by using the Compound (M24) instead of the Compound (M22) according to the method described in the Process 11 to prepare the Compound (M2a-2).

Process 13

The compound of the present invention wherein Q is an oxygen atom, p is 1, and $R^2$ is a $OR^5$ in formula (1) (hereinafter referred to as "Present compound (1e)") may be prepared by reacting the compound of the present invention wherein Q is an oxygen atom, p is 1, and $R^2$ is a $X^2$ in formula (1) (hereinafter referred to as "Present compound (1d)") with the compound represented by formula (R16) (hereinafter referred to as "Compound (R16)") in the presence of a base.

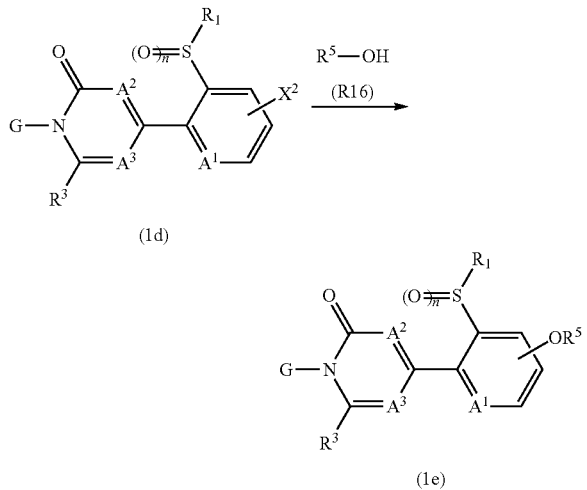

[wherein $X^2$ represents a fluorine atom, a chlorine atom, or a $S(O)_2R^1$; and the other symbols are the same as defined above.]

Examples of the solvent to be used in the reaction include ethers, aliphatic hydrocarbons, aromatic hydrocarbons, halogenated aliphatic hydrocarbons, esters, nitriles, aprotic polar solvents, nitrogen-containing aromatic compounds, and mixed solvents thereof.

Examples of the base to be used in the reaction include alkali metal carbonates, alkali metal hydrides, and organic bases.

In the reaction, the Compound (R16) is usually used within a range of 1 to 10 molar ratio(s), and the base is usually used within a range of 1 to 10 molar ratio(s), as opposed to 1 mole of the Present compound (1d).

The reaction temperature of the reaction is usually within a range of 0 to 200° C. The reaction period of the reaction is usually within a range of 0.1 to 24 hours.

When the reaction is completed, to the reaction mixtures is added water, and the reaction mixtures are then extracted with organic solvent(s), and the organic layers are worked up (for example, dried or concentrated) to isolate the Present compound (1e). The isolated Present compound (1e) may be further purified by, for example, chromatography or recrystallization.

Process 14

The compound of the present invention wherein Q is an oxygen atom, p is 1, $R^2$ is a $NR^5R^6$ in formula (1) (hereinafter referred to as "Present compound (1f)") may be prepared by reacting the Present compound (1d) with the compound represented by formula (R15) (hereinafter referred to as "Compound (R15)").

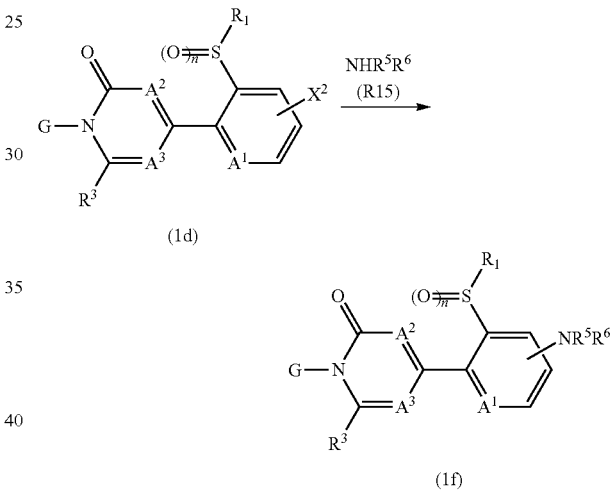

[wherein the symbols are the same as defined above.]

The reaction is usually carried out in the presence of a solvent.

Examples of the solvent to be used in the reaction include ethers, aliphatic hydrocarbons, aromatic hydrocarbons, halogenated aliphatic hydrocarbons, esters, nitriles, aprotic polar solvents, nitrogen-containing aromatic compounds, and mixed solvents thereof.

A base may optionally be added to the reaction as needed.

Examples of the base to be used in the reaction include alkali metal carbonates, alkali metal hydrides, and organic bases.

In the reaction, the Compound (R15) is usually used within a range of 1 to 10 molar ratio(s), and the base is usually used within a range of 1 to 10 molar ratio(s), as opposed to 1 mole of the Present compound (1d).

The reaction temperature of the reaction is usually within a range of 0 to 200° C. The reaction period of the reaction is usually within a range of 0.1 to 24 hours.

When the reaction is completed, to the reaction mixtures is added water, and the reaction mixtures are then extracted with organic solvent(s), and the organic layers are worked up (for example, dried or concentrated) to isolate the Present compound (1f). The isolated Present compound (1f) may be further purified by, for example, chromatography or recrystallization.

Process 15

The compound of the present invention wherein Q is an oxygen atom, p is 1, and $R^2$ is a $SR^5$ in formula (1) (hereinafter referred to as "Present compound (1g)"), the compound of the present invention wherein Q is an oxygen atom, p is 1, and $R^2$ is a $S(O)R^8$ (hereinafter referred to as "Present compound (1h)"), and the compound of the present invention wherein Q is an oxygen atom, p is 1, and $R^2$ is a $S(O)_2R8$ (hereinafter referred to as "Present compound (1i)") may be prepared according to, for example, the following process.

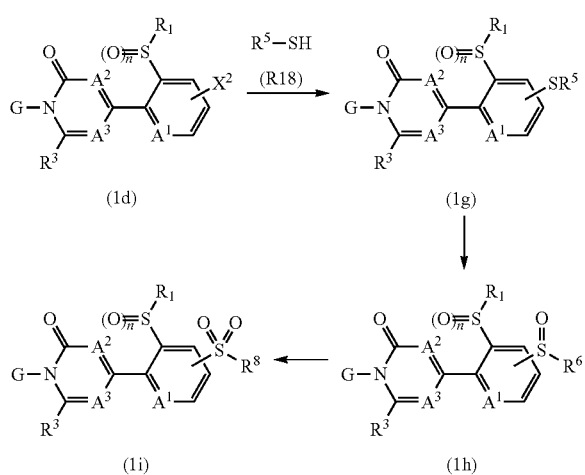

[wherein the symbols are the same as defined above.]

First, a process for preparing the Present compound (1g) is described.

The Present compound (1g) may be prepared by reacting the Present compound (1d) with the compound represented by formula (R18) (hereinafter referred to as "Compound (R18)") in the presence of a base.

The reaction may be carried out by using the Compound (R18) instead of the Compound (R16) according to the method described in the Process 13 to prepare the Present compound (1g).

Next, a process for preparing the Present compound (1h) is described.

The present compound (1h) may be prepared by reacting the Present compound (1g) with an oxidizing agent.

The reaction may be carried out by using the Compound (1g) instead of the Compound (1a) according to the method described in the Process 1 to prepare the compound (1h).

Next, a process for preparing the Present compound (1i) is described.

The Present compound (1i) may be prepared by reacting the Present compound (1h) with an oxidizing agent.

The reaction may be carried out by using the Compound (1h) instead of the Compound (1b) according to the method described in the Process 1 to prepare the Compound (1i).

Process 16

The compound of the present invention (1y) wherein Q is a sulfur atom in formula (1) (hereinafter referred to as "Present compound (1y)") may be prepared by reacting the compound of the present invention (1z) wherein Q is an oxygen atom in formula (1) (hereinafter referred to as "Present compound (1z)") with a sulfating agent.

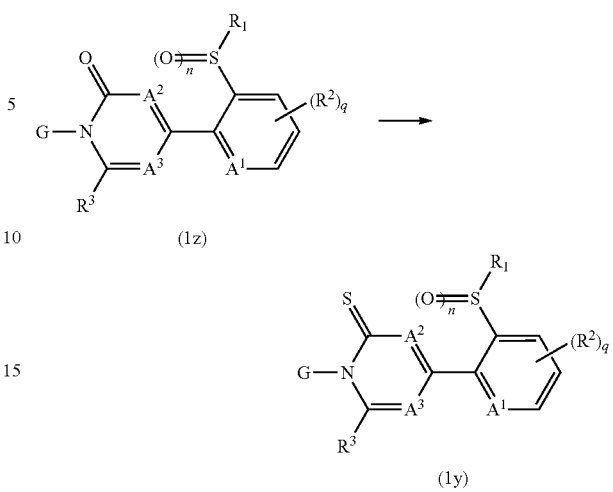

[wherein the symbols are the same as defined above.]

The reaction is usually carried out in the presence of a solvent.

Examples of the solvent to be used in the reaction include ethers, aliphatic hydrocarbons, aromatic hydrocarbons, halogenated aliphatic hydrocarbons, and mixed solvents thereof.

Examples of the sulfating agent to be used in the reaction include 2,4-bis(4-methoxyphenyl)-1,3,2,4-dithiadiphosphetane-2,4-di sulfide and phosphorus pentasulfide.

In the reaction, the sulfating agent is usually used within a range of 1 to 10 molar ratio(s), as opposed to 1 mole of the Present compound (1z).

The reaction temperature of the reaction is usually within a range of –20 to 200° C. The reaction period of the reaction is usually within a range of 0.1 to 24 hours.

When the reaction is completed, to the reaction mixtures is added water, and the reaction mixtures are then extracted with organic solvent(s), and the organic layers are worked up (for example, dried or concentrated) to isolate the Present compound (1y). The isolated Present compound (1y) may be further purified by, for example, chromatography or recrystallization.

Process 17

The compound of the present invention represented by formula (1L) (hereinafter referred to as "Present compound (1L)") may be prepared by reacting the Present compound (1d) with the compound represented by formula (R28) (hereinafter referred to as "Compound (R28)") in the presence of a base.

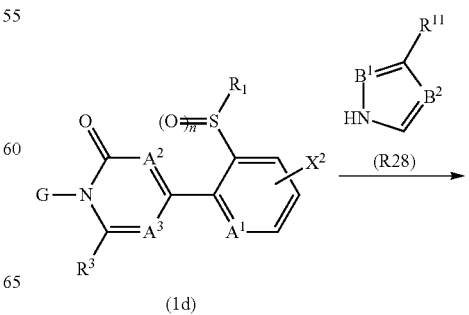

-continued

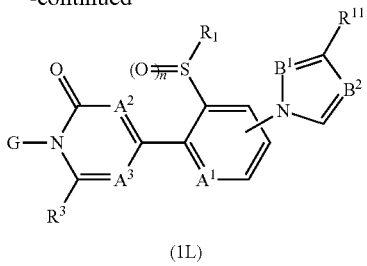

(1L)

[wherein $B^1$ and $B^2$ represent independently of each other a nitrogen atom or a CH; $R^1$ represents a hydrogen atom, or an atom or a group selected from Group A; and the other symbols are the same as defined above.]

The reaction may be carried out by using the Compound (R28) instead of the Compound (R16) according to the method described in the Process 13 to prepare the Present compound (1L).

Process 18

The compound of the present invention represented by formula (1m) (hereinafter referred to as "Present compound (1m)") may be prepared by reacting the Present compound (1d) with the compound represented by formula (R29) (hereinafter referred to as "Compound (R29)").

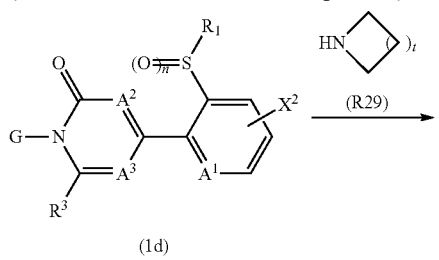

[wherein t represents an integer of 0 to 4; and the other symbols are the same as defined above.]

The reaction may be carried out by using the Compound (R29) instead of the Compound (R15) according to the method described in the Process 14 to prepare the Present compound (1m).

Next, specific examples of the compound of the present invention are shown below.

The compound of the present invention represented by formula (1-5):

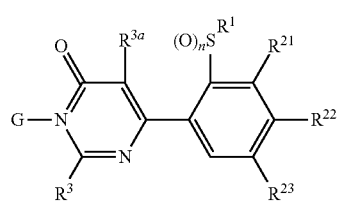

(1-5)

wherein $R^3$ and $R^{3a}$ are each a hydrogen atom; $R^{21}$, $R^{22}$, and $R^{23}$ are each a hydrogen atom; and $R^1$, G, and n represent any one combination indicated in Table 1 to Table 4.

The compound of the present invention represented by formula (1-5) wherein $R^3$ and $R^{3a}$ are each a hydrogen atom; $R^{21}$ and $R^{23}$ are each a hydrogen atom; $R^{22}$ is a trifluoromethyl group; and $R^1$, G, and n represent any one combination indicated in Table 1 to Table 4.

The compound of the present invention represented by formula (1-5) wherein $R^3$ is a hydrogen atom; $R^{21}$, $R^{22}$, and $R^{23}$ are each a hydrogen atom; $R^{3a}$ is a $CH_3$; and $R^1$, G, and n represent any one combination indicated in Table 1 to Table 4.

The compound of the present invention represented by formula (1-5) wherein $R^3$ is a hydrogen atom; $R^{21}$ and $R^{23}$ are each a hydrogen atom; $R^{22}$ is a trifluoromethyl group; $R^{3a}$ is a $CH_3$; and $R^1$, G, and n represent any one combination indicated in Table 1 to Table 4.

The compound of the present invention represented by formula (1-5) wherein $R^3$ is a hydrogen atom; $R^{21}$, $R^{22}$, and $R^{23}$ are each a hydrogen atom; $R^{3a}$ is a fluorine atom; and $R^1$, G, and n represent any one combination indicated in Table 1 to Table 4.

The compound of the present invention represented by formula (1-5) wherein $R^3$ is a hydrogen atom; $R^{21}$ and $R^{23}$ are each a hydrogen atom; $R^{22}$ is a trifluoromethyl group; $R^{3a}$ is a fluorine atom; and $R^1$, G, and n represent any one combination indicated in Table 1 to Table 4.

The compound of the present invention represented by formula (1-5) wherein $R^3$ is a hydrogen atom; $R^{21}$, $R^{22}$, and $R^{23}$ are each a hydrogen atom; $R^{3a}$ is a chlorine atom; and $R^1$, G, and n represent any one combination indicated in Table 1 to Table 4.

The compound of the present invention represented by formula (1-5) wherein $R^3$ is a hydrogen atom; $R^{21}$ and $R^{23}$ are each a hydrogen atom; $R^{22}$ is a trifluoromethyl group; $R^{3a}$ is a chlorine atom; and $R^1$, G, and n represent any one combination indicated in Table 1 to Table 4.

The compound of the present invention represented by formula (1-5) wherein $R^{3a}$ is a hydrogen atom; $R^{21}$, $R^{22}$, and $R^{23}$ are each a hydrogen atom; $R^3$ is a $CH_3$; and $R^1$, G, and n represent any one combination indicated in Table 1 to Table 4.

The compound of the present invention represented by formula (1-5) wherein $R^{3a}$ is a hydrogen atom; $R^{21}$ and $R^{23}$ are each a hydrogen atom; $R^{22}$ is a trifluoromethyl group; $R^3$ is a $CH_3$; and $R^1$, G, and n represent any one combination indicated in Table 1 to Table 4.

The compound of the present invention represented by formula (1-5) wherein $R^3$ and $R^{3a}$ are each a hydrogen atom; and $R^1$, G, n, $R^{21}$, $R^{22}$, and $R^{23}$ represent any one combination indicated in Table 5 to Table 13.

TABLE 1

| G | $R^1$ | n |
|---|---|---|
| $CF_2HCH_2$ | $CH_3CH_2$ | 2 |
| $CH_3CF_2$ | $CH_3CH_2$ | 2 |
| $CF_3CH_2$ | $CH_3CH_2$ | 2 |
| $CCl_3CH_2$ | $CH_3CH_2$ | 2 |
| $CF_2HCF_2$ | $CH_3CH_2$ | 2 |
| $CHClFCF_2$ | $CH_3CH_2$ | 2 |
| $CF_3CH_2CH_2$ | $CH_3CH_2$ | 2 |
| $CF_2HCF_2CH_2$ | $CH_3CH_2$ | 2 |
| $CF_3CF_2CH_2$ | $CH_3CH_2$ | 2 |
| $CBrF_2CF_2$ | $CH_3CH_2$ | 2 |
| $CF_3CFHCF_2$ | $CH_3CH_2$ | 2 |
| $CH_3CF_2CH_2$ | $CH_3CH_2$ | 2 |
| $CF_3CH(CH_3)$ | $CH_3CH_2$ | 2 |
| $CF_3C(CH_3)_2$ | $CH_3CH_2$ | 2 |

TABLE 1-continued

| G | R¹ | n |
|---|---|---|
| CH(CH₃)₂CH(CF₃) | CH₃CH₂ | 2 |
| (CF₃)₂CH | CH₃CH₂ | 2 |
| CH₃CH₂CH(CF₃) | CH₃CH₂ | 2 |
| CF₃CCl₂CH₂ | CH₃CH₂ | 2 |
| CF₃CF₂CH(CH₃) | CH₃CH₂ | 2 |
| CF₃CF₂CH(CH₂CH₃) | CH₃CH₂ | 2 |
| C(CH₃)(CF₃)₂CH₂ | CH₃CH₂ | 2 |
| CF₃CFHCF₂CH₂ | CH₃CH₂ | 2 |
| CF₃(CF₂)₂CH₂ | CH₃CH₂ | 2 |
| CBrF₂CF₂CH₂CH₂ | CH₃CH₂ | 2 |
| CF₃CFHCF₂CH(CH₃) | CH₃CH₂ | 2 |

TABLE 2

| G | R¹ | n |
|---|---|---|
| CF₃CH=CHCH₂ | CH₃CH₂ | 2 |
| CF₃(CF₂)₃CH₂ | CH₃CH₂ | 2 |
| CF₃(CF₂)₄CH₂ | CH₃CH₂ | 2 |
| CF₃(CF₂)₃CH₂CH₂ | CH₃CH₂ | 2 |
| CF(CF₃)₂CF₂CF₂CH₂CH₂ | CH₃CH₂ | 2 |
| CF₂H(CF₂)₃CH₂ | CH₃CH₂ | 2 |
| CF₂H(CF₂)₅CH₂ | CH₃CH₂ | 2 |
| CF₃(CF₂)₃CH₂CH₂CH₂ | CH₃CH₂ | 2 |
| CF₃CF₂(CH₂)₅CH₂ | CH₃CH₂ | 2 |
| CF₃(CF₂)₅CH₂CH₂CH₂ | CH₃CH₂ | 2 |
| CF₃(CF₂)₃CH₂(CH₂)₄CH₂ | CH₃CH₂ | 2 |
| CF₃(CF₂)₅CH₂CH₂ | CH₃CH₂ | 2 |
| CF(CF₃)₂CH₂(CH₂)₄CH₂ | CH₃CH₂ | 2 |
| CF₃OCFHCF₂ | CH₃CH₂ | 2 |
| CH₃OCH₂CF₂CH₂ | CH₃CH₂ | 2 |
| CF₃CH₂OCH₂CF₂CH₂ | CH₃CH₂ | 2 |
| CH₂FCF₂CH₂ | CH₃CH₂ | 2 |
| CH₂ClCF₂CH₂ | CH₃CH₂ | 2 |
| CH₂BrCF₂CH₂ | CH₃CH₂ | 2 |
| CH₃OCH₂(CF₂)₂CH₂ | CH₃CH₂ | 2 |
| CF₃CH₂OCH₂(CF₂)₂CH₂ | CH₃CH₂ | 2 |
| CH₂F(CF₂)₂CH₂ | CH₃CH₂ | 2 |
| CH₂Cl(CF₂)₂CH₂ | CH₃CH₂ | 2 |
| CH₂Br(CF₂)₂CH₂ | CH₃CH₂ | 2 |
| CH₃OCH₂(CF₂)₃CH₂ | CH₃CH₂ | 2 |

TABLE 3

| G | R¹ | n |
|---|---|---|
| CF₃CH₂OCH₂(CF₂)₃CH₂ | CH₃CH₂ | 2 |
| CH₃OCH₂(CF₂)₃CH₂ | CH₃CH₂ | 2 |
| CF₃CH₂OCH₂(CF₂)₃CH₂ | CH₃CH₂ | 2 |
| CH₂F(CF₂)₃CH₂ | CH₃CH₂ | 2 |
| CH₂Cl(CF₂)₃CH₂ | CH₃CH₂ | 2 |
| CH₂Br(CF₂)₃CH₂ | CH₃CH₂ | 2 |
| CH₃OCH₂(CF₂)₄CH₂ | CH₃CH₂ | 2 |
| CF₃CH₂OCH₂(CF₂)₄CH₂ | CH₃CH₂ | 2 |
| CH₂F(CF₂)₄CH₂ | CH₃CH₂ | 2 |
| CH₂Cl(CF₂)₄CH₂ | CH₃CH₂ | 2 |
| CH₂Br(CF₂)₄CH₂ | CH₃CH₂ | 2 |
| CF₃CF₂OCFHCF₂ | CH₃CH₂ | 2 |
| CF₃CF₂CF₂OCFHCF₂ | CH₃CH₂ | 2 |
| CF₃CF₂CF₂OCF(CF₃)CH₂ | CH₃CH₂ | 2 |
| CF₃CH₂OCH₂CH₂ | CH₃CH₂ | 2 |
| CH₃SCH₂CF₂CH₂ | CH₃CH₂ | 2 |
| CH₃S(O)CH₂CF₂CH₂ | CH₃CH₂ | 2 |
| CH₃S(O)₂CH₂CF₂CH₂ | CH₃CH₂ | 2 |
| CF₃CH₂SCH₂CF₂CH₂ | CH₃CH₂ | 2 |
| CF₃CH₂S(O)CH₂CF₂CH₂ | CH₃CH₂ | 2 |
| CF₃CH₂S(O)₂CH₂CF₂CH₂ | CH₃CH₂ | 2 |
| CF₃SCH₂CF₂CH₂ | CH₃CH₂ | 2 |
| CF₃S(O)CH₂CF₂CH₂ | CH₃CH₂ | 2 |
| CF₃S(O)₂CH₂CF₂CH₂ | CH₃CH₂ | 2 |
| CF₃SCH₂(CF₂)₂CH₂ | CH₃CH₂ | 2 |

TABLE 4

| G | R¹ | n |
|---|---|---|
| CF₃S(O)CH₂(CF₂)₂CH₂ | CH₃CH₂ | 2 |
| CF₃S(O)₂CH₂(CF₂)₂CH₂ | CH₃CH₂ | 2 |
| CF₃SCH₂(CF₂)₃CH₂ | CH₃CH₂ | 2 |
| CF₃S(O)CH₂(CF₂)₃CH₂ | CH₃CH₂ | 2 |
| CF₃S(O)₂CH₂(CF₂)₃CH₂ | CH₃CH₂ | 2 |
| CF₃SCH₂(CF₂)₄CH₂ | CH₃CH₂ | 2 |
| CF₃S(O)CH₂(CF₂)₄CH₂ | CH₃CH₂ | 2 |
| CF₃S(O)₂CH₂(CF₂)₄CH₂ | CH₃CH₂ | 2 |
| CF₃CH₂SCH₂CH₂ | CH₃CH₂ | 2 |
| CF₃CH₂S(O)CH₂CH₂ | CH₃CH₂ | 2 |
| CF₃CH₂S(O)₂CH₂CH₂ | CH₃CH₂ | 2 |
| CF₃SCH₂CH₂ | CH₃CH₂ | 2 |
| CF₃S(O)CH₂CH₂ | CH₃CH₂ | 2 |
| CF₃S(O)₂CH₂CH₂ | CH₃CH₂ | 2 |

The compound of the present invention represented by formula (1-6):

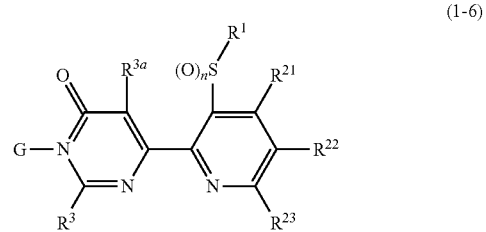

(1-6)

wherein $R^3$ and $R^{3a}$ are each a hydrogen atom; $R^{21}$, $R^{22}$, and $R^{23}$ are each a hydrogen atom; and $R^1$, G, and n represent any one combination indicated in Table 1 to Table 4.

The compound of the present invention represented by formula (1-6) wherein $R^3$ and $R^{3a}$ are each a hydrogen atom; $R^{21}$ and $R^{23}$ are each a hydrogen atom; $R^{22}$ is a trifluoromethyl group; and $R^1$, G, and n represent any one combination indicated in Table 1 to Table 4.

The compound of the present invention represented by formula (1-6) wherein $R^3$ is a hydrogen atom; $R^{21}$, $R^{22}$, and $R^{23}$ are each a hydrogen atom; $R^{3a}$ is a $CH_3$; and $R^1$, G, and n represent any one combination indicated in Table 1 to Table 4.

The compound of the present invention represented by formula (1-6) wherein $R^3$ is a hydrogen atom; $R^{21}$ and $R^{23}$ are each a hydrogen atom; $R^{22}$ is a trifluoromethyl group; $R^{3a}$ is a $CH_3$; and $R^1$, G, and n represent any one combination indicated in Table 1 to Table 4.

The compound of the present invention represented by formula (1-6) wherein $R^3$ is a hydrogen atom; $R^{21}$, $R^{22}$, and $R^{23}$ are each a hydrogen atom; $R^{3a}$ is a fluorine atom; and $R^1$, G, n, $R^{21}$, $R^{22}$, and $R^{23}$ represent any one combination indicated in Table 1 to Table 4.

The compound of the present invention represented by formula (1-6) wherein $R^3$ is a hydrogen atom; $R^{21}$ and $R^{23}$ are each a hydrogen atom; $R^{22}$ is a trifluoromethyl group; $R^{3a}$ is a fluorine atom; and $R^1$, G, and n represent any one combination indicated in Table 1 to Table 4.

The compound of the present invention represented by formula (1-6) wherein $R^3$ is a hydrogen atom; $R^{21}$, $R^{22}$, and $R^{23}$ are each a hydrogen atom; $R^{3a}$ is a chlorine atom; and $R^1$, G, and n represent any one combination indicated in Table 1 to Table 4.

The compound of the present invention represented by formula (1-6) wherein $R^3$ is a hydrogen atom; $R^{21}$ and $R^{23}$ are each a hydrogen atom; $R^{22}$ is a trifluoromethyl group;

$R^{3a}$ is a chlorine atom; and $R^1$, G, and n represent any one combination indicated in Table 1 to Table 4.

The compound of the present invention represented by formula (1-6) wherein $R^{3a}$ is a hydrogen atom; $R^{21}$, $R^{22}$, and $R^{23}$ are each a hydrogen atom; $R^3$ is a $CH_3$; and $R^1$, G, and n represent any one combination indicated in Table 1 to Table 4.

The compound of the present invention represented by formula (1-6) wherein $R^{3a}$ is a hydrogen atom; $R^{21}$ and $R^{23}$ are each a hydrogen atom; $R^{22}$ is a trifluoromethyl group; $R^3$ is a $CH_3$; and $R^1$, G, and n represent any one combination indicated in Table 1 to Table 4.

The compound of the present invention represented by formula (1-6) wherein $R^3$ and $R^{3a}$ are each a hydrogen atom; and $R^1$, G, n, $R^{21}$, $R^{22}$, and $R^{23}$ represent any one combination indicated in Table 5 to Table 13.

TABLE 5

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | $OCH_3$ |
| $CF_3CF_2CH_2$ | $CH_3CH_2$ | 2 | H | H | $OCH_3$ |
| $CF_3CFHCF_2CH_2$ | $CH_3CH_2$ | 2 | H | H | $OCH_3$ |
| $CF_3CF_2CH_2CH_2$ | $CH_3CH_2$ | 2 | H | H | $OCH_3$ |
| $CF_2HCF_2CF_2CF_2CH_2$ | $CH_3CH_2$ | 2 | H | H | $OCH_3$ |
| $CCl_2$=$CHCH_2$ | $CH_3CH_2$ | 2 | H | H | $OCH_3$ |
| $CF_2$=$CFCH_2CH_2$ | $CH_3CH_2$ | 2 | H | H | $OCH_3$ |
| $CF_2HCF_2CH_2$ | $CH_3CH_2$ | 2 | H | H | $OCH_2CF_3$ |
| $CF_3CF_2CH_2$ | $CH_3CH_2$ | 2 | H | H | $OCH_2CF_3$ |
| $CF_3CFHCF_2CH_2$ | $CH_3CH_2$ | 2 | H | H | $OCH_2CF_3$ |
| $CF_3CF_2CH_2CH_2$ | $CH_3CH_2$ | 2 | H | H | $OCH_2CF_3$ |
| $CF_2HCF_2CF_2CF_2CH_2$ | $CH_3CH_2$ | 2 | H | H | $OCH_2CF_3$ |
| $CCl_2$=$CHCH_2$ | $CH_3CH_2$ | 2 | H | H | $OCH_2CF_3$ |
| $CF_2$=$CFCH_2CH_2$ | $CH_3CH_2$ | 2 | H | H | $OCH_2CF_3$ |
| $CF_2HCF_2CH_2$ | $CH_3CH_2$ | 2 | H | H | $OCH_2C\equiv CH$ |
| $CF_3CF_2CH_2$ | $CH_3CH_2$ | 2 | H | H | $OCH_2C\equiv CH$ |
| $CF_3CFHCF_2CH_2$ | $CH_3CH_2$ | 2 | H | H | $OCH_2C\equiv CH$ |
| $CF_3CF_2CH_2CH_2$ | $CH_3CH_2$ | 2 | H | H | $OCH_2C\equiv CH$ |
| $CF_2HCF_2CF_2CF_2CH_2$ | $CH_3CH_2$ | 2 | H | H | $OCH_2C\equiv CH$ |
| $CCl_2$=$CHCH_2$ | $CH_3CH_2$ | 2 | H | H | $OCH_2C\equiv CH$ |
| $CF_2$=$CFCH_2CH_2$ | $CH_3CH_2$ | 2 | H | H | $OCH_2C\equiv CH$ |

TABLE 6

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | $NH_2$ |
| $CF_3CF_2CH_2$ | $CH_3CH_2$ | 2 | H | H | $NH_2$ |
| $CF_3CFHCF_2CH_2$ | $CH_3CH_2$ | 2 | H | H | $NH_2$ |
| $CF_3CF_2CH_2CH_2$ | $CH_3CH_2$ | 2 | H | H | $NH_2$ |
| $CF_2HCF_2CF_2CF_2CH_2$ | $CH_3CH_2$ | 2 | H | H | $NH_2$ |
| $CCl_2$=$CHCH_2$ | $CH_3CH_2$ | 2 | H | H | $NH_2$ |
| $CF_2$=$CFCH_2CH_2$ | $CH_3CH_2$ | 2 | H | H | $NH_2$ |
| $CF_2HCF_2CH_2$ | $CH_3CH_2$ | 2 | H | H | $NHCH_3$ |
| $CF_3CF_2CH_2$ | $CH_3CH_2$ | 2 | H | H | $NHCH_3$ |
| $CF_3CFHCF_2CH_2$ | $CH_3CH_2$ | 2 | H | H | $NHCH_3$ |
| $CF_3CF_2CH_2CH_2$ | $CH_3CH_2$ | 2 | H | H | $NHCH_3$ |
| $CF_2HCF_2CF_2CF_2CH_2$ | $CH_3CH_2$ | 2 | H | H | $NHCH_3$ |
| $CCl_2$=$CHCH_2$ | $CH_3CH_2$ | 2 | H | H | $NHCH_3$ |
| $CF_2$=$CFCH_2CH_2$ | $CH_3CH_2$ | 2 | H | H | $NHCH_3$ |
| $CF_2HCF_2CH_2$ | $CH_3CH_2$ | 2 | H | H | $N(CH_3)_2$ |
| $CF_3CF_2CH_2$ | $CH_3CH_2$ | 2 | H | H | $N(CH_3)_2$ |
| $CF_3CFHCF_2CH_2$ | $CH_3CH_2$ | 2 | H | H | $N(CH_3)_2$ |
| $CF_3CF_2CH_2CH_2$ | $CH_3CH_2$ | 2 | H | H | $N(CH_3)_2$ |
| $CF_2HCF_2CF_2CF_2CH_2$ | $CH_3CH_2$ | 2 | H | H | $N(CH_3)_2$ |
| $CCl_2$=$CHCH_2$ | $CH_3CH_2$ | 2 | H | H | $N(CH_3)_2$ |
| $CF_2$=$CFCH_2CH_2$ | $CH_3CH_2$ | 2 | H | H | $N(CH_3)_2$ |

TABLE 7

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | pyrazol-1-yl |
| $CF_3CF_2CH_2$ | $CH_3CH_2$ | 2 | H | H | pyrazol-1-yl |
| $CF_3CFHCF_2CH_2$ | $CH_3CH_2$ | 2 | H | H | pyrazol-1-yl |
| $CF_3CF_2CH_2CH_2$ | $CH_3CH_2$ | 2 | H | H | pyrazol-1-yl |
| $CF_2HCF_2CF_2CF_2CH_2$ | $CH_3CH_2$ | 2 | H | H | pyrazol-1-yl |
| $CCl_2$=$CHCH_2$ | $CH_3CH_2$ | 2 | H | H | pyrazol-1-yl |
| $CF_2$=$CFCH_2CH_2$ | $CH_3CH_2$ | 2 | H | H | pyrazol-1-yl |

TABLE 8

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | imidazol-1-yl |
| $CF_3CF_2CH_2$ | $CH_3CH_2$ | 2 | H | H | imidazol-1-yl |
| $CF_3CFHCF_2CH_2$ | $CH_3CH_2$ | 2 | H | H | imidazol-1-yl |
| $CF_3CF_2CH_2CH_2$ | $CH_3CH_2$ | 2 | H | H | imidazol-1-yl |

TABLE 8-continued

| G | R¹ | n | R²¹ | R²² | R²³ |
|---|---|---|---|---|---|
| CF$_2$HCF$_2$CF$_2$CF$_2$CH$_2$ | CH$_3$CH$_2$ | 2 | H | H | 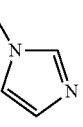 |
| CCl$_2$=CHCH$_2$ | CH$_3$CH$_2$ | 2 | H | H | 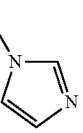 |
| CF$_2$=CFCH$_2$ | CH$_3$CH$_2$ | 2 | H | H | 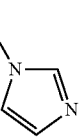 |
| CF$_2$HCF$_2$CH$_2$ | CH$_3$CH$_2$ | 2 | H | H | 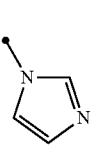 |

TABLE 9

| G | R¹ | n | R²¹ | R²² | R²³ |
|---|---|---|---|---|---|
| CF$_3$CF$_2$CH$_2$ | CH$_3$CH$_2$ | 2 | H | H | 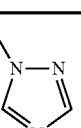 |
| CF$_3$CFHCF$_2$CH$_2$ | CH$_3$CH$_2$ | 2 | H | H | 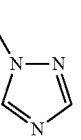 |
| CF$_3$CF$_2$CH$_2$CH$_2$ | CH$_3$CH$_2$ | 2 | H | H | 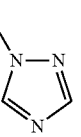 |
| CF$_2$HCF$_2$CF$_2$CF$_2$CH$_2$ | CH$_3$CH$_2$ | 2 | H | H | 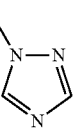 |
| CCl$_2$=CHCH$_2$ | CH$_3$CH$_2$ | 2 | H | H | 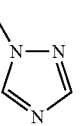 |
| CF$_2$=CFCH$_2$CH$_2$ | CH$_3$CH$_2$ | 2 | H | H | 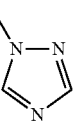 |

TABLE 10

| G | R¹ | n | R²¹ | R²² | R²³ |
|---|---|---|---|---|---|
| CF$_2$HCF$_2$CH$_2$ | CH$_3$CH$_2$ | 2 | H | H | Piperidin-1-yl |
| CF$_3$CF$_2$CH$_2$ | CH$_3$CH$_2$ | 2 | H | H | Piperidin-1-yl |
| CF$_3$CFHCF$_2$CH$_2$ | CH$_3$CH$_2$ | 2 | H | H | Piperidin-1-yl |
| CF$_3$CF$_2$CH$_2$CH$_2$ | CH$_3$CH$_2$ | 2 | H | H | Piperidin-1-yl |
| CF$_2$HCF$_2$CF$_2$CF$_2$CH$_2$ | CH$_3$CH$_2$ | 2 | H | H | Piperidin-1-yl |
| CCl$_2$=CHCH$_2$ | CH$_3$CH$_2$ | 2 | H | H | Piperidin-1-yl |
| CF$_2$=CFCH$_2$CH$_2$ | CH$_3$CH$_2$ | 2 | H | H | Piperidin-1-yl |
| CF$_2$HCF$_2$CH$_2$ | CH$_3$CH$_2$ | 2 | H | H | Pyrrolidin-1-yl |
| CF$_3$CF$_2$CH$_2$ | CH$_3$CH$_2$ | 2 | H | H | Pyrrolidin-1-yl |
| CF$_3$CFHCF$_2$CH$_2$ | CH$_3$CH$_2$ | 2 | H | H | Pyrrolidin-1-yl |
| CF$_3$CF$_2$CH$_2$CH$_2$ | CH$_3$CH$_2$ | 2 | H | H | Pyrrolidin-1-yl |
| CF$_2$HCF$_2$CF$_2$CF$_2$CH$_2$ | CH$_3$CH$_2$ | 2 | H | H | Pyrrolidin-1-yl |
| CCl$_2$=CHCH$_2$ | CH$_3$CH$_2$ | 2 | H | H | Pyrrolidin-1-yl |
| CF$_2$=CFCH$_2$CH$_2$ | CH$_3$CH$_2$ | 2 | H | H | Pyrrolidin-1-yl |

TABLE 11

| G | R¹ | n | R²¹ | R²² | R²³ |
|---|---|---|---|---|---|
| CF$_2$HCF$_2$CH$_2$ | CH$_3$CH$_2$ | 2 | H | H | 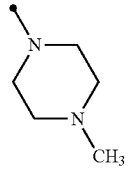 |
| CF$_3$CF$_2$CH$_2$ | CH$_3$CH$_2$ | 2 | H | H | 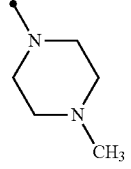 |
| CF$_3$CFHCF$_2$CH$_2$ | CH$_3$CH$_2$ | 2 | H | H | 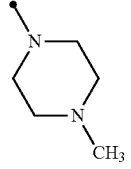 |
| CF$_3$CF$_2$CH$_2$CH$_2$ | CH$_3$CH$_2$ | 2 | H | H | 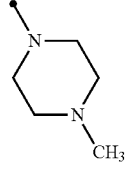 |
| CF$_2$HCF$_2$CF$_2$CF$_2$CH$_2$ | CH$_3$CH$_2$ | 2 | H | H | 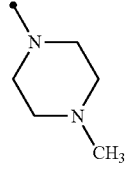 |
| CCl$_2$=CHCH$_2$ | CH$_3$CH$_2$ | 2 | H | H | 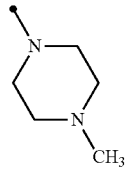 |

TABLE 11-continued

| G | $R^1$ | n | $R^{21}$ | $R^{22}$ | $R^{23}$ |
|---|---|---|---|---|---|
| $CF_2=CFCH_2CH_2$ | $CH_3CH_2$ | 2 | H | H | 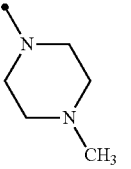 |

TABLE 12

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | Morpholin-1-yl |
| $CF_3CF_2CH_2$ | $CH_3CH_2$ | 2 | H | H | Morpholin-1-yl |
| $CF_3CFHCF_2CH_2$ | $CH_3CH_2$ | 2 | H | H | Morpholin-1-yl |
| $CF_3CF_2CH_2CH_2$ | $CH_3CH_2$ | 2 | H | H | Morpholin-1-yl |
| $CF_2HCF_2CF_2CF_2CH_2$ | $CH_3CH_2$ | 2 | H | H | Morpholin-1-yl |
| $CCl_2=CHCH_2$ | $CH_3CH_2$ | 2 | H | H | Morpholin-1-yl |
| $CF_2=CFCH_2CH_2$ | $CH_3CH_2$ | 2 | H | H | Morpholin-1-yl |
| $CF_2HCF_2CH_2$ | $CH_3CH_2$ | 2 | H | H | Thiomorpholin-1-yl |
| $CF_3CF_2CH_2$ | $CH_3CH_2$ | 2 | H | H | Thiomorpholin-1-yl |
| $CF_3CFHCF_2CH_2$ | $CH_3CH_2$ | 2 | H | H | Thiomorpholin-1-yl |
| $CF_3CF_2CH_2CH_2$ | $CH_3CH_2$ | 2 | H | H | Thiomorpholin-1-yl |
| $CF_2HCF_2CF_2CF_2CH_2$ | $CH_3CH_2$ | 2 | H | H | Thiomorpholin-1-yl |
| $CCl_2=CHCH_2$ | $CH_3CH_2$ | 2 | H | H | Thiomorpholin-1-yl |
| $CF_2=CFCH_2CH_2$ | $CH_3CH_2$ | 2 | H | H | Thiomorpholin-1-yl |

TABLE 13

| G | $R^1$ | n | $R^{21}$ | $R^{22}$ | $R^{23}$ |
|---|---|---|---|---|---|
| $CF_2HCF_2CH_2$ | $CH_3CH_2$ | 2 | H | H | $S(O)_2CH_2CH_3$ |
| $CF_3CF_2CH_2$ | $CH_3CH_2$ | 2 | H | H | $S(O)_2CH_2CH_3$ |
| $CF_3CFHCF_2CH_2$ | $CH_3CH_2$ | 2 | H | H | $S(O)_2CH_2CH_3$ |
| $CF_3CF_2CH_2CH_2$ | $CH_3CH_2$ | 2 | H | H | $S(O)_2CH_2CH_3$ |
| $CF_2HCF_2CF_2CF_2CH_2$ | $CH_3CH_2$ | 2 | H | H | $S(O)_2CH_2CH_3$ |
| $CCl_2=CHCH_2$ | $CH_3CH_2$ | 2 | H | H | $S(O)_2CH_2CH_3$ |
| $CF_2=CFCH_2CH_2$ | $CH_3CH_2$ | 2 | H | H | $S(O)_2CH_2CH_3$ |

The compound of the present invention represented by formula (1-7):

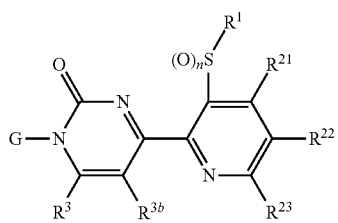

(1-7)

wherein $R^3$ and $R^{3b}$ are each a hydrogen atom; $R^{21}$, $R^{22}$, and $R^{23}$ are each a hydrogen atom; and $R^1$, G, and n represent any one combination indicated in Table 1 to Table 4.

The compound of the present invention represented by formula (1-7) wherein $R^3$ and $R^{3b}$ are each a hydrogen atom; $R^{21}$ and $R^{23}$ are each a hydrogen atom; $R^{22}$ is a trifluoromethyl group; and $R^1$, G, and n represent any one combination indicated in Table 1 to Table 4.

The compound of the present invention represented by formula (1-7) wherein $R^3$ and $R^{3b}$ are each a hydrogen atom; and $R^1$, G, n, $R^{21}$, $R^{22}$, and $R^{23}$ represent any one combination indicated in Table 5 to Table 13.

The compound of the present invention represented by formula (1-8):

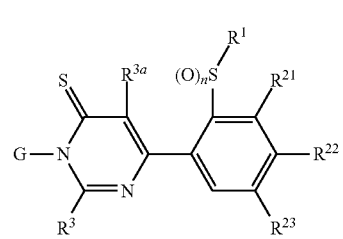

(1-8)

wherein $R^3$ and $R^{3b}$ are each a hydrogen atom; $R^{21}$, $R^{22}$, and $R^{23}$ are each a hydrogen atom; and $R^1$, G, and n represent any one combination indicated in Table 1 to Table 4.

The compound of the present invention represented by formula (1-8) wherein $R^3$ and $R^{3b}$ are each a hydrogen atom; $R^{21}$ and $R^{23}$ are each a hydrogen atom; $R^{22}$ is a trifluoromethyl group; and $R^1$, G, and n represent any one combination indicated in Table 1 to Table 4.

The compound of the present invention represented by formula (1-8) wherein $R^3$ and $R^{3b}$ are each a hydrogen atom; and $R^1$, G, n, $R^{21}$, $R^{22}$, and $R^{23}$ represent any one combination indicated in Table 5 to Table 13.

The compound of the present invention represented by formula (1-9):

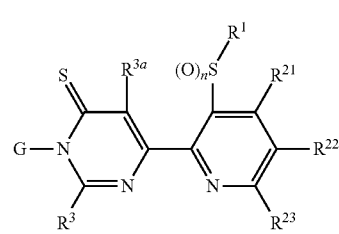

(1-9)

wherein $R^3$ and $R^{3b}$ are each a hydrogen atom; $R^{21}$, $R^{22}$, and $R^{23}$ are each a hydrogen atom; and $R^1$, G, and n represent any one combination indicated in Table 1 to Table 4.

The compound of the present invention represented by formula (1-9) wherein $R^3$ and $R^{3b}$ are each a hydrogen atom; $R^{21}$ and $R^{23}$ are each a hydrogen atom; $R^{22}$ is a trifluoromethyl group; and $R^1$, G, and n represent any one combination indicated in Table 1 to Table 4.

The compound of the present invention represented by formula (1-9) wherein $R^3$ and $R^{3b}$ are each a hydrogen atom; and $R^1$, G, n, $R^{21}$, $R^{22}$, and $R^{23}$ represent any one combination indicated in Table 5 to Table 13.

Examples of the harmful arthropod on which the compound of the present invention has a control efficacy include harmful insects and harmful mites. Specific examples of such harmful arthropod are as follows.

Hemiptera Pests:

Delphacidae (for example, *Laodelphax striatellus*, *Nilaparvata lugens*, *Sogatella furcifera*, or *Peregrinus maidis*), Deltocephalidae (for example, *Nephotettix cincticeps*, *Nephotettix virescens*, *Nephotettix nigropictus* (Rice green leafhopper), *Recilia dorsalis*, *Empoasca onukii*, *Empoasca fabae*, *Dalbulus maidis*, *Mahanarva posticata* (Sugarcane froghopper), *Mahanarva fimbriolota* (Sugarcane root spittlebug), *Cofana spectra*, *Nephotettix nigropictus*, or *Recilia dorsalis*), Aphididae (for example, *Aphis gossypii, Myzus persicae, Brevicoryne brassicae, Aphis spiraecola, Macrosiphum euphorbiae, Aulacorthum solani, Rhopalosiphumpadi, Toxoptera citricidus, Hyalopterus pruni, Aphis glycines Matsumura, Rhopalosiphum maidis, Tetraneura nigriabdominalis, Viteus vitifoliae, Daktulosphaira vitifoliae* (Grape Phylloxera), *Phylloxera devastatrix Pergande* (Pecan *phylloxera*), *Phylloxera notabilis pergande* (Pecan leaf *phylloxera*), or *Phylloxera russellae Stoetzel* (Southern pecan leaf *phylloxera*)), Pentatomidae (for example, *Scotinophara lurida, Scotinophara coarctata* (Malayan rice black bug), *Nezara antennata, Eysarcoris parvus, Halyomorpha mista, Nezara viridula, Euschistus heros* (Brown stink bug), *Nezara viridula* (Southern green stink bug), *Piezodorus guildinii* (Red banded stink bug), *Scaptocoris castanea* (Burrower brown bug), *Oebalus pugnax*, or *Dichelops melacanthus*), Alydidae (for example, *Riptortus clavetus, Leptocorisa chinensis, Leptocorisa acuta*, or *Leptocorisa* spp.), Miridae (for example, *Trigonotylus caelestialium, Stenotus rubrovittatus, Lygus lineolaris*, or *Blissus leucopterus leucopterus* (Chinchi bug)), Aleyrodidae (for example, *Trialeurodes vaporariorum, Bemisia tabaci, Dialeurodes citri*, or *Aleurocanthus spiniferus*), Coccoidea (for example, *Aonidiella aurantii, Comstockaspis perniciosa, Unaspis citri, Ceroplastes rubens, Icerya purchasi, Planococcus kraunhiae, Pseudococcus longispinis, Pseudaulacaspis pentagona*, or *Brevennia rehi*), Psyllidae (for example, *Diaphorina citri, Psylla pyrisuga*, or *Bactericerca cockerelli*), Tingidae (for example, *Stephanitis nasi*), Cimicoidea (for example, *Cimex lectularius*),

*Quesada gigas* (Giant Cicada);
and the others.

Lepidoptera Pests:

Pyralidae (for example, *Chilo suppressalis, Chilo polychrysus* (Darkheaded stm borer), *Tryporyza incertulas, Chilo polychrysus, Scirpophaga innotata, Scirpophaga incertulas* (Yellow stem borer), *Sesamia inferens* (Pink borer), *Rupela albinella, Cnaphalocrocis medinalis, Marasmia patnalis, Marasmia exigna, Notarcha derogata, Plodia interpunctella, Ostrinia furnacalis, Hellula undalis, Pediasia teterrellus, Nymphula depunctalis, Marasmia* spp., *Hydraecia immanis* (Hop vine borer), *Ostrinia nubilalis* (European corn borer), *Elasmopalpus lignosellus* (Lesser cornstalk borer), *Epinotia aporema* (Bean Shoot Borer), *Diatraea saccharalis* (Sugarcane borer), or *Telchin licus* (Giant Sugarcane borer)), Noctuidae (for example, *Spodoptera litura, Spodoptera exigua, Pseudaletia separata, Mamestra brassicae, Sesamia inferens, Spodoptera mauritia, Spodoptera frugiperda, Spodoptera exempta, Agrotis ipsilon, Plusia nigrisigna, Pseudoplusia includens* (Soybean looper), *Trichoplusia* spp., *Heliothis* spp. (for example, *Heliothis virescens*), *Helicoverpa* spp. (for example, *Helicoverpa armigera*), *Anticarsia gammatalis* (Velvetbean caterpillar), or *Alabama argillacea* (Cotton leafworm)), Pieridae (for example, *Pieris rapae*), Tortricidae (for example, *Adoxophyes* spp., *Grapholita molesta, Leguminivora glycinivorella, Matsumuraeses azukivora, Adoxophyes orana fasciata, Adoxophyes honmai, Homona magnanima, Archips fuscocupreanus*, or *Cydia pomonella*), Gracillariidae (for example, *Caloptilia theivora* or *Phyllonorycter ringoneella*), Carposinidae (for example, *Carposina niponensis* or *Ecdytolopha aurantiana* (Citrus fruit borer)), Lyonetiidae (for example, *Leucoptera coffeela* (Coffee Leaf miner) or *Lyonetia* spp.), Lymantriidae (for example, *Lymantria* spp. or *Euproctis* spp.), Yponomeutidae (for example, *Plutella xylostella*), Gelechiidae (for example, *Pectinophora gossypiella* or *Phthorimaea operculella*), Arctiidae (for example, *Hyphantria cunea*);
and the others.

Thysanoptera Pests:

Thysanopterae (for example, *Frankliniella occidentalis, Thrips parmi, Scirtothrips dorsalis, Thrips tabaci, Frankliniella intonsa, Frankliniella occidentalis, Haplothrips aculeatus*, or *Stenchaetothrips biformis*); and the others.

Diptera Pests:

House mosquitoes (*Culex* spp.) (for example, *Culex pipiens pallens, Culex tritaeniorhynchus*, or *Culex quinquefasciatus*),

*Aedes* spp. (for example, *Aedes aegypti* or *Aedes albopictus*),

*Anopheles* spp. (for example, *Anopheles sinensis*),

Chironomidae,

Muscidae (for example, *Musca domestica* or *Muscina stabulans*),

Anthomyiidae (for example, *Delia platura, Delia antiqua*, or *Tetanops myopaeformis*), Agromyzidae (for example, *Agromyza oryzae, Hydrellia griseola, Liriomyza sativae, Liriomyza trifolii*, or *Chromatomyia horticola*), Chloropidae (for example, *Chlorops oryzae*), Tephritidae (for example, *Dacus cucurbitae* or *Ceratitis capitata*), Ephydridae (for example, *Hydrellia philippina* or *Hydrellia sasakii*), Drosophilidae, Phoridae (for example, *Megaselia spiracularis*), Psychodidae (for example, *Clogmia albipunctata*), Sciaridae, Cecidomyiidae (for example, *Mayetiola destructor* or *Orseolia oryzae*), Diopsidae (for example, *Diopsis macrophthalma*), Tipulidae (for example, *Tipula oleracea* (Common cranefly), or *Tipula paludosa* (European cranefly));
and the others.

Coleoptera Pests:

Chrysomelidae (for example, *Diabrotica virgifera virgifera, Diabrotica undecimpunctata howardi, Diabrotica barberi, Diabrotica virgifera zeae, Diabrotica balteata LeConte, Diabrotica speciosa, Diabrotica speciosa* (Cucurbit Beetle), *Cerotoma trifurcata, Oulema melanopus, Aulacophora femoralis, Phyllotreta striolata, Leptinotarsa decemlineata, Oulema oryzae, Colaspis brunnea, Chaetocnema pulicaria, Epitrix cucumeris, Dicladispa armigera, Stenolophus lecontei* (Seedcorn beetle), or *Clivinia impressifrons* (Slender seedcorn beetle)), Scarabaeidae (for example, *Anomala cuprea, Anomala rufocuprea, Popillia japonica, Rhizotrogus majalis* (European Chafer), *Bothynus gibbosus* (carrot beetle), *Colaspis brunnea* (Grape Colaspis), *Myochrous denticollis* (southern Corn leaf beetle), *Holotrichia* spp., or *Phyllophaga* spp. (for example, *Phyllophaga crinita*)), Erirhinidae (for example, *Sitophilus zeamais, Echinocnemus squameus, Lissorhoptrus oryzophilus*, or *Sphenophorus venatus*), Curculionidae (for example, *Anthonomus grandis*, *Sphenophorus callosus* (Southern Corn Billbug), *Sternechus subsignatus* (Soybean stalk weevil), or *Sphenophorus* spp. (for example, *Sphenophorus levis*)),
   *Epilachna* (for example, *Epilachna vigintioctopunctata*),
   Scolytidae (for example, *Lyctus brunneus* or *Tomicus piniperda*),
   Bostrichidae,
   Ptinidae,
   Cerambycidae (for example, *Anoplophora malasiaca* or *Migdolus fryanus*),
   Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes ogurae fuscicollis*, or *Melanotus legatus*),
   Staphylinidae (for example, *Paederus fuscipes*),
   *Hypothenemus hampei* (Coffee Barry Borer);
   and the others.
Orthoptera Pests:
   *Locusta migratoria*, *Gryllotalpa africana*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Twostriped grasshopper), *Melanoplus sanguinipes* (Migratory grasshopper), *Melanoplus femurrubrum* (Red-Legged grasshopper), *Camnula pellucida* (Clearwinged grasshopper), *Schistocerca gregaria*, *Gastrimargus musicus* (Yellow-winged locust), *Austracris guttulosa* (Spur-throated locust), *Oxya yezoensis*, *Oxya japonica*, *Patanga succincta*, *Grylloidea* (for example, *Acheta domesticus*, *Teleogryllus emma*, or *Anabrus simplex* (Mormon cricket));
   and the others.
Hymenoptera Pests:
   Tenthredinidae (for example, *Athalia rosae*, or *Athalia japonica*),
   *Solenopsis* spp.,
   *Attini* spp. (for example, *Atta capiguara* (Brown leafcutting ant));
   and the others.
Blattariae Pests:
   *Blattella germanica*, *Periplaneta fuliginosa*, *Periplaneta americana*, *Periplaneta brunnea*, *Blatta orientalis*, and the others.
Isoptera Pests:
   *Reticulitermes speratus*, *Coptotermes formosanus*, *Incisitermes minor*, *Cryptotermes domesticus*, *Odontotermes formosanus*, *Neotermes koshunensis*, *Glyptotermes satsumensis*, *Glyptotermes nakajimai*, *Glyptotermes fuscus*, *Glyptotermes kodamai*, *Glyptotermes kushimensis*, *Hodotermopsis japonica*, *Coptotermes guangzhoensis*, *Reticulitermes miyatakei*, *Reticulitermes flaviceps amamianus*, *Reticulitermes* sp., *Nasutitermes takasagoensis*, *Pericapritermes nitobei*, *Sinocapritermes mushae*, or *Cornitermes cumulans*;
   and the others.
Acarina Pests:
   Tetranychidae (for example, *Tetranychus urticae*, *Tetranychus kanzawai*, *Panonychus citri*, *Panonychus ulmi*, *Oligonychus* spp., or *Brevipalpus phoenicis* (Southern Turkey spider mites)),
   Eriophyidae (for example, *Aculops pelekassi*, *Phyllocoptruta citri*, *Aculops lycopersici*, *Calacarus carinatus*, *Acaphylla theavagrans*, *Eriophyes chibaensis*, or *Aculus schlechtendali*),
   Tarsonemidae (for example, *Polyphagotarsonemus latus*),
   Tenuipalpidae (for example, *Brevipalpus phoenicis*),
   Tuckerellidae,
   Ixodidae (for example, *Haemaphysalis longicornis*, *Haemaphysalis flava*, *Dermacentor taiwanicus*, *Dermacentor variabilis*, *Ixodes ovatus*, *Ixodes persulcatus*, *Ixodes scapularis*, *Amblyomma americanum*, *Boophilus microplus*, or *Rhipicephalus sanguineus*),
   Acaridae (for example, *Tyrophagus putrescentiae* or *Tyrophagus similis*),
   Pyroglyphidae (for example, *Dermatophagoides farinae* or *Dermatophagoides ptrenyssnus*).
   and the others.

The agent for controlling harmful arthropods of the present invention comprises the compound of the present invention and an inert carrier. The agent for controlling harmful arthropods of the present invention is usually prepared by mixing the compound of the present invention with an inert active carrier such as solid carrier, liquid carrier, or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations, tablets, or the others. Such formulations may be processed into mosquito repellent coils, electric mosquito repellent mats, liquid mosquito formulations, smoking agents, fumigants, sheet formulations, spot-on formulations, or formulations for oral treatment. Also, the agent for controlling harmful arthropods of the present invention may be mixed with other pesticides, miticides, nematicides, fungicides, plant growth regulators, herbicides, or synergists.

The agent for controlling harmful arthropods of the present invention comprises usually 0.01 to 95% by weight of the compound of the present invention.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica), chemical fertilizers (for example, ammonium sulfate, ammonium phosphate, ammonium nitrate, urea, or ammonium chloride), and the others; as well as synthetic resins (for Example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the above-mentioned liquid carriers include water; alcohols (for example, methanol, ethanol, isopropyl alcohol, butanol, hexanol, benzyl alcohol, ethylene glycol, propylene glycol, or phenoxy ethanol); ketones (for Example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether, or 3-methoxy-3-methyl-1-butanol); acid amides (for example, N,N-dimethylformamide or N,N-dimethylacetamide); halogenated hydrocarbons (for example, dichloromethane, trichloroethane, or carbon tetrachloride); sulfoxides (for example, dimethyl sulfoxide); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates, and alkyl sulfates.

Examples of the other auxiliary agents for formulation include a binder, a dispersant, a colorant, and a stabilizer. Specific examples include casein, gelatin, polysaccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of base material of the resin formulation include polyvinyl chloride polymers, polyurethane, and the others, and a plasticizer such as phthalate esters (for example, dimethyl phthalate or dioctyl phthalate), adipic acid esters, and stearic acid may be added to these base materials, if necessary. The resin formulation can be prepared by mixing the compound of the present invention with the above-mentioned base material, kneading the mixture in a kneading apparatus, followed by molding it by injection molding, extrusion molding, pressure molding, or the like. The resultant resin formulation can be subjected to further molding, cutting procedure, or the like, if necessary, to be processed into shapes such as a plate, film, tape, net, and string shape. These resin formulations can be processed into animal collars, animal ear tags, sheet products, trap strings, gardening supports, or other products.

Examples of a base material for the poison baits include bait ingredients such as grain powder, vegetable oil, saccharide, and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor, and peanut oil, or the other ingredient.

The method for controlling harmful arthropods of the present invention is conducted by applying an effective amount of the compound of the present invention to a harmful arthropod directly and/or a habitat thereof (for example, plant bodies, soil, an interior of a house, or animal bodies). In the method for controlling harmful arthropods of the present invention, the compound of the present invention is usually used in the form of a harmful arthropod controlling agent.

When an agent for controlling harmful arthropods of the present invention is used for controlling harmful arthropods in an agricultural field, the application dose as an amount of the compound of the present invention is usually within a range from 1 to 10,000 g per 10,000 $m^2$. The emulsifiable concentrate, the wettable powder, or the flowable formulation etc. of an agent for controlling harmful arthropods of the present invention is usually applied by diluting it with water in such a way that a concentration of the active ingredient is within a range from 0.01 to 10,000 ppm. The granular formulation or the dust formulation etc., is usually applied as itself without diluting it.

These formulations and diluents of the formulations with water may be directly sprayed to a harmful arthropod or a plant such as a crop to be protected from a harmful arthropod, or applied to a soil in a cultivated area to control a harmful arthropod that inhabits the soil.

Also, a resin formulation processed into sheet shape or string shape may be wrapped around a crop, stretched near a crop, spread on a plant foot soil, or the like.

When the agent for controlling harmful arthropods of the present invention is used to control harmful arthropods that live inside a house, the application dose as an amount of the compound of the present invention is usually within a range from 0.01 to 1,000 mg per 1 $m^2$ of an area to be treated, in the case of using it on a planar area. In the case of using it spatially, the application dose as an amount of the compound of the present invention is usually within a range from 0.01 to 500 mg per 1 $m^3$ of the space to be treated. When the agent for controlling harmful arthropods of the present invention is formulated into emulsifiable concentrates, wettable powders, flowables, or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits, or the others, such formulations are used as itself without diluting it.

When the agent for controlling harmful arthropods of the present invention is used for controlling external parasites of livestock such as cows, horses, pigs, sheep, goats, and chickens, and small animals such as dogs, cats, rats, and mice, the pest control agent of the present invention can be applied to the animals by a known method in the veterinary field. Specifically, when systemic control is intended, the pest control agent of the present invention is administered to the animals as a tablet, a mixture with feed, or a suppository, or by injection (including intramuscular, subcutaneous, intravenous, and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the compound of the present invention is usually within a range from 0.1 to 1,000 mg per 1 kg of an animal body weight.

EXAMPLES

The following Examples including Preparation examples, Formulation examples, and Test examples, serve to illustrate the present invention in more detail, which should not intend to limit the present invention.

First, regarding the preparation of the compound of the present invention, the Preparation Examples are shown below.

Preparation Example 1(1)

A mixture of 4-chloro-6-methoxypyrimidine 1.28 g, [2-fluoro-4-(trifluoromethyl)phenyl]-boronic acid pinacol ester 1.48 g, tetrakis(triphenylphosphine)palladium(0) 0.28 g, an aqueous sodium carbonate solution (2M) 6.3 ml, and 1,2-dimethoxyethane (hereinafter referred to as "DME") 15 ml was stirred at 80° C. for 3 hours. When the reaction was completed, the resulting reaction mixtures were allowed to stand to room temperature, and to the mixtures was added water, and the mixtures were extracted with ethyl acetate, and then the organic layers were dried over anhydrous sodium sulfate. The organic layers were concentrated under reduced pressure, and then the resulting residues were subjected to a silica gel column chromatography to give an intermediate compound (1-1) 0.99 g.

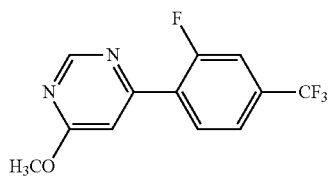 [SMILES: COc1cc(-c2ccc(C(F)(F)F)cc2F)ncn1]

$^1$H-NMR (CDCl$_3$) δ: 8.89 (1H, s), 8.28 (1H, dd), 7.56 (1H, d), 7.46 (1H, d), 7.29 (1H, s), 4.05 (3H, s).

Preparation Example 1(2)

To a reaction mixture of the intermediate compound (1-1) 0.97 g and NMP 15 ml were added successively ethanethiol 0.29 ml and sodium hydride (oily, 60%) 0.17 g under ice-cooling, and the resulting mixtures were stirred at room temperature for one day. To the reaction mixtures was added water, and the precipitated solids were collected by filtration, and the resulting filtrate was concentrated under reduced pressure to give an intermediate compound (1-2) 1.03 g.

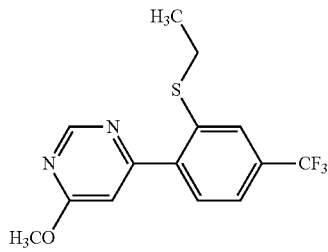 [SMILES: CCSc1cc(C(F)(F)F)ccc1-c1cc(OC)ncn1]

$^1$H-NMR (CDCl$_3$) δ: 8.90 (1H, s), 7.61-7.55 (2H, m), 7.49 (1H, d), 7.01 (1H, s), 4.06 (3H, s), 2.95 (2H, q), 1.30 (3H, t).

Preparation Example 1(3)

To a mixture of the intermediate compound (1-2) 0.98 g and chloroform 15 ml was added mCPBA (70%) 1.58 g under ice-cooling, and the resulting mixtures were stirred at room temperature for 1.5 hours. To the resulting reaction mixtures were added a 10% aqueous sodium thiosulfate solution, and the mixtures were extracted with chloroform. The organic layers were washed with a saturated aqueous sodium hydrogen carbonate solution, the organic layers were dried over anhydrous sodium sulfate, and then the organic layers were concentrated under reduced pressure. The resulting residues were subjected to a silica gel column chromatography to give an intermediate compound (1-3) 0.91 g.

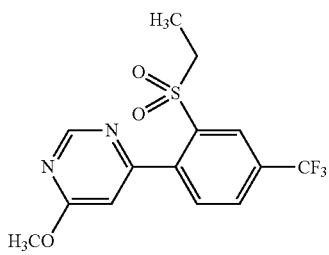 [SMILES: CCS(=O)(=O)c1cc(C(F)(F)F)ccc1-c1cc(OC)ncn1]

$^1$H-NMR (CDCl$_3$) δ: 8.80 (1H, s), 8.42 (1H, s), 7.97 (1H, d), 7.59 (1H, d), 6.89 (1H, s), 4.06 (3H, s), 3.68 (2H, q), 1.34 (3H, t).

Preparation Example 1(4)

A mixture of the intermediate compound (1-3) 0.86 g and concentrated hydrochloric acid 10 ml was heated under reflux with stirring for 2 hours. The resulting reaction mixtures were allowed to stand to room temperature and poured into water, and to the mixtures were added sodium hydroxide. The precipitated solids were collected by filtration and concentrated under reduced pressure to give an intermediate compound (1-4) 0.74 g.

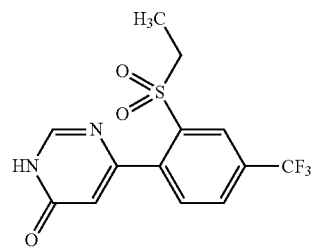 [SMILES: CCS(=O)(=O)c1cc(C(F)(F)F)ccc1-c1cc(=O)[nH]cn1]

$^1$H-NMR (CDCl$_3$) δ: 8.40 (1H, s), 8.17 (1H, s), 7.99 (1H, d), 7.64 (1H, d), 6.64 (1H, s), 3.67 (2H, q), 1.37 (3H, t).

Preparation Example 1(5)

To a mixture of the intermediate compound (1-4) 0.23 g, cesium carbonate 0.27 g, and NMP 3 ml was added 2,2,2-trifluoroethyl nonafluorobutanesulfonate 0.29 g at room temperature, and the resulting mixtures were stirred at room temperature for 3 hours. To the reaction mixtures was added water, and the mixtures were extracted with ethyl acetate, and then the organic layers were dried over anhydrous sodium sulfate. The organic layers were concentrated under reduced pressure, and then the resulting residues were subjected to a silica gel column chromatography to give a present compound 1 0.14 g and the by-product 1 0.13 g.

Present compound 1

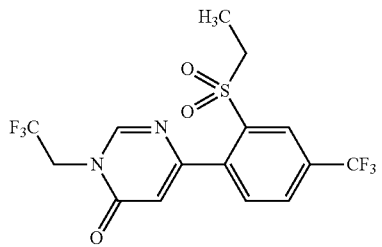

¹H-NMR (CDCl₃) δ: 8.38 (1H, s), 8.15 (1H, s), 7.99 (1H, d), 7.64 (1H, d), 6.65 (1H, s), 4.67 (2H, q), 3.65 (2H, q), 1.36 (3H, t)

By-product 1

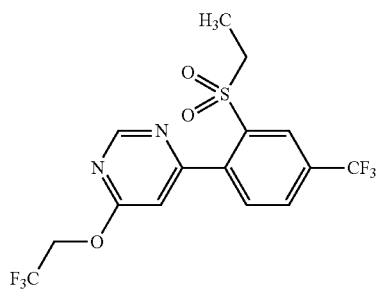

¹H-NMR (CDCl₃) δ: 8.82 (1H, s), 8.43 (1H, s), 8.00 (1H, d), 7.61 (1H, d), 7.03 (1H, s), 4.88 (2H, q), 3.68 (2H, q), 1.35 (3H, t).

Preparation Example 2

A present compound 2 and a by-product 2 were prepared by using 2,2,3,3,3-pentafluoropropyl trifluoromethanesulfonate instead of 2,2,2-trifluoroethyl nonafluorobutanesulfonate according to the method described in the Preparation example 1(5).

Present compound 2

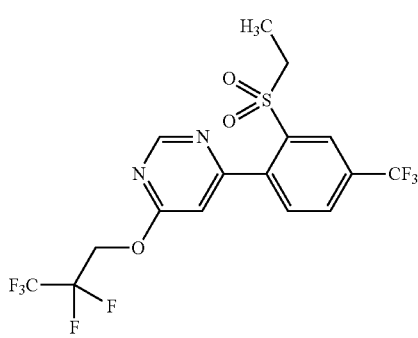

¹H-NMR (CDCl₃) δ: 8.39 (1H, s), 8.14 (1H, s), 7.99 (1H, d), 7.65 (1H, d), 6.65 (1H, s), 4.69 (2H, t), 3.65 (2H, q), 1.37 (3H, t).

By-product 2

¹H-NMR (CDCl₃) δ: 8.82 (1H, s), 8.43 (1H, s), 7.99 (1H, d), 7.61 (1H, d), 7.03 (1H, s), 4.95 (2H, t), 3.69 (2H, q), 1.36 (3H, t).

Preparation Example 3

A present compound 3 and a by-product 3 were prepared by using 2,2,3,4,4,4-hexafluorobutyl trifluoromethanesulfonate instead of 2,2,2-trifluoroethyl nonafluorobutanesulfonate according to the method described in the Preparation example 1(5).

Present compound 3

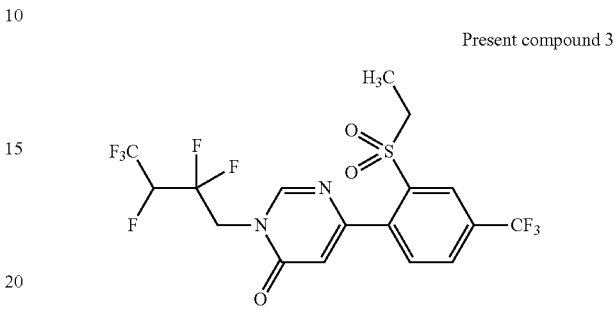

¹H-NMR (CDCl₃) δ: 8.39 (1H, s), 8.14 (1H, s), 7.99 (1H, d), 7.64 (1H, d), 6.65 (1H, s), 5.19-4.98 (1H, m), 4.77-4.50 (2H, m), 3.65 (2H, q), 1.37 (3H, t).

By-product 3

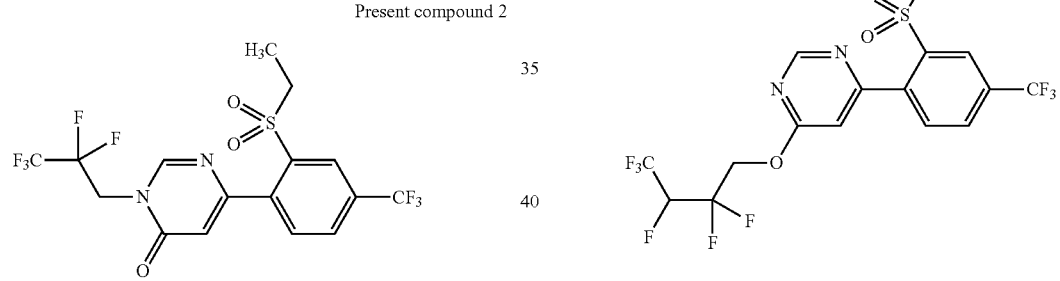

¹H-NMR (CDCl₃) δ: 8.83 (1H, s), 8.43 (1H, s), 8.00 (1H, d), 7.60 (1H, d), 7.01 (1H, s), 5.20-5.02 (1H, m), 4.90-4.82 (2H, m), 3.68 (2H, q), 1.35 (3H, t).

Preparation Example 4(1)

An intermediate compound (4-1) was prepared by using 4-chloro-6-methoxy-5-methylpyrimidine instead of 4-chloro-6-methoxypyrimidine according to the method described in the Preparation example 1(1).

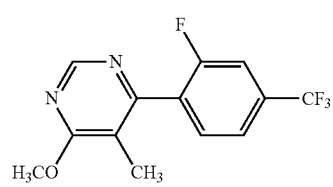 [SMILES: COc1ncnc(-c2ccc(C(F)(F)F)cc2F)c1C]

¹H-NMR (CDCl₃) δ: 8.72 (1H, s), 7.63-7.57 (1H, m), 7.55 (1H, d), 7.44 (1H, d), 4.07 (3H, s), 2.08 (3H, d).

Preparation Example 4(2)

An intermediate compound (4-2) was prepared by using the intermediate compound (4-1) instead of the intermediate compound (1-1) according to the method described in the Preparation example 1(2).

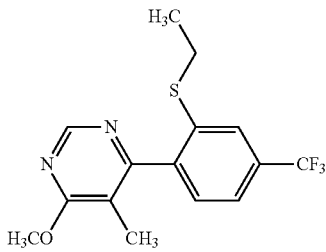 [SMILES: CCSc1cc(C(F)(F)F)ccc1-c1ncnc(OC)c1C]

¹H-NMR (CDCl₃) δ: 8.71 (1H, s), 7.59 (1H, s), 7.49 (1H, d), 7.29 (1H, d), 4.07 (3H, s), 2.91 (2H, q), 1.98 (3H, s), 1.27 (3H, t).

Preparation Example 4(3)

An intermediate compound (4-3) was prepared by using the intermediate compound (4-2) instead of the intermediate compound (1-2) according to the method described in the Preparation example 1(3).

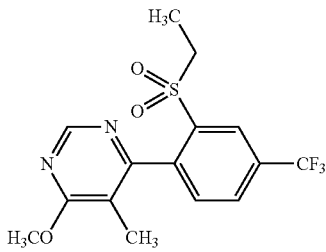 [SMILES: CCS(=O)(=O)c1cc(C(F)(F)F)ccc1-c1ncnc(OC)c1C]

¹H-NMR (CDCl₃) δ: 8.63 (1H, s), 8.41 (1H, s), 7.97 (1H, d), 7.47 (1H, d), 4.07 (3H, s), 3.51-3.27 (2H, m), 1.96 (3H, s), 1.27 (3H, t).

Preparation Example 4(4)

A mixture of the intermediate compound (4-3) 0.98 g and concentrated hydrochloric acid 5 ml was heated under reflux with stirring for 1 hour. The reaction mixtures were allowed to stand to room temperature and then poured into water, and the mixtures were extracted with methyl-tert-butyl ether, and the organic layers were dried over anhydrous sodium sulfate. The organic layers were concentrated under reduced pressure to give an intermediate compound (4-4) 0.83 g.

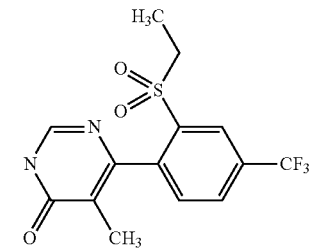 [SMILES: CCS(=O)(=O)c1cc(C(F)(F)F)ccc1-c1nc[nH]c(=O)c1C]

¹H-NMR (CDCl₃) δ: 8.41 (1H, s), 8.10 (1H, s), 7.99 (1H, d), 7.52 (1H, d), 3.53-3.32 (2H, m), 1.94 (3H, s), 1.31 (3H, t).

Preparation Example 4(5)

A present compound 4 and a by-product 4 were prepared by using the intermediate compound (4-3) instead of the intermediate compound (1-3), and using 2,2,3,3,3-pentafluoropropyl trifluoromethanesulfonate instead of 2,2,2-trifluoroethyl nonafluorobutanesulfonate according to the method described in the Preparation example 1(5).

Present compound 4

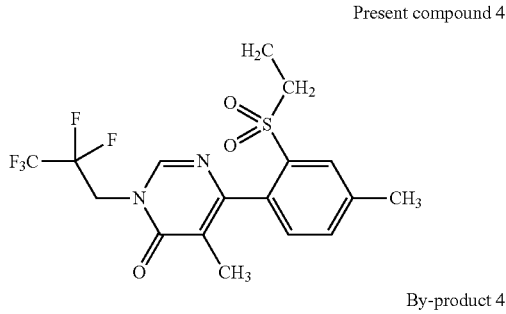

By-product 4

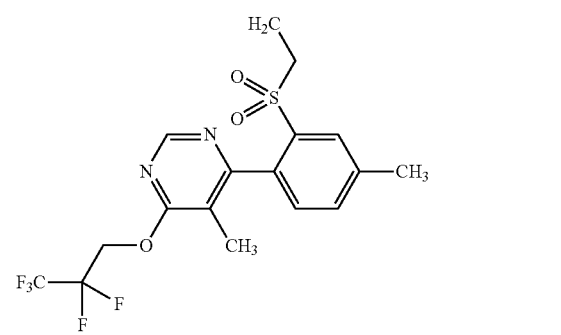

¹H-NMR (CDCl₃) δ: 8.65 (1H, s), 8.42 (1H, s), 7.99 (1H, d), 7.48 (1H, d), 5.17-4.96 (1H, m), 4.89-4.69 (1H, m), 3.52-3.25 (2H, m), 2.01 (3H, s), 1.28 (3H, t).

Preparation Example 5

A present compound 5 and a by-product 5 were prepared by using the intermediate compound (4-3) instead of the intermediate compound (1-3), and using 2,2,3,4,4,4-hexafluorobutyl trifluoromethanesulfonate instead of 2,2,2-trifluoroethyl nonafluorobutanesulfonate according to the method described in the Preparation example 1(5).

Present compound 5

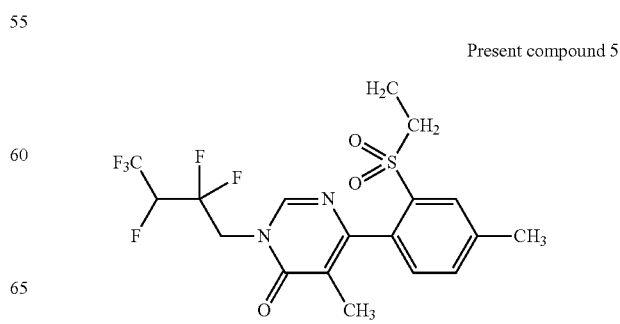

-continued

By-product 5

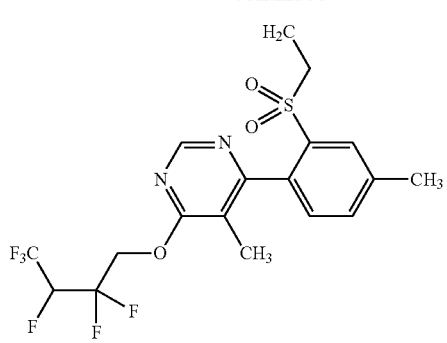

¹H-NMR (CDCl₃) δ: 8.65 (1H, s), 8.42 (1H, s), 8.00 (1H, d), 7.48 (1H, d), 5.18-4.69 (3H, m), 3.51-3.26 (2H, m), 2.01 (3H, s), 1.28 (3H, t).

Preparation Example 6(1)

To a mixture of 4,6-dichloropyrimidine 6 g and methanol 40 mL was added dropwise a 28% sodium methoxide solution in methanol 8.16 g under ice-cooling. The resulting mixtures were stirred for 2 hours under ice-cooling and then warmed to room temperature, and stirred for 6 hours. The reaction mixtures were concentrated under reduced pressure, and to the resulting oily materials was added a saturated aqueous ammonium chloride solution, and then the resulting mixtures were extracted with ethyl acetate. The organic layers were washed with saturated brine, and then the organic layers were dried over sodium sulfate. The organic layers were concentrated under reduced pressure, and the resulting oily materials were subjected to a silica gel chromatography to give an intermediate compound (6-1) 4.6 g.

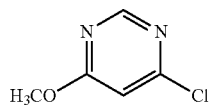

¹H-NMR (CDCl₃) δ: 8.59 (1H, s), 6.78 (1H, dd), 4.01-3.95 (3H, m).

Preparation Example 6(2)

To a mixture of 1,4-diazabicyclo[2,2,2]octane 6.9 g and methyl-tert-butyl ether was added dropwise 1.0 M n-butyllithium solution in hexane 39 mL under cooling to −40° C. The reaction mixtures were stirred at −40° C. for 2 hours and then cooled to −50° C., and to the reaction mixtures was added dropwise 3-fluoropyridine 5.0 g. The resulting mixtures were stirred at −50° C. for additional 2 hours, and then to the reaction mixtures was added dropwise tributylstannyl chloride 17 mL. The reaction mixtures were stirred at −50° C. for 6 hours and then warmed to room temperature, and to the mixtures was added a saturated aqueous ammonium chloride solution. The reaction mixtures were extracted with methyl-tert-butyl ether. The organic layers were washed with saturated brine, and then the organic layers were dried over anhydrous sodium sulfate. The organic layers were concentrated under reduced pressure to give a mixture 23 g comprising an intermediate compound (6-2).

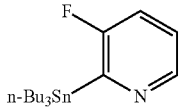

¹H-NMR (CDCl₃) δ: 8.62-8.56 (1H, m), 7.25-7.11 (2H, m), 1.69-0.76 (45H, m).

Preparation Example 6(3)

To a mixture of the mixture 6.0 g comprising the intermediate compound (6-2), the intermediate compound (6-1) 1.0 g, and toluene 28 mL were added tetrakis(triphenylphosphine)palladium 810 mg, copper iodide 130 mg, and anhydrous lithium chloride 430 mg under room temperature. The reaction mixtures were heated under reflux with stirring for 6 hours. The reaction mixtures were allowed to stand to room temperature, and to the mixture was added the intermediate compound (6-1) 500 mg. The reaction mixtures were heated under reflux with stirring for additional 9 hours. The reaction mixtures were allowed to stand to room temperature, and then to the mixture was added a saturated aqueous sodium hydrogen carbonate solution, and the mixtures were extracted with chloroform. The organic layers were dried over anhydrous sodium sulfate. The organic layers were concentrated under reduced pressure, and the resulting residues were subjected to a silica gel chromatography to give an intermediate compound (6-3) 960 mg.

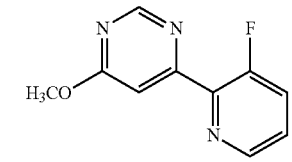 [SMILES: COc1cc(-c2ncccc2F)ncn1]

¹H-NMR (CDCl₃) δ: 8.97 (1H, d), 8.63-8.60 (1H, m), 7.61-7.55 (1H, m), 7.47-7.42 (2H, m), 4.06 (3H, s).

Preparation Example 6(4)

To a mixture of the intermediate compound (6-3) 1.4 g and DMF 22 mL were added successively sodium hydride (60%, oily) 290 mg and ethanethiol 510 μL under ice-cooling. The resulting mixtures were stirred under room temperature for 3 hours, and then to the reaction mixtures was added a saturated aqueous sodium hydrogen carbonate solution. The reaction mixtures were extracted with ethyl acetate. The organic layers were washed with water and saturated brine, and the organic layers were dried over anhydrous sodium sulfate. The organic layers were concentrated under reduced pressure to give an intermediate compound (6-4) 1.7 g.

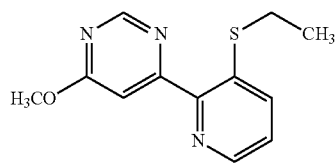 [SMILES: CCSc1cccnc1-c1cc(OC)ncn1]

¹H-NMR (CDCl₃) δ: 8.92 (1H, d), 8.46 (1H, dd), 7.72 (1H, dd), 7.36 (1H, d), 7.33-7.29 (1H, m), 4.05 (3H, s), 2.93 (2H, q), 1.33 (3H, t).

Preparation Example 6(5)

An intermediate compound (6-5) was prepared by using the intermediate compound (6-4) instead of the intermediate compound (1-2) according to the method described in the Preparation example 1(3).

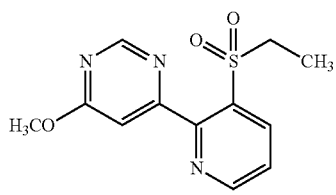 [SMILES: CCS(=O)(=O)c1cccnc1-c1cc(OC)ncn1]

¹H-NMR (CDCl₃) δ: 8.90 (1H, dd), 8.80 (1H, d), 8.48 (1H, dd), 7.61 (1H, dd), 7.18 (1H, d), 4.05 (3H, s), 3.92 (2H, q), 1.38 (3H, t).

Preparation Example 6(6)

A mixture of the intermediate compound (6-5) 1.8 g and 12N hydrochloric acid 10 mL was heated at 90° C. with stirring for 6 hours, and then the mixtures were concentrated under reduced pressure. To the resulting residues was added ethanol, and the precipitated solids were filtered and washed with ethanol to give an intermediate compound (6-6) 1.6 g.

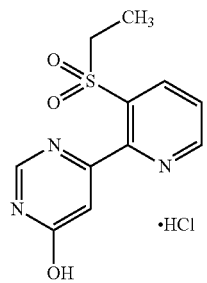 [SMILES: CCS(=O)(=O)c1cccnc1-c1cc(O)ncn1 ; Cl]

¹H-NMR (DMSO-D₆) δ: 8.94 (1H, dd), 8.41 (1H, dd), 8.32 (1H, d), 7.81 (1H, dd), 6.59 (1H, d), 3.79 (2H, q), 1.20 (3H, t).

Preparation Example 6(7)

To a mixture of the intermediate compound (6-6) 150 mg and chloroform 4 mL were added successively diisopropylethylamine 260 μL and 2,2,2-trifluoroethyl trifluoromethanesulfonate 140 μL under room temperature. The reaction mixtures were heated at 75° C. with stirring for 2 hours. The resulting reaction mixtures were allowed to stand to room temperature, and then to the mixtures was added a saturated aqueous sodium hydrogen carbonate solution, and the mixtures were extracted with ethyl acetate. The organic layers were washed with saturated brine, and then the organic layers were dried over anhydrous sodium sulfate. The organic layers were concentrated under reduced pressure, and the resulting residues were subjected to a silica gel chromatography to give a present compound 6 130 mg.

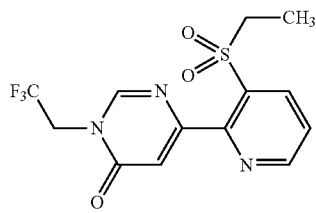 [SMILES: CCS(=O)(=O)c1cccnc1-c1cc(=O)n(CC(F)(F)F)cn1]

Preparation Example 7

A present compound 7 was prepared by using 2,2,3,3,3-pentafluoropropyl trifluoromethanesulfonate instead of 2,2,2-trifluoroethyl trifluoromethanesulfonate according to the method described in the Preparation example 6(7).

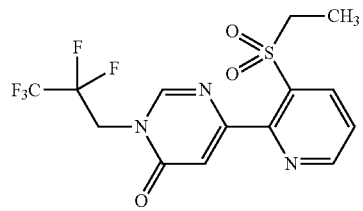 [SMILES: CCS(=O)(=O)c1cccnc1-c1cc(=O)n(CC(F)(F)C(F)(F)F)cn1]

Preparation Example 8

A present compound 8 and a by-product 8 were prepared by using 2,2,3,3-tetrafluoropropyl trifluoromethanesulfonate instead of 2,2,2-trifluoroethyl trifluoromethanesulfonate according to the method described in the Preparation example 6(7).

Present compound 8

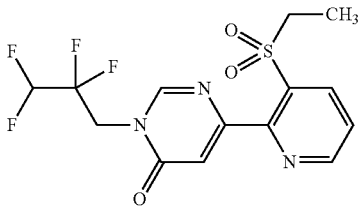

By-product 8

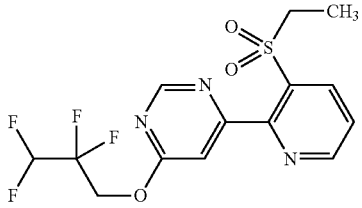

¹H-NMR (CDCl₃) δ: 8.90 (1H, dd), 8.83 (1H, d), 8.49 (1H, dd), 7.64 (1H, dd), 7.32 (1H, d), 6.16-5.85 (1H, m), 4.91-4.82 (2H, m), 3.92 (2H, q), 1.39 (3H, t).

Preparation Example 9

A present compound 9 and a by-product 9 were prepared by using 2,2,3,4,4,4-hexafluorobutyl trifluoromethanesulfonate instead of 2,2,2-trifluoroethyl trifluoromethanesulfonate according to the method described in the Preparation example 6(7).

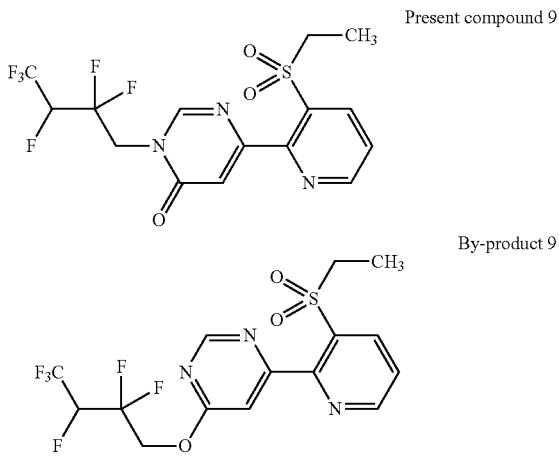

Present compound 9

By-product 9

¹H-NMR (CDCl₃) δ: 8.91 (1H, dd), 8.83 (1H, d), 8.50 (1H, dd), 7.64 (1H, dd), 7.32 (1H, d), 5.21-5.00 (1H, m), 4.90-4.81 (2H, m), 3.92 (2H, q), 1.40 (3H, t).

Preparation Example 10

A present compound 10 was prepared by using 2,2,3,3,4,4,5,5-octafluoropentyl trifluoromethanesulfonate instead of 2,2,2-trifluoroethyl trifluoromethanesulfonate according to the method described in the Preparation example 6(7).

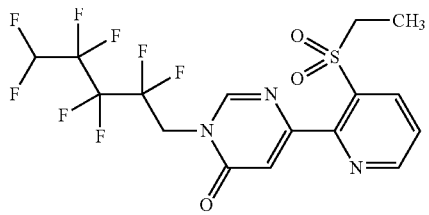 [SMILES: CCS(=O)(=O)c1cccnc1-c1cc(=O)n(CC(F)(F)C(F)(F)C(F)(F)C(F)F)cn1]

Preparation Example 11

A present compound 11 was prepared by using 4,4,4-trifluorobutyl iodide instead of 2,2,2-trifluoroethyl trifluoromethanesulfonate according to the method described in the Preparation example 6(7).

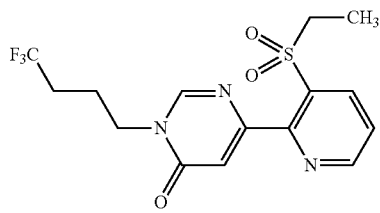 [SMILES: CCS(=O)(=O)c1cccnc1-c1cc(=O)n(CCCC(F)(F)F)cn1]

Preparation Example 12(1)

To a mixture of 3-chloropyridine-2-carbonitrile 54 g and THF 300 mL was added dropwise 1M methylmagnesium bromide solution in THF 500 g under ice-cooling. The reaction mixtures were stirred under ice-cooling for 2 hours. To 2N hydrochloric acid was added the resulting reaction mixtures under ice-cooling, and the mixtures were stirred for 30 minutes. The mixtures were made pH 8 with a 1N aqueous sodium hydroxide solution, and then the mixtures were extracted with ethyl acetate. The organic layers were washed with saturated brine, and then the organic layers were dried over anhydrous sodium sulfate. The organic layers were concentrated under reduced pressure to give an intermediate compound (12-1) 58 g.

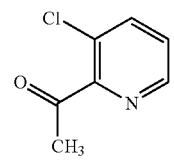

¹H-NMR (CDCl₃) δ: 8.55 (1H, dd), 7.80 (1H, dd), 7.38 (1H, dd), 2.70 (3H, s).

Preparation Example 12(2)

To a suspension of sodium hydride (oily, 60%) 57 g and DMF 560 mL was added dropwise ethanethiol 100 mL under ice-cooling. To the resulting mixtures was added dropwise a mixed solution of the intermediate compound (12-1) 204 g and DMF 190 mL under ice-cooling. The resulting reaction mixtures were stirred under ice-cooling for 1 hour, and then added to ice water. The precipitated solids were filtered and washed with water. The resulting solids were dissolved into ethyl acetate, and the resulting solution was washed with saturated brine, and then the organic layers were dried over sodium sulfate. The resulting organic layers were concentrated under reduced pressure, and then the resulting solids were washed with hexane to give an intermediate compound (12-2) 160 g.

¹H-NMR (CDCl₃) δ: 8.40 (1H, dd), 7.69 (1H, dd), 7.37 (1H, dd), 2.92 (2H, q), 2.72 (3H, s), 1.40 (3H, t).

Preparation Example 12(3)

To a mixture of the intermediate compound (12-2) 3.6 g and dimethyl carbonate 20 mL was added sodium hydride (oily, 60%) under ice-cooling, and the resulting mixtures were stirred for 30 minutes. The reaction mixtures were heated to 50° C. and stirred for 4 hours. The reaction mixtures were allowed to stand to room temperature, and then added to 0.5N hydrochloric acid, and the resulting mixtures were extracted with ethyl acetate. The organic layers were washed with water, and then the organic layers were dried over anhydrous sodium sulfate. The organic layers were concentrated under reduced pressure, and the resulting solids were washed with a mixed solvent of methyl-tert-butyl ether/hexane (1:10) to give an intermediate compound (12-3) 4.6 g.

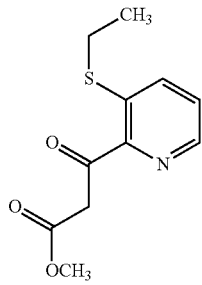 [SMILES: CCSc1cccnc1C(=O)CC(=O)OC]

¹H-NMR (CDCl₃) δ: 8.38 (1H, dd), 7.69 (1H, d), 7.38 (1H, dd), 4.19 (2H, s), 3.72 (3H, s), 2.93 (2H, q), 1.41 (3H, t).

Preparation Example 12(4)

To a mixture of the intermediate compound (12-3) 4.6 g and formamide 38 mL was added ammonium acetate 7.3 g under room temperature. The reaction mixtures were heated at 100° C. with stirring for 4 hours, and then allowed to stand to room temperature. To the resulting reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting solids were washed with a mixed solvent of methyl-tert-butyl ether/hexane (1:10) to give an intermediate compound (12-4) 3.7 g.

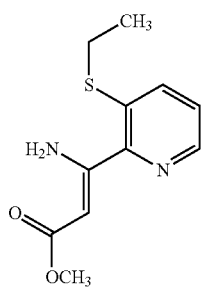 [SMILES: CCSc1cccnc1/C(N)=C/C(=O)OC]

¹H-NMR (CDCl₃) δ: 8.39 (1H, d), 7.65 (1H, d), 7.26 (1H, dd), 5.21 (1H, s), 3.73 (3H, s), 2.94 (2H, q), 1.34 (3H, t).

Preparation Example 12(5)

To a mixture of the intermediate compound (12-4) 5.0 g and NMP 21 mL was added a 28% sodium methoxide solution in methanol 20 g under ice-cooling. The reaction mixtures were heated at 100° C. with stirring for 2 hours, and then allowed to stand to room temperature. To the reaction mixtures was added a 1N aqueous sodium hydroxide solution under ice-cooling, and the resulting mixtures were washed with chloroform. The resulting aqueous layers were made pH 4 with 6N hydrochloric acid, and then extracted with chloroform. The organic layers were dried over anhydrous sodium sulfate. The organic layers were concentrated under reduced pressure, and the resulting solids were washed with methyl-tert-butyl ether to give an intermediate compound (12-5) 4.2 g.

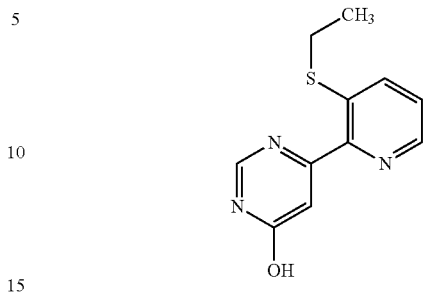

¹H-NMR (CDCl₃) δ: 8.48 (1H, dd), 8.30 (1H, s), 7.72 (1H, d), 7.32 (1H, dd), 7.05 (1H, s), 2.94 (2H, q), 1.35-1.32 (3H, m).

Preparation Example 12(6)

To a mixture of the intermediate compound (12-5) 12 g and chloroform 170 mL was added mCPBA (70%) 25 g under ice-cooling. The reaction mixtures were stirred under ice-cooling for 3 hours, and then to the mixtures was added chloroform 350 mL. The reaction mixtures were extracted with 4N hydrochloric acid. The aqueous layers were washed with a mixed solution of dimethylsulfide-chloroform (1:100), and the aqueous layers were dried under reduced pressure. To the resulting residues was added ethanol, and the precipitated solids were filtered and washed with ethanol to give an intermediate compound (12-6) 12 g.

Preparation Example 12(7)

To a mixture of the intermediate compound (12-6) 400 mg and chloroform 3 mL were added successively diisopropylethylamine 930 μL, 4-dimethylaminopyridine 32 mg, and 1,1,3-trichloro-1-propene 580 mg under room temperature. The reaction mixtures were heated at 50° C. with stirring for 3 hours. The reaction mixtures were allowed to stand to room temperature, and then to the mixtures was added water, and the mixtures were extracted with chloroform. The organic layers were dried over anhydrous sodium sulfate. The organic layers were concentrated under reduced pressure, and the resulting residues were subjected to a silica gel chromatography to give a present compound 12 370 mg.

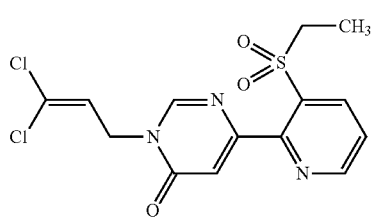 [SMILES: CCS(=O)(=O)c1cccnc1-c1cc(=O)n(CC=C(Cl)Cl)cn1]

Preparation Example 13(1)

To a mixture of 3, 6-dichloropyridine-2-carboxylic acid 10 g and toluene 52 mL was added thionyl chloride 9.8 mL under room temperature. The reaction mixtures were heated at 110° C. with stirring for 4 hours. The reaction mixtures were allowed to stand to room temperature, and then concentrated under reduced pressure to give oily materials.

Preparation Example 13(2)

To a mixture of anhydrous magnesium chloride 6.9 g and THF 104 mL was added potassium methyl malonate 11 g under room temperature. The reaction mixtures were stirred under room temperature for 2 hours. To the reaction mixtures were added successively the whole amount of the oily materials obtained in the above Preparation example 13(1) and triethylamine 14 mL under ice-cooling. The reaction mixtures were warmed to room temperature, and stirred at room temperature for 12 hours. To the resulting reaction mixtures was added 2N hydrochloric acid 300 mL under ice-cooling, and the mixtures were stirred under room temperature for 3 hours. The resulting reaction mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give an intermediate compound (13-2) 7.9 g.

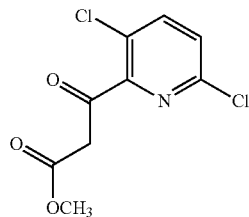 [SMILES: COC(=O)CC(=O)c1nc(Cl)ccc1Cl]

$^1$H-NMR (CDCl$_3$) δ: 7.79 (1H, d), 7.43 (1H, d), 4.13 (2H, s), 3.74 (3H, s).

Preparation Example 13(3)

An intermediate compound (13-3) was prepared by using the intermediate compound (13-2) instead of the intermediate compound (12-3) according to the method described in the Preparation example 12(4).

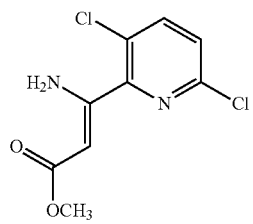 [SMILES: COC(=O)/C=C(\N)c1nc(Cl)ccc1Cl]

$^1$H-NMR (CDCl$_3$) δ: 7.75 (1H, d), 7.31 (1H, d), 5.41 (1H, s), 3.73 (3H, s).

Preparation Example 13(4)

To a mixture of the intermediate compound (13-3) 2.4 g and NMP 23 mL were added successively sodium hydride (60%, oily) 840 mg and ethanethiol 1.6 mL under ice-cooling. The reaction mixtures were warmed to room temperature, and then stirred for 6 hours. To the resulting reaction mixtures was added a saturated aqueous sodium hydrogen carbonate solution, and the mixtures were extracted with ethyl acetate. The organic layers were washed successively with water and saturated brine, and the organic layers were dried over anhydrous sodium sulfate. The organic layers were dried under reduced pressure, and the resulting residues were subjected to a silica gel chromatography to give an intermediate compound (13-4) 2.7 g.

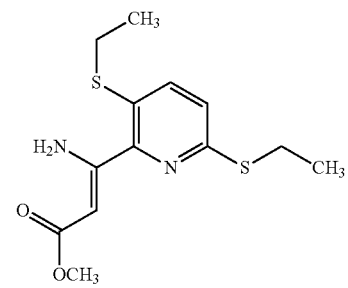 [SMILES: CCSc1ccc(SCC)c(/C(N)=C/C(=O)OC)n1]

$^1$H-NMR (CDC$_3$) δ: 7.50 (1H, d), 7.12 (1H, dd), 5.27 (1H, s), 3.73 (3H, s), 3.16 (2H, q), 2.89 (2H, q), 1.38 (3H, t), 1.28 (3H, t).

Preparation Example 13(5)

To a mixture of the intermediate compound (13-4) 2.7 g, formamide 1.8 mL, and NMP 18 mL was added sodium hydride (60%, oily) 1.4 g under ice-cooling. The reaction mixtures were heated at 100° C. with stirring for 4 hours. The reaction mixtures were allowed to stand to room temperature, and then made pH 4 with 2N hydrochloric acid. The precipitated solids were filtered, and washed with hydrochloric acid which was used in making pH 4 to give a mixture 2.7 g comprising an intermediate compound (13-5).

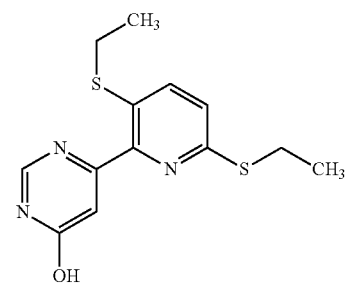 [SMILES: CCSc1ccc(SCC)c(-c2cc(O)ncn2)n1]

$^1$H-NMR (CDCl$_3$) δ: 8.30 (1H, s), 7.54 (1H, d), 7.18 (1H, d), 7.16 (1H, s), 3.21 (2H, q), 2.89 (2H, q), 1.39 (3H, t), 1.31 (3H, t).

Preparation Example 13(6)

To a mixture of the mixture 2.7 g comprising the intermediate compound (13-5) prepared in the above Preparation example 13(5) and chloroform 19 mL were added successively 2,2,3,4,4,4-hexafluorobutyl trifluoromethanesulfonate 4.4 g and diisopropylethylamine 3.3 mL under ice-cooling. The reaction mixtures were stirred at 50° C. for 10 hours. The reaction mixtures were allowed to stand to room temperature, and to the mixtures was added 2N hydrochloric acid, and the mixtures were extracted with chloroform. The organic layers were washed with water and saturated brine, and then the organic layers were dried over anhydrous sodium sulfate. The organic layers were concentrated under reduced pressure, and the resulting residues were subjected to a silica gel chromatography to give a present compound 13 2.6 g.

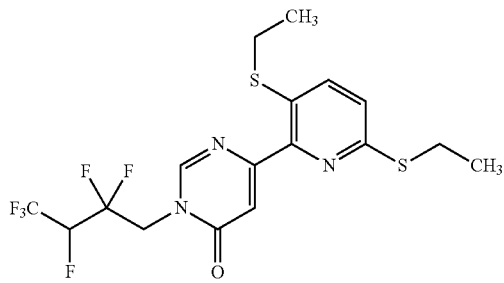 [SMILES: CCSc1ccc(SCC)c(-c2cc(=O)n(CC(F)(F)C(F)C(F)(F)F)cn2)n1]

Preparation Example 14

To a mixture of the present compound 13 2.6 g and chloroform 28 mL was added mCPBA (70%) 5.3 g under ice-cooling. The reaction mixtures were warmed to room temperature, and then stirred for 6 hours. To the reaction mixtures were added a saturated aqueous sodium hydrogen carbonate solution and sodium sulfite, and the resulting mixtures were stirred at room temperature for 30 minutes. The resulting reaction mixtures were extracted with chloroform. The organic layers were washed successively with a saturated aqueous sodium hydrogen carbonate solution and saturated brine, and then the organic layers were dried over anhydrous sodium sulfate. The organic layers were concentrated under reduced pressure, and the resulting residues were subjected to a silica gel chromatography to give a present compound 14 2.28 g.

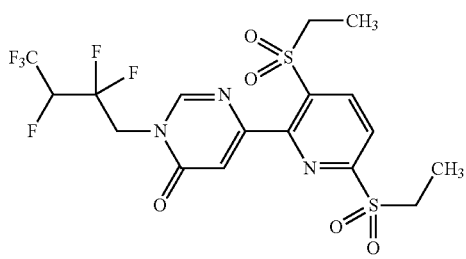 [SMILES: CCS(=O)(=O)c1ccc(S(=O)(=O)CC)c(-c2cc(=O)n(CC(F)(F)C(F)C(F)(F)F)cn2)n1]

Preparation Example 15

To a mixture of the present compound 14 300 mg and DMF 1 mL was added a 40% aqueous dimethylamine solution 260 µL under room temperature. The reaction mixtures were stirred under room temperature for 4.5 hours. To the reaction mixtures was added water, and the resulting mixtures were extracted with ethyl acetate. The organic layers were washed successively with water and saturated brine, and then the organic layers were dried over anhydrous sodium sulfate. The organic layers were concentrated under reduced pressure, and the resulting residues were subjected to a silica gel chromatography to give a present compound 15 240 mg.

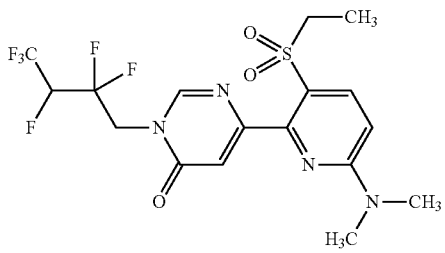

Preparation Example 16

To a mixture of the present compound 14 300 mg and DMF 1 mL was added pyrrolidine 70 µL under room temperature. The reaction mixtures were stirred under room temperature for 6 hours. To the reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give a present compound 16 260 mg.

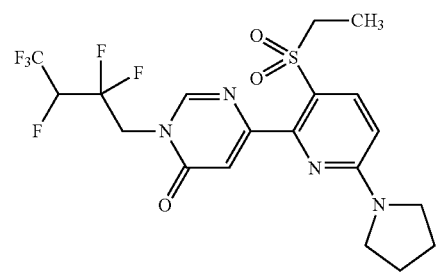 [SMILES: CCS(=O)(=O)c1ccc(N2CCCC2)nc1-c1cc(=O)n(CC(F)(F)C(F)C(F)(F)F)cn1]

Preparation Example 17

To a mixture of the present compound 14 300 mg and DMF 1 mL was added a 28% sodium methoxide solution in methanol 122 mg under ice-cooling. The reaction mixtures were stirred under room temperature for 6 hours. To the reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give a present compound 17 210 mg.

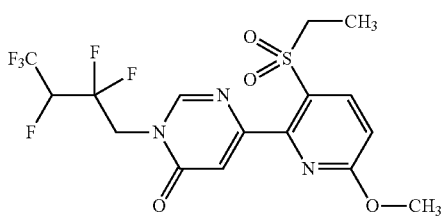 [SMILES: CCS(=O)(=O)c1ccc(OC)nc1-c1cc(=O)n(CC(F)(F)C(F)C(F)(F)F)cn1]

Preparation Example 18

To a mixture of the present compound 14 300 mg and DMF 1 mL were added successively 1H-1,2,4-triazole 44 mg and sodium hydride (60%, oily) 30 mg under ice-cooling. The reaction mixtures were stirred under room temperature for 6 hours. To the reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give a present compound 18 210 mg.

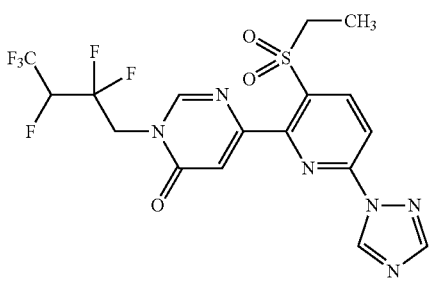 [SMILES: CCS(=O)(=O)c1ccc(-n2cncn2)nc1-c1cc(=O)n(CC(F)(F)C(F)C(F)(F)F)cn1]

Preparation Example 19(1)

A mixture of the intermediate compound (12-2) 5 g and N,N-dimethylformamide dimethyl acetal 30 ml was heated under reflux with stirring for 3 days. The resulting reaction mixtures were allowed to stand to room temperature and concentrated under reduced pressure, and the precipitated solids were collected by filtration. The resulting solids were washed with hexane, and then dried under reduced pressure to give an intermediate compound (19-1) 6.28 g.

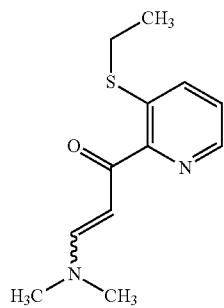 [SMILES: CCSc1cccnc1C(=O)C=CN(C)C]

$^1$H-NMR (CDCl$_3$) δ: 8.35 (1H, dd), 7.82 (1H, br s), 7.65 (1H, dd), 7.28-7.24 (1H, m), 6.16 (1H, br s), 3.14 (3H, br s), 2.95 (3H, br s), 2.89 (2H, q), 1.37 (3H, t).

Preparation Example 19(2)

A mixture of the intermediate compound (19-1) 2.36 g, urea 0.72 g, sodium ethoxide (20% solution in ethanol) 4.1 g, and ethanol 10 ml was heated under reflux with stirring for 2 hours. The resulting reaction mixtures were allowed to stand to room temperature and concentrated under reduced pressure, and to the mixtures were added water and concentrated hydrochloric acid, and the mixtures were extracted with chloroform, and then the organic layers were dried over anhydrous sodium sulfate. The organic layers were concentrated under reduced pressure, and then the resulting residues were subjected to a silica gel column chromatography to give a compound A 2.52 g.

Preparation Example 19(3)

To a mixture of the compound A 0.46 g, diisopropylethylamine 0.77 g, and chloroform 5 ml was added 2,2,3,4,4,4-hexafluorobutyl trifluoromethanesulfonate 0.96 g at room temperature, and the resulting mixtures were heated under reflux with stirring for 3 hours. To the reaction mixtures was added water, and the mixtures were extracted with ethyl acetate, and then the organic layers were dried over anhydrous sodium sulfate. The organic layers were concentrated under reduced pressure, and then the resulting residues were subjected to a silica gel column chromatography to give a present compound 19 0.22 g.

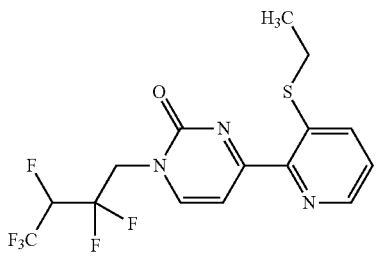 [SMILES: CCSc1cccnc1-c1ccn(CC(F)(F)C(F)C(F)(F)F)c(=O)n1]

Preparation Example 19(4)

To a mixture of the present compound 19 0.29 g and chloroform 10 ml was added mCPBA (75%) 0.37 g under ice-cooling, and the resulting mixtures were stirred at room temperature for 3 hours. To the resulting reaction mixtures was added a 10% aqueous sodium thiosulfate solution by pouring, and the mixtures were extracted with chloroform. The organic layers were washed with a saturated aqueous sodium hydrogen carbonate solution, dried over anhydrous sodium sulfate, and then concentrated under reduced pressure. The resulting residues were subjected to a silica gel column chromatography to give a present compound 20 0.08 g and a present compound 21 0.15 g.

Present compound 20

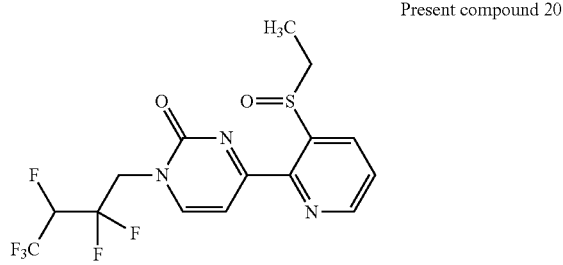

Present compound 21

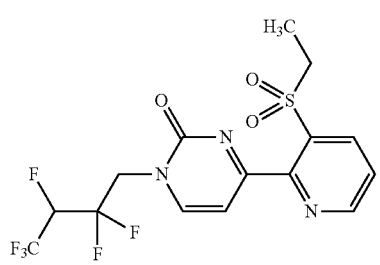

Preparation Example 20(1)

A present compound 22 was prepared by using 2,2,3,3-tetrafluoropropyl trifluoromethanesulfonate instead of 2,2,3,4,4,4-hexafluorobutyl trifluoromethanesulfonate according to the method described in the Preparation example 19(3).

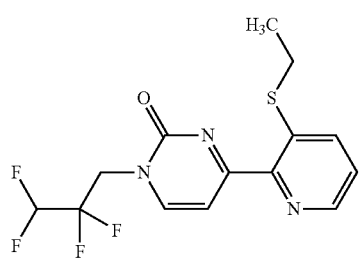 [SMILES: CCSc1cccnc1-c1ccn(CC(F)(F)C(F)F)c(=O)n1]

Preparation Example 20(2)

A present compound 23 and a present compound 24 were prepared by using the present compound 22 instead of the present compound 19 according to the method described in the Preparation example 19(4).

Present compound 23

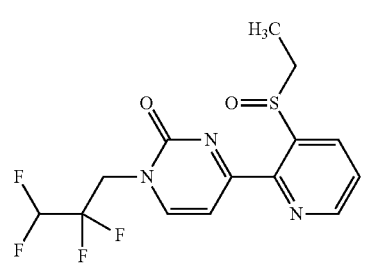

Present compound 24

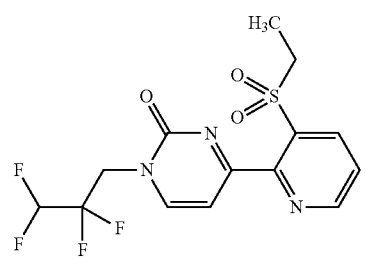

Preparation Example 21(1)

A present compound 25 was prepared by using 2,2,3,3,4,4,5,5-octafluoropentyl trifluoromethanesulfonate instead of 2,2,3,3-tetrafluoropropyl trifluoromethanesulfonate according to the method described in the Preparation example 19(3).

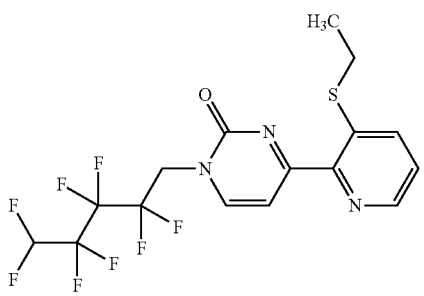 [SMILES: CCSc1cccnc1-c1ccn(CC(F)(F)C(F)(F)C(F)(F)C(F)F)c(=O)n1]

Preparation Example 21(2)

A present compound 26 and a present compound 27 were prepared by using the present compound 25 instead of the present compound 19 according to the method described in the Preparation example 19(4).

Present compound 26

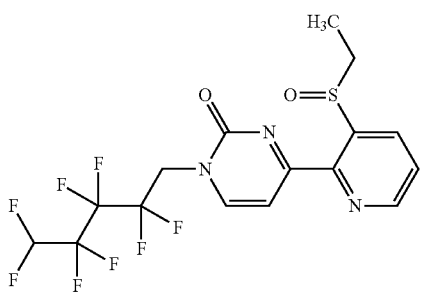

Present compound 27

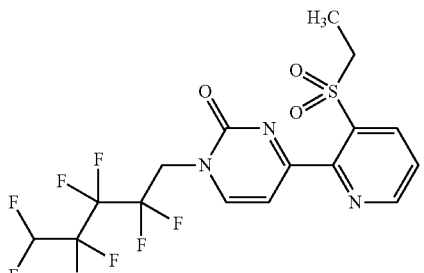

Preparation Example 22

To a mixture of the present compound 14 200 mg and DMF 1 mL were added successively 2,2,2-trifluoroethanol 40 µL and sodium hydride (60%, oily) 18 mg. The reaction mixtures were stirred under room temperature for 6 hours. To the reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give a present compound 28 160 mg.

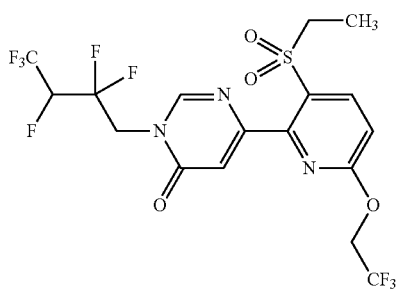 [SMILES: CCS(=O)(=O)c1ccc(OCC(F)(F)F)nc1-c1cc(=O)n(CC(F)(F)C(F)C(F)(F)F)cn1]

Preparation Example 23

To a mixture of the present compound 14 200 mg and DMF 1 mL were added successively diisopropylethylamine 0.20 mL and 5-aminomethyl-2-chlorothiazole hydrobromide 180 mg. The reaction mixtures were heated at 100° C. with stirring for 20 hours. The mixtures were allowed to stand to room temperature, and then to the reaction mixtures were additionally added diisopropylethylamine 0.20 mL and 5-aminomethyl-2-chlorothiazole hydrobromide 180 mg. The reaction mixtures were heated at 100° C. with stirring for 10 hours. The mixtures were allowed to stand to room temperature, and then to the reaction mixtures was added water, and the mixtures were extracted with ethyl acetate. The organic layers were washed successively with water and saturated brine, and the organic layers were dried over anhydrous sodium sulfate. The organic layers were concentrated under reduced pressure, and the resulting residues were subjected to a silica gel chromatography to give a present compound 29 76 mg.

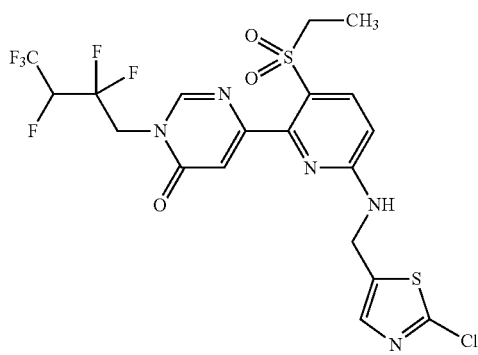 [SMILES: CCS(=O)(=O)c1ccc(NCc2cnc(Cl)s2)nc1-c1cc(=O)n(CC(F)(F)C(F)C(F)(F)F)cn1]

Preparation Example 24

A present compound 30 was prepared by using 1,1,2-trifluoro-4-bromo-1-butene instead of 1,1,3-trichloro-1-propene according to the method described in the Preparation example 12(7).

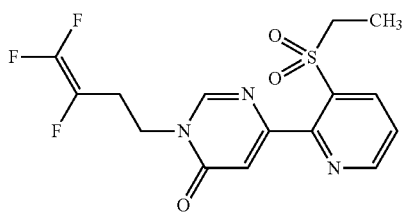 [SMILES: CCS(=O)(=O)c1cccnc1-c1cc(=O)n(CCC(F)=C(F)F)cn1]

Preparation Example 25

A present compound 31 was prepared by using 1,1,1,2,2-pentafluoro-4-iodobutane instead of 1,1,3-trichloro-1-propene according to the method described in the Preparation example 12(7).

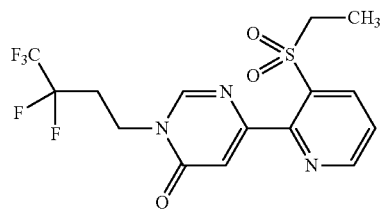 [SMILES: CCS(=O)(=O)c1cccnc1-c1cc(=O)n(CCC(F)(F)C(F)(F)F)cn1]

Preparation Example 26

A present compound 32 was prepared by using 1,1,1,2,2,3,3-heptafluoro-5-iodopentane instead of 1,1,3-trichloro-1-propene according to the method described in the Preparation example 12(7).

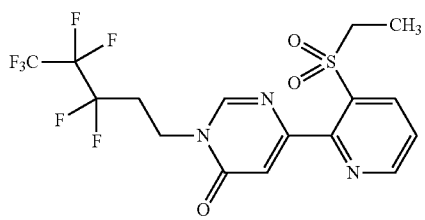 [SMILES: CCS(=O)(=O)c1cccnc1-c1cc(=O)n(CCC(F)(F)C(F)(F)C(F)(F)F)cn1]

Preparation Example 27

To a mixture of the present compound 9 1.0 g and toluene 6 mL was added 2,4-bis(4-methoxyphenyl)-1,3,2,4-dithiadiphosphetane-2,4-di sulfide 940 mg. The reaction mixtures were heated at 110° C. under reflux with stirring for 6 hours. The reaction mixtures were allowed to stand to room temperature, and then concentrated under reduced pressure. The resulting residues were subjected to a silica gel chromatography to give a present compound 33 1.1 g.

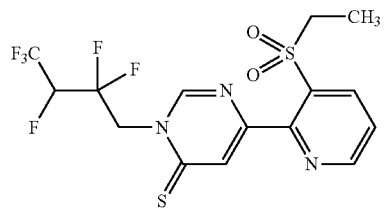 [SMILES: CCS(=O)(=O)c1cccnc1-c1cc(=S)n(CC(F)(F)C(F)C(F)(F)F)cn1]

Preparation Example 28

A present compound 34 was prepared by using a 28% aqueous ammonia solution instead of a 40% aqueous dimethylamine solution according to the method described in the Preparation example 15.

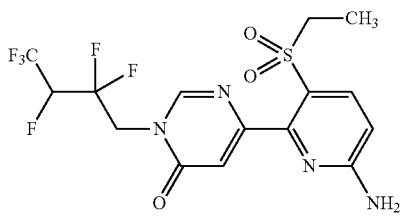

Preparation Example 29(1)

To a mixture of 3-chloro-5-(trifluoromethyl)pyridine-2-carboxylic acid 30 g and toluene 130 mL were added successively thionyl chloride 25 mL and DMF 1.6 mL under room temperature. The reaction mixtures were stirred at 110° C. for 5 hours. The reaction mixtures were allowed to stand to room temperature, and then concentrated under reduced pressure to give oily materials.

Preparation Example 29(2)

To a mixture of anhydrous magnesium chloride 22 g and THF 270 mL was added potassium methyl malonate 32 g under room temperature. The reaction mixtures were stirred at 50° C. for 1 hour. To the reaction mixtures were added successively the whole amount of the oily materials obtained in the above Preparation example 28(1) and triethylamine 65 mL under ice-cooling. The reaction mixtures were warmed to room temperature, and stirred at room temperature for 12 hours. To the resulting reaction mixtures was added 2N hydrochloric acid 400 mL under ice-cooling, and the resulting mixtures were stirred under room temperature for 2 hours. The resulting reaction mixtures were extracted with ethyl acetate. The organic layers were washed successively with a saturated aqueous sodium hydrogen carbonate solution and saturated brine, and the organic layers were dried over anhydrous sodium sulfate. The organic layers were concentrated under reduced pressure, and the resulting residues were subjected to a silica gel chromatography to give an intermediate compound (28-2) 29 g.

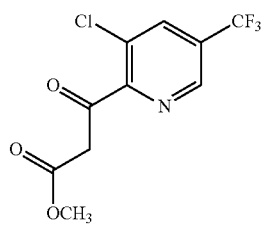 [SMILES: COC(=O)CC(=O)c1ncc(C(F)(F)F)cc1Cl]

$^1$H-NMR (CDCl$_3$) δ: 8.79 (1H, d), 8.08 (1H, d), 4.17 (2H, s), 3.73 (3H, s).

Preparation Example 29(3)

An intermediate compound (28-3) was prepared by using the intermediate compound (28-2) instead of the intermediate compound (12-3) according to the method described in the Preparation example 12(4).

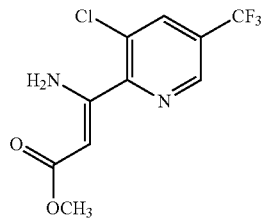 [SMILES: COC(=O)/C=C(\N)c1ncc(C(F)(F)F)cc1Cl]

$^1$H-NMR (CDCl$_3$) δ: 8.80 (1H, d), 8.06 (1H, d), 5.41 (1H, s), 3.74 (3H, s).

Preparation Example 29(4)

An intermediate compound (28-4) was prepared by using the intermediate compound (28-3) instead of the intermediate compound (6-3) according to the method described in the Preparation example 6(4).

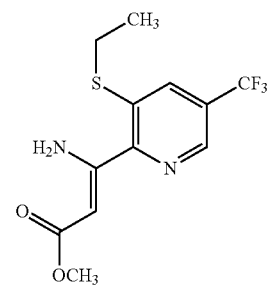 [SMILES: CCSc1cc(C(F)(F)F)cnc1/C(N)=C/C(=O)OC]

$^1$H-NMR (CDCl$_3$) δ: 8.60 (1H, d), 7.78 (1H, d), 5.23 (1H, s), 3.74 (3H, s), 2.99 (2H, q), 1.38 (3H, t).

Preparation Example 29(5)

To a mixture of the intermediate compound (28-4) 5.0 g and NMP 16 mL was added potassium tert-butoxide 9.0 g under ice-cooling. The reaction mixtures were stirred at 80° C. for 2 hours, and then allowed to stand to room temperature. To the reaction mixtures was added a saturated aqueous sodium hydrogen carbonate solution under ice-cooling, and the resulting mixtures were washed with ethyl acetate. The organic layers were dried over anhydrous sodium sulfate and concentrated under reduced pressure. The resulting residues were subjected to a silica gel chromatography to give a mixture 4.4 g comprising an intermediate compound (28-5).

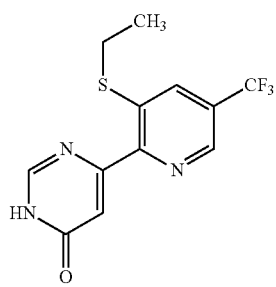 [SMILES: CCSc1cc(C(F)(F)F)cnc1-c1cc(=O)[nH]cn1]

$^1$H-NMR (CDCl$_3$) δ: 8.67 (1H, d), 8.30 (1H, d), 7.85 (1H, d), 7.06 (1H, d), 2.99 (2H, q), 1.37 (3H, t).

Preparation Example 29(6)

To a mixture of the mixture 4.4 g comprising the intermediate compound (28-5) and chloroform 28 mL were added successively diisopropylethylamine 2.9 mL and 2,2,3,4,4,4-hexafluorobutyl trifluoromethanesulfonate 3.5 g under room temperature. The reaction mixtures were stirred at 50° C. for 6 hours. The resulting reaction mixtures were allowed to stand to room temperature, and then to the mixtures was added a saturated aqueous sodium hydrogen carbonate solution, and the mixtures were extracted with chloroform. The organic layers were washed with saturated brine, and then the organic layers were dried over anhydrous sodium sulfate. The organic layers were concentrated under reduced pressure, and the resulting residues were subjected to a silica gel chromatography to give a present compound 35 1.4 g.

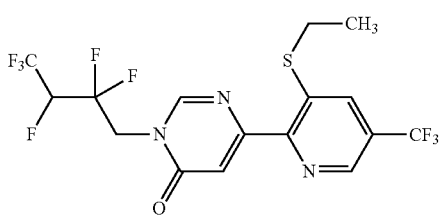 [SMILES: CCSc1cc(C(F)(F)F)cnc1-c1cc(=O)n(CC(F)(F)C(F)C(F)(F)F)cn1]

$^1$H-NMR (CDCl$_3$) δ: 8.67 (1H, br s), 8.25 (1H, br s), 7.85 (1H, br s), 7.14 (1H, br s), 5.20-4.98 (1H, m), 4.82-4.68 (1H, m), 4.63-4.48 (1H, m), 2.99 (2H, q), 1.38 (3H, t).

Preparation Example 29(7)

A present compound 36 was prepared by using the present compound 35 instead of the present compound 19 according to the method described in the Preparation example 19(4).

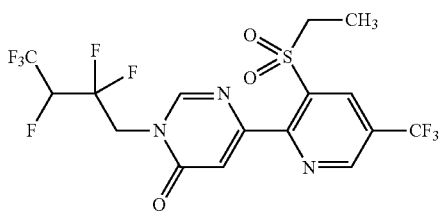 [SMILES: CCS(=O)(=O)c1cc(C(F)(F)F)cnc1-c1cc(=O)n(CC(F)(F)C(F)C(F)(F)F)cn1]

$^1$H-NMR (CDCl$_3$) δ: 9.14 (1H, d), 8.68 (1H, d), 8.17 (1H, d), 7.03 (1H, d), 5.17-4.96 (1H, m), 4.81-4.69 (1H, m), 4.60-4.49 (1H, m), 3.85 (2H, q), 1.41 (3H, t).

The compounds represented by formula (1-6)

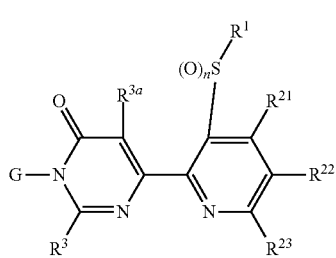

(1-6)

[wherein, $R^1$ represents an ethyl group; $R^{21}$ represents a hydrogen atom; and G, $R^{22}$, $R^{23}$, $R^3$, $R^{3a}$, and n represent any one combination indicated in the following Table 14 to Table 15] can be prepared according to the processes described above.

TABLE 14

| Present compound | G | n | $R^{22}$ | $R^{23}$ | $R^3$ | $R^{3a}$ |
|---|---|---|---|---|---|---|
| 37 | CF$_2$HCH$_2$ | 2 | H | H | H | H |
| 38 | CBrF$_2$CClFCH$_2$CH$_2$ | 2 | H | H | H | H |
| 39 | CBrH$_2$CH$_2$ | 2 | H | H | H | H |
| 40 | CFH$_2$CH$_2$CH$_2$ | 2 | H | H | H | H |
| 41 | CF$_3$CF$_2$CF$_2$CH$_2$CH$_2$ | 2 | H | H | H | H |
| 42 | CF$_2$HCF$_2$CF$_2$CF$_2$CH$_2$ | 2 | CF$_3$ | H | H | H |
| 43 | CF$_3$CFHCF$_2$CH$_2$ | 0 | CF$_3$ | H | H | H |
| 44 | CF$_3$CFHCF$_2$CH$_2$ | 1 | CF$_3$ | H | H | H |
| 45 | CF$_3$CFHCF$_2$CH$_2$ | 2 | CF$_3$ | H | H | H |
| 46 | CF$_3$CFHCF$_2$CH$_2$ | 2 | H |  | H | H |
| 47 | CF$_3$CFHCF$_2$CH$_2$ | 2 | H |  | H | H |

TABLE 15

| Present compound | G | n | $R^{22}$ | $R^{23}$ | $R^3$ | $R^{3a}$ |
|---|---|---|---|---|---|---|
| 48 | CF$_3$CFHCF$_2$CH$_2$ | 2 | H | 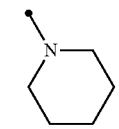 | H | H |
| 49 | CF$_3$CFHCF$_2$CH$_2$ | 2 | H | 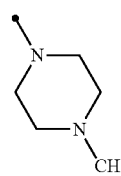 | H | H |
| 50 | CF$_3$CFHCF$_2$CH$_2$ | 2 | H | 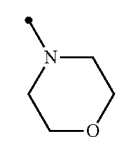 | H | H |
| 51 | CF$_3$CFHCF$_2$CH$_2$ | 2 | H | 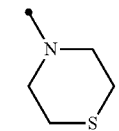 | H | H |
| 52 | CF$_3$CFHCF$_2$CH$_2$ | 2 | H | OCH$_2$C≡CH | H | H |
| 53 | CF$_3$CFHCF$_2$CH$_2$ | 2 | H | OCH$_2$CH$_3$ | H | H |
| 54 | CF$_3$CFHCF$_2$CH$_2$ | 2 | H | H | CH$_3$ | H |
| 55 | CF$_3$CFHCF$_2$CH$_2$ | 2 | H | H | H | CH$_3$ |
| 56 | CF$_3$CFHCF$_2$CH$_2$ | 2 | H | H | H | F |
| 57 | CF$_3$CFHCF$_2$CH$_2$ | 2 | H | H | H | Cl |

The physical properties of the compounds of the present invention are shown below.

TABLE 16

| Present compound | Physical property ($^1$H-NMR) |
| --- | --- |
| 1 | $^1$H-NMR (CDCl$_3$) δ: 8.38 (1H, s), 8.15 (1H, s), 7.99 (1H, d), 7.64 (1H, d), 6.65 (1H, s), 4.67 (2H, q), 3.65 (2H, q), 1.36 (3H, t). |
| 2 | $^1$H-NMR (CDCl$_3$) δ: 8.39 (1H, s), 8.14 (1H, s), 7.99 (1H, d), 7.65 (1H, d), 6.65 (1H, s), 4.69 (2H, t), 3.65 (2H, q), 1.37 (3H, t). |
| 3 | $^1$H-NMR (CDCl$_3$) δ: 8.39 (1H, s), 8.14 (1H, s), 7.99 (1H, d), 7.64 (1H, d), 6.65 (1H, s), 5.19-4.98 (1H, m), 4.77-4.50 (2H, m), 3.65 (2H, q), 1.37 (3H, t). |
| 4 | $^1$H-NMR (CDCl$_3$) δ: 8.40 (1H, s), 8.02 (1H, s), 7.99 (1H, d), 7.53 (1H, d), 5.16-4.90 (1H, m), 4.47-4.24 (1H, m), 3.54-3.28 (2H, m), 1.94 (3H, s), 1.31 (3H, t). |
| 5 | $^1$H-NMR (CDCl$_3$) δ: 8.40 (1H, s), 8.04 (1H, s), 7.99 (1H, d), 7.54 (1H, d), 5.21-4.74 (2H, m), 4.53-4.21 (1H, m), 3.54-3.30 (2H, m), 1.94 (3H, s), 1.30 (3H, t). |
| 6 | $^1$H-NMR (CDCl$_3$) δ: 8.89 (1H, dd), 8.45 (1H, dd), 8.14 (1H, s), 7.63 (1H, dd), 6.97 (1H, s), 4.66 (2H, q), 3.78 (2H, q), 1.37 (3H, t). |
| 7 | $^1$H-NMR (CDCl$_3$) δ: 8.89 (1H, dd), 8.45 (1H, dd), 8.15 (1H, s), 7.63 (1H, dd), 6.97 (1H, s), 4.69 (2H, t), 3.77 (2H, q), 1.37 (3H, t). |
| 8 | $^1$H-NMR (CDCl$_3$) δ: 8.89 (1H, dd), 8.45 (1H, dd), 8.15 (1H, s), 7.63 (1H, dd), 6.97 (1H, s), 6.12-5.81 (1H, m), 4.61 (2H, t), 3.78 (2H, q), 1.37 (3H, t). |
| 9 | $^1$H-NMR (CDCl$_3$) δ: 8.89 (1H, dd), 8.45 (1H, dd), 8.15 (1H, d), 7.63 (1H, dd), 6.97 (1H, d), 5.14-4.97 (1H, m), 4.81-4.70 (1H, m), 4.59-4.45 (1H, m), 3.78 (2H, q), 1.37 (3H, t). |
| 10 | $^1$H-NMR (CDCl$_3$) δ: 8.89 (1H, dd), 8.45 (1H, dd), 8.14 (1H, d), 7.63 (1H, dd), 6.98 (1H, d), 6.25-5.93 (1H, m), 4.73 (2H, t), 3.78 (2H, q), 1.38 (3H, t). |

TABLE 17

| Present compound | Physical property ($^1$H-NMR) |
| --- | --- |
| 11 | $^1$H-NMR (CDCl$_3$) δ: 8.88 (1H, dd), 8.45 (1H, dd), 8.11 (1H, s), 7.61 (1H, dd), 6.90 (1H, s), 4.05 (2H, t), 3.78 (2H, q), 2.29-2.16 (2H, m), 2.16-2.07 (2H, m), 1.37 (3H, t). |
| 12 | $^1$H-NMR (CDCl$_3$) δ: 8.88 (1H, dd), 8.44 (1H, dd), 8.15 (1H, d), 7.61 (1H, dd), 6.92 (1H, d), 6.25 (1H, t), 4.67 (2H, d), 3.79 (2H, q), 1.37 (3H, t). |
| 13 | $^1$H-NMR (CDCl$_3$) δ: 8.22 (1H, s), 7.53 (1H, d), 7.21-7.15 (2H, m), 5.20-4.97 (1H, m), 4.82-4.66 (1H, m), 4.60-4.46 (1H, m), 3.19 (2H, q), 2.89 (2H, q), 1.39 (3H, t), 1.31 (3H, t). |
| 14 | $^1$H-NMR (CDCl$_3$) δ: 8.73 (1H, d), 8.37 (1H, d), 8.17 (1H, d), 6.99 (1H, d), 5.17-4.96 (1H, m), 4.82-4.68 (1H, m), 4.61-4.48 (1H, m), 3.87 (2H, q), 3.53 (2H, q), 1.46-1.36 (6H, m). |
| 15 | $^1$H-NMR (CDCl$_3$) δ: 8.12 (1H, s), 8.03 (1H, d), 6.91 (1H, d), 6.59 (1H, d), 5.19-4.96 (1H, m), 4.78-4.61 (1H, m), 4.58-4.43 (1H, m), 3.67 (2H, q), 3.20 (6H, s), 1.33 (3H, t). |
| 16 | $^1$H-NMR (CDCl$_3$) δ: 8.10 (1H, d), 8.01 (1H, d), 6.91 (1H, d), 6.43 (1H, d), 5.17-4.96 (1H, m), 4.78-4.61 (1H, m), 4.55-4.41 (1H, m), 3.66 (2H, q), 3.60 (4H, br s), 2.05 (4H, br s), 1.33 (3H, t). |
| 17 | $^1$H-NMR (CDCl$_3$) δ: 8.25 (1H, d), 8.14 (1H, d), 6.97 (1H, d), 6.95 (1H, d), 5.19-4.96 (1H, m), 4.79-4.67 (1H, m), 4.60-4.45 (1H, m), 4.05 (3H, s), 3.75 (2H, q), 1.36 (3H, t). |
| 18 | $^1$H-NMR (CDCl$_3$) δ: 9.24 (1H, s), 8.63 (1H, d), 8.24-8.14 (3H, m), 7.00 (1H, d), 5.21-4.99 (1H, m), 4.83-4.68 (1H, m), 4.64-4.51 (1H, m), 3.82 (2H, q), 1.40 (3H, t). |
| 19 | $^1$H-NMR (CDCl$_3$) δ: 8.45 (1H, dd), 7.75 (1H, dd), 7.71 (1H, d), 7.39 (1H, d), 7.35 (1H, dd), 5.31-5.09 (1H, m), 4.79-4.40 (2H, m), 2.94 (2H, q), 1.39 (3H, t). |
| 20 | $^1$H-NMR (CDCl$_3$) δ: 8.80 (1H, dd), 8.73-8.69 (1H, m), 7.81 (1H, d), 7.72 (1H, dd), 7.57 (1H, dd), 5.25-5.02 (1H, m), 4.83-4.41 (2H, m), 3.63-3.50 (1H, m), 3.04-2.91 (1H, m), 1.47 (3H, t). |

TABLE 18

| Present compound | Physical property ($^1$H-NMR) |
| --- | --- |
| 21 | $^1$H-NMR (CDCl$_3$) δ: 8.89 (1H, dd), 8.48 (1H, dd), 7.82 (1H, d), 7.65 (1H, dd), 6.86 (1H, d), 5.20-5.03 (1H, m), 4.78-4.47 (2H, m), 3.92 (2H, q), 1.38 (3H, t). |
| 22 | $^1$H-NMR (CDCl$_3$) δ: 8.44 (1H, d), 7.75 (1H, d), 7.71 (1H, d), 7.37-7.33 (2H, m), 6.21-5.88 (1H, m), 4.57 (2H, t), 2.94 (2H, q), 1.39 (3H, t). |
| 23 | $^1$H-NMR (CDCl$_3$) δ: 8.80 (1H, d), 8.71 (1H, d), 7.81 (1H, dd), 7.72 (1H, dd), 7.55 (1H, d), 6.19-5.86 (1H, m), 4.74-4.45 (2H, m), 3.63-3.51 (1H, m), 3.04-2.90 (1H, m), 1.47 (3H, t). |
| 24 | $^1$H-NMR (CDCl$_3$) δ: 8.89 (1H, dd), 8.48 (1H, dd), 7.82 (1H, d), 7.65 (1H, dd), 6.84 (1H, d), 6.13-5.86 (1H, m), 4.59 (2H, t), 3.92 (2H, q), 1.38 (3H, t). |
| 25 | $^1$H-NMR (CDCl$_3$) δ: 8.44 (1H, dd), 7.75 (1H, dd), 7.70 (1H, d), 7.37-7.32 (2H, m), 6.27-5.95 (1H, m), 4.72 (2H, t), 2.94 (2H, q), 1.38 (3H, t). |
| 26 | $^1$H-NMR (CDCl$_3$) δ: 8.80 (1H, d), 8.71 (1H, d), 7.79 (1H, d), 7.72 (1H, dd), 7.56 (1H, d), 6.26-5.93 (1H, m), 4.87-4.57 (2H, m), 3.64-3.51 (1H, m), 3.02-2.90 (1H, m), 1.48 (3H, t). |
| 27 | $^1$H-NMR (CDCl$_3$) δ: 8.89 (1H, dd), 8.48 (1H, dd), 7.80 (1H, d), 7.65 (1H, dd), 6.84 (1H, d), 6.26-5.94 (1H, m), 4.73 (2H, t), 3.92 (2H, q), 1.38 (3H, t). |
| 28 | $^1$H-NMR (CDCl$_3$) δ: 8.36 (1H, d), 8.14 (1H, d), 7.12 (1H, d), 6.91 (1H, d), 5.19-4.96 (1H, m), 4.86 (2H, q), 4.80-4.66 (1H, m), 4.61-4.47 (1H, m), 3.75 (2H, q), 1.37 (3H, t). |
| 29 | $^1$H-NMR (CDCl$_3$) δ: 8.14 (1H, d), 8.07 (1H, d), 7.46 (1H, s), 6.93 (1H, d), 6.57 (1H, d), 5.46-5.40 (1H, m), 5.19-4.96 (1H, m), 4.80 (2H, d), 4.76-4.48 (2H, m), 3.69 (2H, q), 1.35 (3H, t). |
| 30 | $^1$H-NMR (CDCl$_3$) δ: 8.88 (1H, dd), 8.44 (1H, dd), 8.05 (1H, s), 7.60 (1H, dd), 6.91 (1H, s), 4.17 (2H, t), 3.77 (2H, q), 2.93-2.81 (2H, m), 1.37 (3H, t). |

TABLE 19

| Present compound | Physical property ($^1$H-NMR) |
| --- | --- |
| 31 | $^1$H-NMR (CDCl$_3$) δ: 8.88 (1H, dd), 8.44 (1H, dd), 8.14 (1H, s), 7.61 (1H, dd), 6.92 (1H, s), 4.26 (2H, t), 3.78 (2H, q), 2.75-2.59 (2H, m), 1.37 (3H, t). |
| 32 | $^1$H-NMR (CDCl$_3$) δ: 8.88 (1H, dd), 8.45 (1H, dd), 8.14 (1H, s), 7.61 (1H, dd), 6.93 (1H, d), 4.27 (2H, t), 3.78 (2H, q), 2.79-2.62 (2H, m), 1.37 (3H, t). |
| 33 | $^1$H-NMR (CDCl$_3$) δ: 8.90 (1H, dd), 8.46 (1H, dd), 8.30 (1H, d), 7.89 (1H, d), 7.63 (1H, dd), 5.51-5.36 (1H, m), 5.31-5.06 (2H, m), 3.79 (2H, q), 1.39 (3H, t). |
| 34 | $^1$H-NMR (CDCl$_3$) δ: 8.12 (1H, s), 8.07 (1H, d), 6.84 (1H, s), 6.63 (1H, d), 5.15-4.93 (3H, m), 4.81-4.65 (1H, m), 4.54-4.42 (1H, m), 3.63 (2H, q), 1.34 (3H, t). |
| 35 | $^1$H-NMR (CDCl$_3$) δ: 8.67 (1H, br s), 8.25 (1H, br s), 7.85 (1H, br s), 7.14 (1H, br s), 5.20-4.98 (1H, m), 4.82-4.68 (1H, m), 4.63-4.48 (1H, m), 2.99 (2H, q), 1.38 (3H, t). |
| 36 | $^1$H-NMR (CDCl$_3$) δ: 9.14 (1H, d), 8.68 (1H, d), 8.17 (1H, d), 7.03 (1H, d), 5.17-4.96 (1H, m), 4.81-4.69 (1H, m), 4.60-4.49 (1H, m), 3.85 (2H, q), 1.41 (3H, t). |
| 37 | $^1$H-NMR (CDCl$_3$) δ: 8.88 (1H, dd), 8.45 (1H, dd), 8.10 (1H, s), 7.62 (1H, dd), 6.94 (1H, s), 6.15 (1H, tt), 4.30 (2H, td), 3.78 (2H, q), 1.37 (3H, t). |

TABLE 19-continued

| Present compound | Physical property ($^1$H-NMR) |
|---|---|
| 38 | $^1$H-NMR (CDCl$_3$) δ: 8.88 (1H, dd), 8.44 (1H, dd), 8.18 (1H, s), 7.61 (1H, dd), 6.92 (1H, s), 4.46-4.39 (1H, m), 4.31-4.24 (1H, m), 3.83-3.72 (2H, m), 3.02-2.91 (1H, m), 2.83-2.66 (1H, m), 1.37 (3H, t). |
| 39 | $^1$H-NMR (CDCl$_3$) δ: 8.89 (1H, dd), 8.45 (1H, dd), 8.18 (1H, s), 7.61 (1H, dd), 6.93 (1H, s), 4.36 (2H, t), 3.85-3.73 (4H, m), 1.37 (3H, t). |
| 40 | $^1$H-NMR (CDCl$_3$) δ: 8.88 (1H, dd), 8.44 (1H, dd), 8.13 (1H, s), 7.60 (1H, dd), 6.89 (1H, s), 4.63-4.43 (2H, m), 4.14 (2H, t), 3.79 (2H, q), 2.31-2.16 (2H, m), 1.37 (3H, t). |

TABLE 20

| Present compound | Physical property ($^1$H-NMR) |
|---|---|
| 41 | $^1$H-NMR (CDCl$_3$) δ: 8.88 (1H, dd), 8.45 (1H, dd), 8.14 (1H, s), 7.61 (1H, dd), 6.93 (1H, s), 4.27 (2H, t), 3.78 (2H, q), 2.78-2.63 (2H, m), 1.37 (3H, t). |
| 42 | $^1$H-NMR (CDCl$_3$) δ: 9.13 (1H, d), 8.68 (1H, d), 8.17 (1H, d), 7.03 (1H, d), 6.10 (1H, tt), 4.74 (2H, t), 3.85 (2H, q), 1.41 (3H, t). |
| 43 | $^1$H-NMR (CDCl$_3$) δ: 8.67 (1H, d), 8.25 (1H, d), 7.85 (1H, d), 7.14 (1H, d), 5.20-4.98 (1H, m), 4.80-4.50 (2H, m), 2.99 (2H, q), 1.38 (3H, t). |
| 45 | $^1$H-NMR (CDCl$_3$) δ: 9.14 (1H, dd), 8.68 (1H, dd), 8.17 (1H, d), 7.03 (1H, d), 5.18-4.97 (1H, m), 4.82-4.48 (2H, m), 3.85 (2H, q), 1.41 (3H, t). |
| 46 | $^1$H-NMR (CDCl$_3$) δ: 8.62 (1H, dd), 8.52 (1H, d), 8.22 (1H, d), 8.17 (1H, d), 7.83 (1H, dd), 7.02 (1H, d), 6.54 (1H, dd), 5.21-4.96 (1H, m), 4.81-4.50 (2H, m), 3.81 (2H, q), 1.40 (3H, t). |
| 47 | $^1$H-NMR (CDCl$_3$) δ: 8.55 (1H, d), 8.46 (1H, d), 8.18 (1H, d), 7.75-7.73 (1H, m), 7.60 (1H, d), 7.26-7.25 (1H, m), 7.02 (1H, d), 5.22-5.00 (1H, m), 4.81-4.51 (2H, m), 3.82 (2H, q), 1.40 (3H, t). |
| 48 | $^1$H-NMR (CDCl$_3$) δ: 8.11 (1H, d), 8.00 (1H, d), 6.90 (1H, d), 6.68 (1H, d), 5.17-4.95 (1H, m), 4.78-4.43 (2H, m), 3.76-3.63 (6H, m), 1.75-1.69 (2H, m), 1.69-1.60 (4H, m), 1.34 (3H, t). |
| 49 | $^1$H-NMR (CDCl$_3$) δ: 8.11 (1H, s), 8.05 (1H, d), 6.90 (1H, s), 6.70 (1H, d), 5.15-4.98 (1H, m), 4.78-4.44 (2H, m), 3.79-3.72 (4H, m), 3.68 (2H, q), 2.55-2.47 (4H, m), 2.36 (3H, s), 1.34 (3H, t). |
| 50 | $^1$H-NMR (CDCl$_3$) δ: 8.11 (1H, s), 8.09 (1H, d), 6.89 (1H, s), 6.70 (1H, d), 5.16-4.96 (1H, m), 4.79-4.43 (2H, m), 3.85-3.78 (4H, m), 3.75-3.64 (6H, m), 1.34 (3H, t). |

TABLE 21

| Present compound | Physical property ($^1$H-NMR) |
|---|---|
| 51 | $^1$H-NMR (CDCl$_3$) δ: 8.11 (1H, s), 8.07 (1H, d), 6.87 (1H, s), 6.69 (1H, d), 5.19-4.94 (1H, m), 4.77-4.45 (2H, m), 4.15-4.06 (4H, m), 3.69 (2H, q), 2.75-2.65 (4H, m), 1.35 (3H, t). |
| 52 | $^1$H-NMR (CDCl$_3$) δ: 8.30 (1H, d), 8.14 (1H, s), 7.02 (1H, d), 7.00 (1H, s), 5.16-4.97 (3H, m), 4.80-4.45 (2H, m), 3.77 (2H, q), 2.53 (1H, t), 1.37 (3H, t). |
| 53 | $^1$H-NMR (CDCl$_3$) δ: 8.23 (1H, d), 8.13 (1H, s), 6.95 (1H, s), 6.92 (1H, d), 5.15-4.98 (1H, m), 4.78-4.46 (4H, m), 3.74 (2H, q), 1.43 (3H, t), 1.36 (3H, t). |
| 54 | $^1$H-NMR (CDCl$_3$) δ: 8.89 (1H, dd), 8.44 (1H, dd), 7.62 (1H, dd), 6.83 (1H, s), 5.26-5.08 (1H, m), 4.98-4.52 (2H, m), 3.78 (2H, q), 2.64 (3H, s), 1.39 (3H, t). |
| 55 | $^1$H-NMR (CDCl$_3$) δ: 8.93 (1H, dd), 8.44 (1H, dd), 8.04 (1H, s), 7.63 (1H, dd), 5.17-4.95 (1H, m), 4.83-4.44 (2H, m), 3.47 (2H, q), 1.96 (3H, s), 1.31 (3H, t). |

TABLE 21-continued

| Present compound | Physical property ($^1$H-NMR) |
|---|---|
| 56 | $^1$H-NMR (CDCl$_3$) δ: 8.81 (1H, dd), 8.47 (1H, dd), 7.76 (1H, dd), 7.40 (1H, t), 5.13-4.90 (1H, m), 4.24-3.86 (2H, m), 3.57 (2H, q), 1.36 (3H, t). |
| 57 | $^1$H-NMR (CDCl$_3$) δ: 8.97 (1H, dd), 8.43 (1H, dd), 8.11 (1H, s), 7.68 (1H, dd), 5.15-4.98 (1H, m), 4.87-4.51 (2H, m), 3.40 (2H, q), 1.31 (3H, t). |

Next, the formulation examples of the Present compound are shown below. The "parts" represents "part by weight" unless otherwise specified.

Formulation Example 1

Into a mixture of 35 parts of xylene and 35 parts of N,N-dimethylformamide, 10 parts of any one of the Present compounds 1 to 57 is dissolved, and then 14 parts of polyoxyethylene styryl phenyl ether and 6 parts of calcium dodecylbenzene sulfonate are added thereto, followed by mixing them to obtain each formulation.

Formulation Example 2

Four (4) parts of sodium lauryl sulfate, 2 parts of calcium lignin sulfonate, 20 parts of synthetic hydrated silicon oxide fine powder, and 54 parts of diatomaceous earth are mixed, and further 20 parts of any one of the Present compounds 1 to 57 is added thereto, followed by mixing them to obtain each wettable powders.

Formulation Example 3

To 2 parts of any one of the Present compounds 1 to 57, 1 part of synthetic hydrated silicon oxide fine powder, 2 parts of calcium lignin sulfonate, 30 parts of bentonite, and 65 parts of kaolin clay are added, followed by mixing them to obtain a mixture. To the mixture is then added an appropriate amount of water, and the resulting mixture is additionally stirred, and subjected to granulation with a granulator and forced-air drying to obtain each granular formulation.

Formulation Example 4

Into an appropriate amount of acetone, 1 part of any one of the Present compounds 1 to 57 is dissolved, and then 5 parts of synthetic hydrated silicon oxide fine powder, 0.3 parts of isopropyl acid phosphate, and 93.7 parts of Fubasami clay are added thereto, followed by mixing with stirring thoroughly and removal of acetone from the mixture by evaporation to obtain each powder formulation.

Formulation Example 5

Thirty five (35) parts of a mixture of polyoxyethylene alkyl ether sulfate ammonium salt and white carbon (weight ratio of 1:1), 10 parts of any one of the Present compounds 1 to 57, and 55 parts of water are mixed, followed by finely grounding by a wet grinding method to obtain each flowable formulation.

Formulation Example 6

Into a mixture of 5 parts of xylene and 5 parts of trichloroethane, 0.1 part of any one of the Present compounds 1 to 57 is dissolved, and the resulting mixture is then mixed with 89.9 parts of deodorized kerosene to obtain each oil solution.

Formulation example 7

Into 0.5 mL of acetone, 10 mg of any one of the Present compounds 1 to 57 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the Present compounds 1 to 57 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain each oily aerosol.

Formulation Example 9

A mixture of 0.6 parts of any one of the Present compounds 1 to 57, 0.01 part of BHT (2,6-di-tert-butyl-4-methylphenol), 5 parts of xylene, 3.39 parts of deodorized kerosine, and 1 part of an emulsifier {Rheodol MO-60 (manufactured by Kao Corporation)}, and 50 parts of distilled water are filled into an aerosol container, and a valve part is attached. Then, 40 parts of a propellant (LPG) is filled therein through the valve under pressure to obtain each aqueous aerosol.

Formulation Example 10

Zero point one (0.1) g of any one of the Present compounds 1 to 57 are mixed into 2 mL of propylene glycol, and the resulting solution is impregnated into a porous ceramic plate having a size of 4.0 cm×4.0 cm and a thickness of 1.2 cm, to obtain each thermal fumigant.

Formulation Example 11

Five (5) parts of any one of the Present compounds 1 to 57, and 95 parts of ethylene-methyl methacrylate copolymer (the ratio of the methyl methacrylate in the copolymer: 10% by weight, Acryft (registered trademark) WD 301, manufactured by Sumitomo Chemical Co. Ltd.) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 12

Five (5) parts of any one of the Present compounds 1 to 57, and 95 parts of plasticized polyvinyl chloride resin are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 13

One hundred (100) mg of any one of the Present compounds 1 to 57, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixture is compressed to an appropriate size to obtain each tablet.

Formulation Example 14

Twenty five (25) mg of any one of the Present compounds 1 to 57, 60 mg of lactose, 25 mg of corn starch, 6 mg of carmellose calcium, and an appropriate amount of 5% of hydroxypropyl methylcellulose are mixed, and the resulting mixture are filled into a hard shell gelatin capsule or a hydroxypropyl methylcellulose capsule to obtain each capsule.

Formulation Example 15

To 100 mg of any one of the Present compounds 1 to 57, 500 mg of fumaric acid, 2,000 mg of sodium chloride, 150 mg of methylparaben, 50 mg of propylparaben, 25,000 mg of granulated sugar, 13,000 mg of sorbitol (70% solution), 100 mg of Veegum K (manufactured by Vanderbilt Co.), 35 mg of perfume, and 500 mg of coloring agent, a distilled water is added so that a final volume is set to be 100 mL, followed by mixing them to obtain each suspension for oral administration.

Formulation Example 16

Into a mixture of 5% by weight of polysorbate 85, 3% by weight of benzyl alcohol, and 30% by weight of propylene glycol, 5% by weight of any one of the Present compounds 1 to 57 is dissolved, and phosphate buffer is added thereto so that a pH of the solution is set to be 6.0 to 6.5, and then water is added as the rest parts to obtain each solution for oral administration.

Formulation Example 17

To a mixture of 57% by weight of fractional distilled palm oil and 3% by weight of polysorbate 85, 5% by weight of aluminum distearate is added, and heated to disperse it. The resulting mixture is cooled to room temperature, and 25% by weight of saccharin is dispersed in the oil vehicle. Ten (10) % by weight of any one of the Present compounds 1 to 57 is divided thereto to obtain each paste for oral administration.

Formulation Example 18

Five (5)% by weight of any one of the Present compounds 1 to 57 is mixed with 95% by weight of limestone filler, followed by a wet granulation of the resulting mixture to obtain each granule for oral administration.

Formulation Example 19

Into 80 parts of diethylene glycol monoethyl ether, 5 parts of any one of the Present compounds 1 to 57 is dissolved, and 15 parts of propylene carbonate is added thereto, and the resulting mixture is mixed to obtain each spot-on solution.

Formulation Example 20

Into 70 parts of diethylene glycol monoethyl ether, 10 parts of any one of the Present compounds 1 to 57 is dissolved, and 20 parts of 2-octyldodecanol is added thereto, and the resulting mixture is mixed to obtain each pour-on solution.

Formulation Example 21

To 0.5 parts of any one of the Present compounds 1 to 57, 60 parts of Nikkol (registered trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly to obtain a homogeneous solution, and 19.5 parts of water is then added thereto and the resulting mixture is further mixed with stirring thoroughly to obtain each homogeneous solution of shampoo formulation.

Formulation Example 22

Zero point fifteen (0.15)% by weight of any one of the Present compounds 1 to 57, 95% by weight of animal feed, as well as 4.85% by weight of a mixture of dibasic calcium phosphate, diatomaceous earth, Aerosil, and carbonate (or chalk) are mixed with stirring thoroughly to obtain each premix for animal feed.

Formulation Example 23

Seven point two (7.2) g of any one of the Present compounds 1 to 57, and 92.8 g of Hosco (registered trademark) S-55 (manufactured by Maruishi Pharmaceuticals) are melted and mixed at 100° C., and the resulting mixture is poured into a suppository mold, followed by performing a cooling solidification to obtain each suppository.

Next, Test examples are used to show an efficacy of the Present compounds on controlling harmful arthropods.

Test Example 1

Each formulation comprising the present compound 1, 2, 3, 9, 15, 16, 17, 18, 21, 26, 27, or 33 prepared by the process according to the Formulation example 5 was diluted with water until each concentration of the active ingredient reached 500 ppm to prepare each test chemical solution.

Meanwhile, cucumber seedling (on the developmental stage of the first true leaf) was planted in a plastic cup, and approximately 30 heads of cotton aphid (*Aphis gossypii*) (all stages of life) were released onto the leaves of the cucumber, and the seedling was left to stand for one day. Into the seedling was sprayed 20 mL of each of the above test chemical solution.

After 6 days from the spraying, the number of the surviving cotton aphid lived on the leaves of the cucumber was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 1, 2, 3, 9, 15, 16, 17, 18, 21, 26, 27, or 33 showed 90% or greater as the controlling value.

Test Example 2

Each formulation comprising the present compound 1, 2, 3, 6, 7, 8, 9, 10, 11, 12, 14, 29, 31, 32, 33, 34, 36, 37, 38, 40, 42, 45, 46, 47, 53, 54, or 57 prepared by the process according to the Formulation example 5 was diluted with water until each concentration of the active ingredient reached 200 ppm to prepare each test chemical solution.

Meanwhile, cucumber seedling (on the developmental stage of the first true leaf) was planted in a plastic cup, and approximately 30 heads of cotton aphid (*Aphis gossypii*) (all stages of life) were released onto the leaves of the cucumber, and the seedling was left to stand for one day. Into the seedling was sprayed 20 mL of each of the above test chemical solution.

After 6 days from the spraying, the number of the surviving cotton aphid lived on the leaves of the cucumber was investigated, and the controlling value was calculated by the following equation.

Controlling value (%)={1−(Cb×Tai)/(Cai×Tb)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 1, 2, 3, 6, 7, 8, 9, 10, 11, 12, 14, 29, 31, 32, 33, 34, 36, 37, 38, 40, 42, 45, 46, 47, 53, 54, or 57 showed 90% or greater as the controlling value.

Test Example 3

Each formulation comprising the present compound 3, 4, 6, 7, 8, 9, 10, 31, 32, 33, 34, 36, 37, 38, 40, or 45 prepared by the process according to the Formulation example 5 was diluted with water until each concentration of the active ingredient reached 200 ppm to prepare each test chemical solution.

Meanwhile, cucumber seedling (on the developmental stage of the second true leaf) was planted in a plastic cup, and 5 mL of each of the above test chemical solution was applied to the seedling by irrigation at plant foot, and the seedling was left to stand at 25° C. in a greenhouse for 7 days. Approximately 30 heads of cotton aphid (*Aphis gossypii*) (all stages of life) were released onto the leaves of the cucumber, and the seedling was left to stand for additional 6 days in the greenhouse, and then the number of the surviving cotton aphid lived on the leaves of the cucumber was investigated, and the controlling value was calculated by the following equation.

Controlling value (%)={1−($Cb \times Tai$)/($Cai \times Tb$)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 3, 4, 6, 7, 8, 9, 10, 31, 32, 33, 34, 36, 37, 38, 40, or 45 showed 90% or greater as the controlling value.

Test Example 4

Each formulation comprising the present compound 9 or 15 prepared by the process according to the Formulation example 5 was diluted with water until each concentration of the active ingredient reached 500 ppm to prepare each test chemical solution.

Rice seedling (on the developmental stage of the second true leaf) was planted in a polyethylene cup, and 10 mL of each of the above test chemical solution was sprayed into the seedling. After air-drying the seedling, 20 heads of 3rd to 4th instar larvae of brown planthopper (*Nilaparvata lugens*) were released onto the rice leaves, and the seedling was left to stand at 25° C. in a greenhouse. After 6 days, the number of the surviving brown planthopper lived on the rice leaves was investigated, and the controlling value was calculated by the following equation.

Controlling value (%)={1−($Cb \times Tai$)/($Cai \times Tb$)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 9 or 15 showed 90% or greater as the controlling value.

Test Example 5

Each formulation comprising the present compound 7, 8, 9, 10, 11, 12, 29, 31, 32, 33, 34, 37, 38, 40, or 47 prepared by the process according to the Formulation example 5 was diluted with water until each concentration of the active ingredient reached 200 ppm to prepare each test chemical solution.

Rice seedling (on the developmental stage of the second true leaf) was planted in a polyethylene cup, and 10 mL of each of the above test chemical solution was sprayed into the seedling. After air-drying the seedling, 20 heads of 3rd to 4th instar larvae of brown planthopper (*Nilaparvata lugens*) were released onto the rice leaves, and the seedling was left to stand at 25° C. in a greenhouse. After 6 days, the number of the surviving brown planthopper lived on the rice leaves was investigated, and the controlling value was calculated by the following equation.

Controlling value (%)={1−($Cb \times Tai$)/($Cai \times Tb$)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 7, 8, 9, 10, 11, 12, 29, 31, 32, 33, 34, 37, 38, 40, or 47 showed 90% or greater as the controlling value.

Test Example 6

Each formulation comprising the present compound 1, 2, 4, 7, 8, 9, 10, 11, 31, 32, 34, 36, 38, or 45 prepared by the process according to the Formulation example 5 was diluted with water until each concentration of the active ingredient reached 200 ppm to prepare each test chemical solution.

Meanwhile, rice seedling (after 2 weeks from seeding, on the developmental stage of the second true leaf) was planted in a plastic cup, and 5 mL of each of the above test chemical solution was applied to the seedling by irrigation at plant foot, and the seedling was left to stand at 25° C. in a greenhouse for 7 days. Twenty (20) heads of 3rd to 4th instar larvae of brown planthopper (*Nilaparvata lugens*) were released onto the rice leaves, and the seedling was left to stand for additional 6 days in the greenhouse, and then the number of the surviving brown planthopper lived on the rice leaves was investigated, and the controlling value was calculated by the following equation.

Controlling value (%)={1−($Cb \times Tai$)/($Cai \times Tb$)}×100 wherein the symbols in the equation represent the following descriptions.

Cb: Number of the test insects before treatment in untreated group

Cai: Number of the surviving insects lived on the leaves at the time of the investigation in untreated group Tb: Number of the test insects before treatment in treated group Tai: Number of the surviving insects lived on the leaves at the time of the investigation in treated group Here the "untreated group" represents a group where a test chemical solution which was prepared by diluting a formulation prepared according to the Formulation example 5 except for not comprising the present compound with the same amount of water as that used in the case of the treated group was sprayed.

As a result, the treated group that was treated with each test chemical solution comprising the present compound 1, 2, 4, 7, 8, 9, 10, 11, 31, 32, 34, 36, 38, or 45 showed 90% or greater as the controlling value.

Test Example 7

Each formulation comprising the present compound 1, 2, 18, 26, or 27 prepared by the process according to the Formulation example 5 was diluted with water until each concentration of the active ingredient reached 500 ppm to prepare each test chemical solution.

Meanwhile, cabbage (on the developmental stage of the third true leaf) was planted in a polyethylene cup, and each of the above test chemical solution was sprayed into the cabbage in a ratio of 20 mL/cup. After the chemical solution was dried, the stem and leaf thereof were cut out and placed in a cup with 50 mL volume. Five (5) heads of 2nd instar larvae of cabbage moth (*Plutella xylostella*) were released into the cup, and the cup was covered with a lid and stored at 25° C. After 5 days, the number of the dead insects was counted, and the mortality of insects was calculated by the following equation.

Mortality of insects (%)=(the number of the dead insects/the number of the test insects)×100

As a result, the treated group that was treated with each test chemical solution comprising the present compound 1, 2, 18, 26, or 27 showed 80% or greater as the mortality of insects.

Test Example 8

Each formulation comprising the present compound 1, 2, 3, 4, 5, 10, 12, 28, 31, 32, 36, 38, 41, 42, 43, or 45 prepared by the process according to the Formulation example 5 was diluted with water until each concentration of the active ingredient reached 200 ppm to prepare each test chemical solution.

Meanwhile, cabbage (on the developmental stage of the third true leaf) was planted in a polyethylene cup, and each of the above test chemical solution was sprayed into the cabbage in a ratio of 20 mL/cup. After the chemical solution was dried, the stem and leaf thereof were cut out and placed in a cup with 50 mL volume. Five (5) heads of 2nd instar larvae of cabbage moth (*Plutella xylostella*) were released into the cup, and the cup was covered with a lid and stored at 25° C. After 5 days, the number of the dead insects was counted, and the mortality of insects was calculated by the following equation.

Mortality of insects (%)=(the number of the dead insects/the number of the test insects)×100

As a result, the treated group that was treated with each test chemical solution comprising the present compound 1, 2, 3, 4, 5, 10, 12, 28, 31, 32, 36, 38, 41, 42, 43, or 45 showed 80% or greater as the mortality of insects.

Test Example 9

A formulation comprising the present compound 18 prepared by the process according to the Formulation example 5 was diluted with water until the concentration of the active ingredient reached 500 ppm to prepare a test chemical solution.

The bottom of a polyethylene cup having 5.5 cm diameter was matted with the same size of a filter paper, and 0.7 mL of the above test chemical solution was added dropwise to the filter paper, and 30 mg sucrose as bait was placed in the cup uniformly. Ten (10) heads of female adult housefly (*Musca domestica*) were released into the polyethylene cup, and the cup was covered with a lid. After 24 hours, the life and death of housefly was investigated, and the number of the dead insects was counted, and the mortality of insects was calculated by the following equation.

Mortality of insects (%)=(the number of the dead insects/the number of the test insects)×100

As a result, the treated group that was treated with the test chemical solution comprising the present compound 18 showed 100% as the mortality of insects.

Test Example 10

A formulation comprising the present compound 18 prepared by the process according to the Formulation example 5 was diluted with water until the concentration of the active ingredient reached 500 ppm to prepare a test chemical solution.

The bottom of a polyethylene cup having 5.5 cm diameter was matted with the same size of a filter paper, and 0.7 mL of the above test chemical solution was added dropwise to the filter paper, and 30 mg sucrose as bait was placed in the cup uniformly. Two (2) heads of male adult German cockroach (*Blattella germanica*) were released into the polyethylene cup, and the cup was covered with a lid. After 6 days, the life and death of German cockroach was investigated, and the number of the dead insects was counted, and the mortality of insects was calculated by the following equation.

Mortality of insects (%)=(the number of the dead insects/the number of the test insects)×100

As a result, the treated group that was treated with the test chemical solution comprising the present compound 18 showed 100% as the mortality of insects.

Test Example 11

Each formulation comprising the present compound 2, 15, 16, 17, or 18 prepared by the process according to the Formulation example 5 was diluted with water until each concentration of the active ingredient reached 500 ppm to prepare each test chemical solution.

Zero point seven (0.7) mL of each of the above test chemical solution was added to 100 mL of ion exchanged water. (The concentration of the active ingredient is 3.5 ppm). Twenty (20) heads of last instar larvae of common house mosquito (*Culex pipiens pallens*) were released into each of the above test chemical solution. After 1 day, the life and death of common house mosquito was investigated, and the number of the dead insects was counted, and the mortality of insects was calculated by the following equation.

Mortality of insects (%)=(the number of the dead insects/the number of the test insects)×100

As a result, the treated group that was treated with each test chemical solution comprising the present compound 2, 15, 16, 17, or 18 showed 95% or greater as the mortality of insects.

Test Example 12

Each formulation comprising the present compound 2, 3, 4, 9, 10, 15, 16, 17, 24, 26, 29, 31, 32, 33, 34, 36, 38, 41, 42, 43, or 45 prepared by the process according to the Formulation example 1 was diluted with water until each concentration of the active ingredient reached 50 ppm to prepare each test chemical solution.

Meanwhile, cucumber (on the developmental stage of the third true leaf) was planted in a polyethylene cup, and each of the above test chemical solution was sprayed into the cucumber in a ratio of 30 mL/cup. After the chemical solution was dried, the second leaf was cut out, and placed in a cup with 200 mL volume. Ten (10) heads of 2nd instar larvae of cucurbit leaf beetle (*Aulacophora femoralis*) were released into the cup, and the cup was covered with a lid and stored at 25° C. After 5 days, the number of the dead insects was counted, and the mortality of insects was calculated by the following equation.

Mortality of insects (%)=(the number of the dead insects/the number of the test insects)×100

As a result, the treated group that was treated with each test chemical solution comprising the present compound 2, 3, 4, 9, 10, 15, 16, 17, 24, 26, 29, 31, 32, 33, 34, 36, 38, 41, 42, 43, or 45 showed 80% or greater as the mortality of insects.

INDUSTRIAL APPLICABILITY

The compound of the present invention has an excellent efficacy for controlling harmful arthropods.

The invention claimed is:
1. A pyrimidinone compound represented by formula (1):

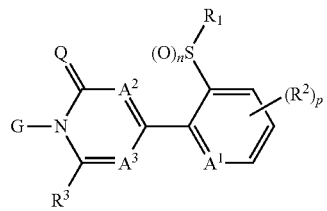

wherein:
   $A^1$ represents a nitrogen atom or a $CR^4$;
   $A^2$ represents a nitrogen atom and $A^3$ represents a $CR^{3b}$, or $A^2$ represents a $CR^{3a}$ and $A^3$ represents a nitrogen atom;
   Q represents an oxygen atom or a sulfur atom;
   G represents a C2-C10 haloalkyl group, a C3-C10 haloalkenyl group, a C3-C10 haloalkynyl group, a (C1-C5 alkyl)-O—(C2-C5 alkyl) group having one or more halogen atoms, a (C3-C5 alkenyl)-O—(C2-C5 alkyl) group having one or more halogen atoms, a (C3-C5 alkynyl)-O—(C2-C5 alkyl) group having one or more halogen atoms, a (C1-C5 alkyl)-S(O)$_m$—(C2-C5 alkyl) group having one or more halogen atoms, a (C3-C5 alkenyl)-S(O)$_m$—(C2-C5 alkyl) group having one or more halogen atoms, a (C3-C5 alkynyl)-S(O)$_m$—(C2-C5 alkyl) group having one or more halogen atoms, or a (C1-C5 alkyl)-C(O)—(C1-C5 alkyl) group having one or more halogen atoms;
   $R^1$ represents a C1-C6 chain hydrocarbon group optionally having one or more halogen atoms;
   $R^2$ represents a C1-C6 chain hydrocarbon group optionally having one or more halogen atoms, a phenyl group optionally having one or more atoms or groups selected from Group A, a 5 membered aromatic heterocyclic group selected from Group B, wherein said 5 membered aromatic heterocyclic group may optionally have one or more atoms or groups selected from Group A, a 6 membered aromatic heterocyclic group selected from Group C, wherein said 6 membered aromatic heterocyclic group may optionally have one or more atoms or groups selected from Group A, a 3 to 7 membered nonaromatic heterocyclic group selected from Group D, wherein said 3 to 7 membered nonaromatic heterocyclic group may optionally have one or more atoms or groups selected from the group consisting of a halogen atom and a C1-C6 alkyl group, a OR$^7$, a NR$^8$R$^9$, a NR$^8$C(O)R$^{10}$, a NR$^8$C(O)OR$^{11}$, a NR$^8$C(O)NR$^{12}$R$^{13}$, a N=CHNR$^{12}$R$^{13}$, a N=S(O)$_x$R$^{12}$R$^{13}$, a S(O)$_y$R$^{12}$, a C(O)OR$^8$, a cyano group, or a halogen atom;
   $R^4$ represents a hydrogen atom or a halogen atom;
   $R^3$, $R^{3a}$, and $R^{3b}$ represent independently of each other a hydrogen atom, a C1-C3 alkyl group optionally having one or more halogen atoms, or a halogen atom;
   $R^7$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a (C1-C3 alkyl)-O—(C1-C3 alkyl) group optionally having one or more halogen atoms, a (C1-C3 alkyl)-S(O)$_y$—(C1-C3 alkyl) group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group, wherein the phenyl moiety in said phenyl C1-C3 alkyl group may optionally have one or more atoms or groups selected from Group A;
   $R^8$ represents a hydrogen atom, a C1-C6 alkyl group optionally having one or more halogen atoms, a C3-C6 alkenyl group optionally having one or more halogen atoms, or a C3-C6 alkynyl group optionally having one or more halogen atoms;
   $R^9$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a (C1-C3 alkyl)-O—(C1-C3 alkyl) group optionally having one or more halogen atoms, a (C1-C3 alkyl)-S(O)$_y$—(C1-C3 alkyl) group optionally having one or more halogen atoms, a C3-C7 cycloalkyl group optionally having one or more halogen atoms, a (C3-C7 cycloalkyl)-(C1-C3 alkyl) group optionally having one or more halogen atoms, a C1-C6 alkyl group having one cyano group, a phenyl C1-C3 alkyl group, wherein the phenyl moiety in said phenyl C1-C3 alkyl group may optionally have one or more atoms or groups selected from Group A, or a (5 or 6 membered heteroaryl)C1-C6 alkyl group, wherein the 5 or 6 membered heteroaryl moiety in said (5 or 6 membered heteroaryl)C1-C6 alkyl group may optionally have one or more atoms or groups selected from Group A;

$R^{10}$ represents a hydrogen atom, a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group, wherein the phenyl moiety in said phenyl C1-C3 alkyl group may optionally have one or more atoms or groups selected from Group A;

$R^{11}$ represents a C1-C6 alkyl group optionally having one or more halogen atoms, a C3-C6 alkenyl group optionally having one or more halogen atoms, a C3-C6 alkynyl group optionally having one or more halogen atoms, a C3-C7 cycloalkyl group optionally having one or more halogen atoms, a (C3-C7 cycloalkyl)-(C1-C3 alkyl) group optionally having one or more halogen atoms, or a phenyl C1-C3 alkyl group, wherein the phenyl moiety in said phenyl C1-C3 alkyl group may optionally have one or more atoms or groups selected from Group A;

$R^{12}$ and $R^{13}$ represent independently of each other a C1-C6 alkyl group optionally having one or more halogen atoms;

$R^{14}$ represents a hydrogen atom, a C1-C6 alkyl group optionally having one or more halogen atoms, a C2-C6 alkylcarbonyl group optionally having one or more halogen atoms, or a C2-C6 alkoxycarbonyl group optionally having one or more halogen atoms;

n represents 0, 1, or 2;
m represents 0, 1, or 2;
p represents 0, 1, 2, or 3, wherein when p represents 2 or 3, each $R^2$ may be identical or different;
x represents 0 or 1; and
y represents 0, 1, or 2;

Group A: a group consisting of a C1-C6 alkyl group optionally having one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a cyano group, and a halogen atom;

Group B:

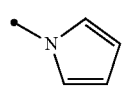
B-1

B-2

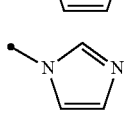
B-3

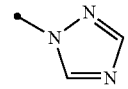
B-4

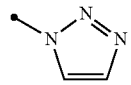
B-5

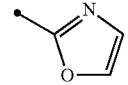
B-6

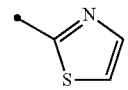
B-7

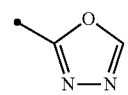
B-8

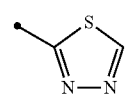
B-9

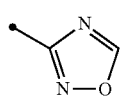
B-10

Group C:

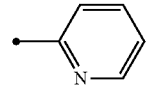
C-1

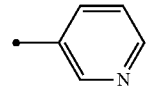
C-2

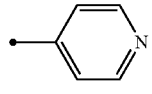
C-3

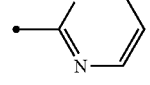
C-4

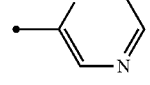
C-5

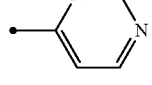
C-6

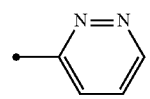
C-7

-continued

C-8
C-9

Group D:

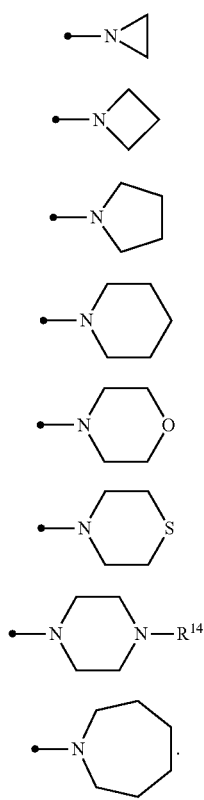

D-1
D-2
D-3
D-4
D-5
D-6
D-7
D-8

2. The compound according to claim 1 wherein $A^2$ is a nitrogen atom and $A^3$ is a $CR^{3b}$.

3. The compound according to claim 1 wherein $A^2$ is a $CR^{3a}$ and $A^3$ is a nitrogen atom.

4. The compound according to claim 1 wherein:
G is a C2-C10 haloalkyl group or a C3-C10 haloalkenyl group;
$R^1$ is a C1-C6 alkyl group optionally having one or more halogen atoms;
$R^2$ is a C1-C6 alkyl group optionally having one or more halogen atoms, a 5 membered aromatic heterocyclic group selected from the group consisting of B-1 group to B-4 group, wherein said 5 membered aromatic heterocyclic group may optionally have one or more halogen atoms, a nonaromatic heterocyclic group selected from the group consisting of D-1 group to D-8 group, wherein said nonaromatic heterocyclic group may optionally have one or more halogen atoms, a C1-C6 alkoxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a di(C1-C6 alkyl)amino group optionally having one or more halogen atoms, a (C1-C6 alkyl)amino group, wherein the C1-C6 alkyl moiety in said (C1-C6 alkyl)amino group may optionally have one or more atoms or groups selected from the group consisting of one or more halogen atoms and a 5 membered aromatic heterocyclic group optionally having one or more halogen atoms, or an amino group;
$R^3$, $R^{3a}$, $R^{3b}$, and $R^4$ are each a hydrogen atom; and
p is 0 or 1.

5. The compound according to claim 1 wherein:
G is a C3-C6 alkyl group having three or more fluorine atoms;
$R^1$ is an ethyl group;
$R^2$ is a C1-C6 alkyl group optionally having one or more halogen atoms, a 5 membered aromatic heterocyclic group selected from the group consisting of B-1 group to B-4 group, wherein said 5 membered aromatic heterocyclic group may optionally have one or more halogen atoms, a nonaromatic heterocyclic group selected from the group consisting of D-1 group to D-8 group, wherein said nonaromatic heterocyclic group may optionally have one or more halogen atoms, a di(C1-C6 alkyl)amino group optionally having one or more halogen atoms, a (C1-C6 alkyl)amino group, wherein the C1-C6 alkyl moiety in said (C1-C6 alkyl) amino group may optionally have one or more atoms or groups selected from the group consisting of one or more halogen atoms and a 5 membered aromatic heterocyclic group optionally having one or more halogen atoms, or an amino group;
$R^3$, $R^{3a}$, $R^{3b}$, and $R^4$ are each a hydrogen atom; and
p is 0 or 1.

6. A composition for controlling a harmful arthropod comprising the compound according to claim 1 and an inert carrier.

7. A method for controlling a harmful arthropod which comprises applying an effective amount of the compound according to claim 1 to a harmful arthropod or a habitat where a harmful arthropod lives.

* * * * *